US008273352B2

(12) United States Patent
Huang et al.

(10) Patent No.: US 8,273,352 B2
(45) Date of Patent: Sep. 25, 2012

(54) HUMANIZED ANTI-FACTOR D ANTIBODIES AND USES THEREOF

(75) Inventors: Arthur Huang, Oakland, CA (US);
Robert Kelley, San Bruno, CA (US);
Henry Lowman, El Granada, CA (US);
Menno Van Lookeren Campagne, San Francisco, CA (US); Charles Winter, Belmont, CA (US)

(73) Assignee: Genentech, Inc., South San Francisco, CA (US)

( * ) Notice: Subject to any disclaimer, the term of this patent is extended or adjusted under 35 U.S.C. 154(b) by 291 days.

(21) Appl. No.: 12/430,479

(22) Filed: Apr. 27, 2009

(65) Prior Publication Data

US 2009/0269338 A1    Oct. 29, 2009

Related U.S. Application Data

(60) Provisional application No. 61/048,689, filed on Apr. 29, 2008, provisional application No. 61/048,431, filed on Apr. 28, 2008.

(51) Int. Cl.
*A61K 39/395* (2006.01)
*C07K 16/18* (2006.01)
*C07K 16/40* (2006.01)
*C12P 21/08* (2006.01)
*C12N 5/10* (2006.01)
*C12N 1/21* (2006.01)

(52) U.S. Cl. ............... 424/133.1; 530/387.3; 530/388.1; 424/136.1; 435/326; 435/328; 435/338; 435/344.1; 435/358; 435/69.6

(58) Field of Classification Search .................. None
See application file for complete search history.

(56) References Cited

U.S. PATENT DOCUMENTS

| 4,816,567 | A | 3/1989 | Cabilly et al. |
| 5,456,909 | A | 10/1995 | Marsh et al. |
| 5,534,615 | A | 7/1996 | Baker et al. |
| 5,624,837 | A | 4/1997 | Fodor et al. |
| 5,627,264 | A | 5/1997 | Fodor et al. |
| 5,679,546 | A | 10/1997 | Ko et al. |
| 5,679,564 | A | 10/1997 | Pace et al. |
| 5,851,528 | A | 12/1998 | Ko et al. |
| 5,853,722 | A | 12/1998 | Rollins et al. |
| 5,856,297 | A | 1/1999 | Fearon et al. |
| 5,856,300 | A | 1/1999 | Rittershaus et al. |
| 5,858,969 | A | 1/1999 | Marsh et al. |
| 5,861,156 | A | 1/1999 | George et al. |
| 6,333,034 | B1 | 12/2001 | Gupta-Bansal et al. |
| 6,410,708 | B1 | 6/2002 | Ashkenazi et al. |
| 6,472,520 | B2 | 10/2002 | Fisher |
| 6,534,058 | B2 | 3/2003 | Fung |
| 6,569,992 | B1 | 5/2003 | LaFleur et al. |
| 6,642,353 | B1 | 11/2003 | McConnell et al. |
| 6,838,554 | B2 | 1/2005 | Ashkenazi et al. |
| 6,956,107 | B2 | 10/2005 | Fung et al. |
| 7,112,327 | B2 | 9/2006 | Fung |
| 7,192,589 | B2 | 3/2007 | Ashkenazi et al. |
| 7,211,400 | B2 | 5/2007 | Ashkenazi et al. |
| 7,282,565 | B2 | 10/2007 | Goddard et al. |
| 7,419,663 | B2 | 9/2008 | Ashkenazi et al. |
| 7,439,331 | B2 | 10/2008 | Fung |
| 7,943,135 | B2 | 5/2011 | Fung et al. |
| 8,007,791 | B2 * | 8/2011 | Hass et al. ............ 424/130.1 |
| 8,067,002 | B2 * | 11/2011 | An et al. .............. 424/145.1 |
| 8,124,090 | B2 * | 2/2012 | Fung et al. ........... 424/145.1 |
| 2002/0081293 | A1 | 6/2002 | Fung et al. |
| 2003/0129187 | A1 | 7/2003 | Fung et al. |
| 2003/0207309 | A1 | 11/2003 | Hageman et al. |
| 2004/0152105 | A1 | 8/2004 | Vogt et al. |
| 2005/0191298 | A1 * | 9/2005 | Bell et al. ............. 424/144.1 |
| 2005/0197285 | A1 | 9/2005 | Rosen et al. |
| 2005/0222027 | A1 | 10/2005 | Chiang et al. |
| 2006/0067935 | A1 | 3/2006 | Ambati |
| 2006/0233803 | A1 | 10/2006 | Ashkenazi et al. |
| 2006/0240020 | A1 | 10/2006 | Fung et al. |
| 2007/0190054 | A1 | 8/2007 | Ashkenazi et al. |
| 2008/0118506 | A1 * | 5/2008 | An et al. ............... 424/133.1 |
| 2008/0193442 | A1 | 8/2008 | Fung et al. |
| 2009/0181017 | A1 | 7/2009 | Hass et al. |
| 2009/0214538 | A1 | 8/2009 | Fung et al. |
| 2011/0123528 | A1 | 5/2011 | An et al. |
| 2011/0165622 | A1 | 7/2011 | An et al. |
| 2011/0282034 | A1 * | 11/2011 | Hass et al. ............ 530/387.3 |

FOREIGN PATENT DOCUMENTS

| EP | 0 239 400 B1 | 3/1994 |
| WO | WO 95/29697 | 11/1995 |
| WO | WO 99/27098 | 3/1999 |
| WO | 99/42133 | 8/1999 |
| WO | WO 99/40100 | 8/1999 |
| WO | WO 99/46281 | 9/1999 |
| WO | WO 00/12703 | 3/2000 |
| WO | WO 00/37638 | 6/2000 |
| WO | 00/42072 | 7/2000 |

(Continued)

OTHER PUBLICATIONS

Casset et al. Biochem Biophys Res Comm. 2003; 307:198-205.*
Chen et al. J Mol Biol. 1999; 293:865-881.*
Holm et al. Mol Immunol. 2007; 44(6):1075-1084.*
MacCallum et al. J Mol Biol. 1996; 262:732-745.*
Padlan et al. Proc Natl Acad Sci USA, 1989; 86:5938-5942.*
Paul, We, editor. Fundamental Immunology, Third Edition. Raven Press, New York, 1993, pp. 292-295.*
Rudikoff et al. Proc Natl Acad Sci USA, 1982; 79(6):1979-1983.*
Vajdos et al. J Mol Biol. 2002; 320(2):415-428.*

(Continued)

*Primary Examiner* — Elizabeth C Kemmerer
*Assistant Examiner* — Kimberly A Ballard
(74) *Attorney, Agent, or Firm* — Jones Day

(57) ABSTRACT

The invention relates to anti-Factor D antibodies, their nucleic acid and amino acid sequences, the cells and vectors that harbor these antibodies and their production and their use in the preparation of compositions and medicaments for treatment of diseases and disorders associated with excessive or uncontrolled complement activation. These antibodies are useful for diagnostics, prophylaxis and treatment of disease.

35 Claims, 13 Drawing Sheets

FOREIGN PATENT DOCUMENTS

| WO | WO 00/53749 | | 9/2000 |
|---|---|---|---|
| WO | WO 00/53758 | | 9/2000 |
| WO | WO 01/04311 | | 1/2001 |
| WO | WO 01/36432 | | 5/2001 |
| WO | WO 00/36102 | | 6/2001 |
| WO | WO 01/40466 | | 6/2001 |
| WO | WO 02/00690 | | 1/2002 |
| WO | WO 02/08284 | | 1/2002 |
| WO | WO 02/30985 | | 4/2002 |
| WO | WO 02/30986 | A2 | 4/2002 |
| WO | WO 2004014953 | * | 2/2004 |
| WO | WO 2004/022594 | | 3/2004 |
| WO | WO 2005/025509 | | 3/2005 |
| WO | WO 2005102387 | * | 11/2005 |
| WO | WO 2006/042329 | | 4/2006 |
| WO | WO 2006/062716 | | 6/2006 |
| WO | WO 2006/071856 | | 7/2006 |
| WO | WO 2006/088950 | | 8/2006 |
| WO | WO 2007/044668 | | 4/2007 |
| WO | 2007/056227 | | 5/2007 |
| WO | WO 2007053447 | * | 5/2007 |
| WO | WO 2007/087384 | | 8/2007 |
| WO | 2008/055206 | | 5/2008 |
| WO | WO 2008/147883 | | 12/2008 |
| WO | WO 2009/134711 | | 11/2009 |

OTHER PUBLICATIONS

Bora et al., 2006, "Complement activation via alternative pathway is critical in the development of laser-induced choroidal neovascularization: role of factor B and factor H", J. Immunol., 177:1872-1878.*

Diamond et al., 1984, "Somatic mutation of the T15 gives rise to an antibody with autoantibody specificity", Proc. Natl. Acad. Sci. 81:5841-5844.*

Ohno et al., 1985, "Antigen-binding specificities of antibodies are primarily determined by seven residues of VH", Proc. Natl. Acad. Sci. 82:2945-2949.*

Undar et al., 2002, "Novel anti-factor D monoclonal antibody inhibits complement and leukocyte activation in a baboon model of cardiopulmonary bypass", Ann Thorac. Surg., 74(2): 355-62.*

Accession NM_001928, "Homo sapiens complement factor D (adipsin) (CFD), mRNA". Retrieved Apr. 26, 2009.*

Amit et al., "Three-Dimensional Structure of an Antigen-Antibody Complex at 2.8 A Resolution" *Science* 233:747-753 (Aug. 1986).

Amsterdam et al., "Limitation of reperfusion injury by a monoclonal antibody to C5s during myocardial infarction in pigs" *Am J Physiol.* 268 (1 Pt 2) :H448-57 (Jan. 1995).

Barnum et al., "Quantitation of complement factor D in human serum by a solid-phase radioimmunoassay" *J Immunol Methods* 67(2) : 303-9 (Mar. 16, 1984).

Champe et al., "Monoclonal antibodies that block the activity of leukocyte function-associated antigen 1 recognize three discrete epitopes in the inserted domain of CD11a" *Journal of Biological Chemistry* 270 :1388-1394 (1995).

Chothia and Lesk, "Canonical Structures for the Hypervariable Regions of Immunoglobulins" *J Mol Biol.* 196(4):901-917 (Aug. 20, 1987).

Ferris et al., "A Simplified Severity Scale Scale for Age-Related Macular Degeneration" *Arch Ophthalmol.* (AREDS Report No. 18) 123:1570-74 (Nov. 2005).

Harlow et al., "Chapter 14: Immunoassays" *Antibodies, A Laboratory Manual*, Cold Spring Harbor Laboratory pp. 553-612 (1988).

Holers, "Chapter 24 Complement", R.R. Rich edition, Mosby Press pp. 363-391 (1996).

Homeister et al., "Soluble complement receptor type 1 prevents-human complement-mediated damage of the rabbit isolated heart" *J Immunol.* Feb. 1, 1993;150 (3) :1055-64 150(3) :1055-64 (Feb. 1, 1993).

Jaffe, Jaffe, Ashton, and Pearson "pp. 86-95, 111-129, 193-203, 203-225, 249-263" & *Intraocular Drug Delivery*, Taylor & Francis (Mar. 2006).

Jager et al., "Age-related macular degeneration" *N Engl J Med.* 359(16) :1735-6 (Oct. 16, 2008).

Jones et al., "Replacing the Complementarity-Determining Regions in a Human Antibody with Those From a Mouse" *Nature* 321 (6069) : 522-525 (May 29, 1986).

Kostavasili et al., "Mechanism of complement inactivation by glycoprotein C of herpes simplex virus" *J Immunol.* 158 (4) :1763-71 (Feb. 15, 1997).

Kroshus et al., "Complement inhibition with an anti-C5 monoclonal anitbody prevents acute cardiac tissue injury in an ex vivo model of pig-to-human xenotransplantation" *Transplantation* 60(11) :1194-202 (Dec. 15, 1995).

Lesavre and Eberhard, "Mechanism of action of factor D of the alternative complement pathway." *J Exp Med.* 148(6) :1498-509 (Dec. 1, 1978).

Morgan et al., "Clinical complementology: recent progress and future trends." *Eur J Clin Invest.* 24 (4) :219-28 (Apr. 1994).

Morley and Walport, "Factor D" *Complement Facts Book*, Academic Press (2000) pp. 17, 69-72 (2000).

Pascual et al., "Metabolism of complement factor D in renal failure" *Kidney International* 34(4) :529-36 (Oct. 1988).

Powell, Amphlett et al., "A compendium and hydropathy/flexibility analysis of common reactive sites in proteins: reactivity at Asn, Asp, Gln, and Met motifs in neutral pH solution" *Pharm Biotechnol.* 9:1-140 (1996).

Rabinovici et al., "Role of complement in endotoxin/platelet-activating factor-induced lung injury" *J Immunol.* 149(5) :1744-50 (Sep. 1, 1992).

Riechmann et al., "Reshaping Human Antibodies for Therapy" *Nature* 332:323-327 (Mar. 24, 1988).

Rinder et al., "Blockade of C5a and C5b-9 generation inhibits leukocyte and platelet activation during extracorporeal circulation" *J Clin Invest.* 96(3) :1564-72 (Sep. 1995).

Sallo et al., "The International Classification system and the progression of age-related macular degeneration" *Curr Eye Res.* 34(3) :238-40 (Mar. 2009).

Verhoeyen et al., "Reshaping Human Antibodies: Grafting an Antilysozyme Activity" *Science* 239:1534-1536 (Mar. 1988).

Volanakis et al., "Renal filtration and catabolism of complement protein D" *N Engl J Med.* 312(7) :395-9 (Feb. 14, 1985).

Wang et al., "Amelioration of lupus-like autoimmune disease in NZB/WF1 mice after treatment with a blocking monoclonal antibody specific for complement component C5" *Proc Natl Acad Sci U S A.* 93(16) :8563-8 (Aug. 6, 1996).

Wang et al., "Anti-C5 monoclonal antibody therapy prevents collagen-induced arthritis and ameliorates established disease" *Proc Natl Acad Sci U S A.* 92(19) :8955-9 (Sep. 12, 1995).

Weisman et al., "Soluble human complement receptor type 1: in vivo inhibitor of complement suppressing post-ischemic myocardial inflammation and necrosis" *Science* 249(4965) :146-51 (Jul. 13, 1990).

Wiesmann et al., "Structure of C3b in complex with CRIg gives insights into regulation of complement activation" *Nature* 444(7116) : 217-20 (Nov. 9, 2006).

U.S. Appl. No. 09/253,689, filed Feb. 20, 1999, Fung et al.

U.S. Appl. No. 13/081,203, filed Apr. 6, 2011, Fung et al.

Aderem et al., 1999, "Mechanisms of phagocytosis in macrophages." Annu. Rev. Immunol. 17: 593-623.

Akif et al., 2002, "Novel anti-factor D monoclonal antibody inhibits complement and leukocyte activation in baboon model of cardiopulmonary bypass." Annals of Thoracic Surgery 74(2):355-362.

Ambati, J. et al., 2003. "An animal model of age-related macular degeneration in senescent Ccl-2- or Ccr-2-deficient mice." Nat. Med. Nov; 9(11):1390-7 Epub Oct. 19, 2003).

Anderson, D.H., et al., 2002, "A role for local inflammation in the formation of drusen in the aging eye." Am. J. Ophthalmol., 134:411-31.

Arrate et al., 2001, "Cloning of human junctional adhesion molecule 3 (JAM3) and its identification as the JAM2 counter-receptor." J Biol. Chem.. 276(49):45826-45832.

Attwood, 2000, "The Babel of bioinformatics." Science 290:471-473.

Bertozzi et al., 1997. "An Elisa for selectins based on binding to a physiological ligand." J. Immunol. Methods 203(2):157-65.

Blast Report, expasy.org/cgi-bininiceprot.pl/printable?ac=Q80WA3, dated Mar. 1, 2004.

Bok, D., 2005. "Evidence for an inflammatory process in age-related macular degeneration gains new support." Proc. Natl. Acad. Sci. (USA). 102:7053-4.

Bora, et al., 2005. "Role of Complement and Complement Membrane Attack Complex in Laser-Induced Choroidal Neovascularization." J. of Immunol. 174: 491-497.

Brown et al.. 2007, "Mechanisms of disease: the complement system in renal injury—new ways of looking at an old foe." Nat Clin Pract Nephrol. 3(5):277-86.

Brown, 1992, "Complement receptors, adhesion, and phagocytosis," Infectious agents and disease, 1:63-70.

Carroll, 2004, "The complement system in regulation of adaptive immunity." Nat. Immunol. 5(10):981-986.

Carter et al.. "Humanization of an anti-p185HER2 antibody for human cancer therapy". Proc. Natl. Acad. Sci. USA, 89:4285-4289 (1992).

Database Genbank (Apr. 24, 2001), "Human Pro 1868 Protein" Database Accession No: AAB80272 XP002448361, dated Jun. 15, 2007.

Edwards et al., 2005, "Complement factor H polymorphism and age-related macular degeneration," Science 308: 419-421.

Esparza-Gordillo, J., et al., 2004, "Genetic and environmental factors influencing the human factor H plasma levels." Immunogenetics, 56:77-82.

Evans et al., "Rapid Expression of an Anti-Human C5 Chimeric Fab Utilizing a Vector that Replicates in COS and 293 Cells," J. Immunol., 184: 123-138 (1995).

Parries, T.C., et al., 1990, "The mechanism of activation of the alternative pathway of complement by cell-bound C4b." Mol. Immunol., 27:1155-116.

Fung , M. et al., 2000, "Inhibition of Complement, Neutrophil, and Platelet Activation by an Anti-Factor D Antibody During Extracorporeal Circulation". Presented in the 18$^{th}$ Annual Houston Conference on Biomedical Engineering Research. Houston, Texas. Feb. 10-11, 2000 (Abstract).

Gao et al., 1995, "An enzyme-linked immunosorbent assay to identify inhibitors of activation of platelet integrin alpha IIb beta 3" J. Immunol. Methods. 181(1):55-64.

Hageman et al., 2005, "A Common haplotype in the complement regulatory gene factor H (HF1/CFH) predisposes individuals to age-related macular degeneration." Proc. Natl. Acad Sci. 102(20): 7227-7232.

Hageman, G.S., et al., 2001, "An integrated hypothesis that considers drusen as biomarkers of immune-mediated processes at the RPE-Bruch's membrane interface in aging and age-related macular degeneration." Prog. Retin. Eye Res., 20:705-32.

Haines, J.L., et al., 2005, "Complement factor H variant increases the risk of age-related macular degeneration." Science.308:419-21.

Hakimi et al.. "Reduced immunogenicity and improved pharmacokinetics of humanized anti-Tac in cynomolgus monkeys". J. Immunol., 147(4):1352-1959 (1991).

Harboe et al.. "The quantitative role of alternative pathway amplification in classical pathway induced terminal complement activation." Clinical and Experimental Immunology, 138(3):439-446 (2004).

Haubenwallner et al., "A novel missense mutation in the gene for lipoprotein lipase resulting in a highly conservative amino acid substitution (Asp$^{180}$ →Glu) causes familial chylomicronemia (type 1 hyperlipoproteinemia)" Genomics, 18(2):392-396 (1993).

Holers et al., 1992, "The evolution of mouse and human complement C3-binding proteins: divergence of form but conversation of function." lmmnol. Today 13(6):231-236.

Houghten et al., 1992, "The use of synthetic peptide combinatorial libraries for the identification of bioactive peptides." Biotechniques 13(3):412-21.

Huber-Lang et al., "Role of C5a in Multiorgan Failure During Sepsis" J. of Immunology, 166:1193-1198 (2001).

Inagi et al., 1993, "Decreased Activity of Complement-Mediated Immune Complex Clearance in Hemodialysis Patients," Clin. Immune & Immunopath. 68(3):333-339.

Jaffers et al., "Monoclonal antibody therapy. Anti-idiotypic and non-anti-idiotypic antibodies to OKT3 arising despite intense immunosuppression". Transplantation 41(5):572-578 (1986).

Janeway et al., 1997, *Immunobiology* (13-5 to 13-7) 3$^{rd}$ edition. London, Eng Current Biology ltd.

Janssen et al., 2007, "Structural insights into the central complement component C3." Molec. Immunol. 44:3-10.

Johnson, L.V., et al., 2001, "Complement activation and inflammatory processes in Drusen formation and age related macular degeneration." Exp. Eye Res., 73:887-96.

Junghans et al.. "Anti-Tac-H, a humanized antibody to the interleukin 2 receptor with new features for immunotherapy in malignant and immune disorders". Cancer Res. 50:1495-1502 (1990).

Katschke et al., 2007, "A Novel inhibitor of the alternative pathway of complement reverses inflammation and bone destruction in experimental arthritis." Brief Definitive Report 204(6): 1319-1325.

Khazaeli et al., "Phase I trial of multiple large doses of murine monoclonal antibody CO17-IA. II. Pharmacokinetics and immune response". J. Natl. Cancer Inst. 80:937-942 (1988).

Kim et al., 2005, "Characterization of monoclonal antibody specific to the Z3291g protein, a member of immunoglobulin superfamily." Immunol. Letters 99:153-161.

Klein et al., 2005, "Complement Factor H Variant Increases the Risk of Age-Related Macular Degeneration," Science, 308:385-389.

Klohs et al., 1997, "Inhibitors of tyrosine kinase." Curr. Opin. Oncol. 19 9(6):562-8.

Krzystolik M. G., et al., 2002, "Prevention of experimental choroidal neovascularization with intravitreal anti-vascular endothelial growth factor antibody fragment." Arch Ophthalm., 120:338-346.

Lam et al., 1997, "Application of combinatorial library methods in cancer research and drug discovery." Anticancer Drug Des 12(3): 145-67.

Langnaese et al., 2000, "Cloning of Z391g, a novel gene with immunoglobulin-like domains located on human chromosome XI" BBA, 552-555.

Laubser et al., "Inhibition of Complement, Neutrophil, and Platelet Activation by an Anti-Factor D Antibody During Extracorporeal Circulation", Presented at the Annual Meeting of American Society of Anestesiologists, San Francisco, California, Oct. 14-18, 2000 (Abstract A-657).

Lee et al., 2006, "Z391g is expressed on macrophages and may mediate inflammatory reactions in arthritis and artherosclerosis." J of Leukocyte boil. 80: 922-928.

Makrides et al., 1998, "Therapeutic Inhibition of the Complement System." Pharmacological Reviews. 50(1):59-87.

Matson et al., 2000, "Evolving concepts of therapy for sepsis and septic shock and the use of hyperpermeable memberanes", Current Opinion in Critical Care 6:431-436.

Miller et al., "Monoclonal antibody therapeutic trials in seven patients with T-cell lymphoma". Blood. 62:988-995 (1983).

Mulligan et al., "Protective Effects of Soluble CR1 in Complement and Neutrophil-Medicated Tissue Injury", J. Immunol., 148(5):1479-1485 (1992).

Narayana et al., "Structure of Human Factor D:A Complement System Protein at 20.degree. Resolution", J. Mol. Biol., 235: 695-708 (1994).

Niemann et al., "The Use of Monoclonal Antibodies as Probes of the Three Dimensional Structure of Human Complement Factor D", J. Immunol., 132(2): 809-815 (1984).

Omer et al., 1997. "CAIA2X-competitive inhibitors of farnesyltransferase as anti-cancer agents"Trends Pharmacol Sci. 18(11):434-44.

Pascual et al., 1990. "A monoclonal which antibody which blocks the function of factor D of human complement." J Immunol. Methods 127(2)263-9.

Pascual et al.. 1993, "Inhibition of complement alternative pathway in mice with Fab antibody to recombinant adipsin/factor D." Eur J. Immunol. 23(6): 1389-92.

Petrukhin et al., 2007, "New therapeutic targets in atrophic age-relied macular degeneration." Expert Opinion on Therapeutic targets 11(5):625-639.

Pyz et al., 2006. "C-type lectin-like receptors on myeloid cells." Annals of Med 38:242-251.

Ray et al., 1997, "Thrombin receptor: a novel target for antiplatelet drug development" Thromb Res. 87(1): 37-50.

Ricklin and Lambris, 2007, "Complement-targeted therapeutics." Nat Biotechnol. 25(11):1265-75.

Rodriguez De Cordoba S., et al., 2004, "The human complement factor H: functional roles, genetic variations and disease associations." Mol. Immunol. 41:355-67.

Rohrer et al., 2009, "A targeted inhibitor of the alternative complement pathway reduces angiogenesis in a mouse model of age-related macular degeneration." Invest Ophthalmol Vis Sci. (7):3056-64.

Ross et al., 1985, "Membrane complement receptors specific for bound fragments of C3." Advances in Immunol, 37:217-267.

Sahu et al., 1993, "Identification of multiple sites of interaction between heparin and the complement system" Mol. Immunol. 30(7): 679-84.

Sato et al., 1997, "A new method for studying the binding of human IgE to CD23 and the inhibition of this binding." J Immunol. Methods 209(1): 59-66.

Sears et al., "Effects of monoclonal antibody immunotherapy on patients with gastrointestinal adenocarcinoma". J. Biol. Response Modifiers. 3:138-150 (1984).

Shawler et al., Human immune response to multiple injections of murine monoclonal IgG. J. Immunol. 135(2):1530-1535 (1985).

Sim et al., "Serine Proteases of the Complement System", Biochemical Society Transactions, vol. 28, Pt.5, pp. 545-550 (2000).

Sims et al., "A humanized CD18 antibody can block function without cell destruction". J. Immunol., 151(4):2296-2308 (1993).

Skolnick et al., 2000, "From genes to protein structure and function: novel applications of computational approaches in the genomic era." Trends in Biotech 18: 34-39.

Stadel et al., 1997, "Orphan G protein-coupled receptors: a neglected opportunity for pioneer drug discovery" Trends Pharmacol. Sci 18(11 ): 430-7.

Strausberg et al., 2002, "Generation and initial analysis of more than 15.000 full-length human and mouse cDNA se uences," Proc. Natl. Acad Sci. 99:26—16899-16903.

Strawn et al., 1996, "Fik-1 as a target for tumor growth inhibition." Cancer Res. 56(15):3540-5.

Stuart et al., 2005, "Phagocytosis: Elegant complexity." Immunity 22:539-550.

Tanhehco et al., 1999, "The anti-factor D antibody, MAb 166-32, inhibits the alternative pathway of the human complement system." Transplant Proc. 31(5):2168-71.

Taylor et al., 2003, "Pattern recognition receptors and differentiation antigens define murine myeloid cell heterogeneity ex vivo." Eur. J. Immunol. 33:2090-2097.

Taylor et al., 2005. "Macrophage receptors and immune recognition", Annu. Rev. ImmunoL, 23: 901-944.

Thurman et al., 2006. "The central rote of the alternative complement pathway in human disease." J immune!. 176:1305-1310.

Tsukita et al., 2001, "Multifunctional strands in tight junctions." Nat. Revew. 2:285-293.

Undar et al., "Novel Anti-Factor D Monoclonal Antibody Inhibits Complement, Neutrophil, and Platelet Activation in a Simulated Pediatric Cardiopulmonary Bypass Circuit"., Presented in the 46th 5 Annual Conference of the American Society for Artificial Internal Organs. New York, N.Y., Jun. 28-Jul. 1, 2000, (Abstract).

Underhill eta l., 2002, "Phagocytosis of microbes: Complexity in action." Annu Rev. Immunol. 20:825-852.

Volanakis et al., "Complement Enzymes", In: *The Human Complement System in Health & Disease*, Chapter 4, pp. 49-81, Eds., J. Volonakis & M. M. Frank, Published by Marcel Dekker, Inc. New York (1998).

Volanakis et al., "Complement Factor D, A Novel Serine Protease", Protein Science. 5:553-564 (1996).

Walker et al., 2002, "Z391g is co-expressed with activation macrophage genes." Biochemica et Biophysica Acta 1574:387-390.

Walport, 2001 "Complement first of two parts." Advances in Immunol. Neng J med 344(14): 1058-1066.

White et al., "Human Adipsin is Identical to Complement Factor D and is Expressed at High Levels in Adipose Tissue", J. Bio. Chem, 267(13): 9210-9213 (1992).

Wilson et al., 1993, "A competitive inhibition ELISA for the quantification of human interferon-gamma" J. Immunol. Methods 162(2):247-55.

Wu et al., 1999, "Humanization of a murine monoclonal antibody by simultaneous optimization of framework and CRD residues." JMB 294:151-162.

Zareparsi, S., et al., 2005, "Strong association of the Y402H variant in complement factor H at 1q32 with susceptibility to age-related macular degeneration." Am J Hum Genet. 77:149-53.

Zeng et al., 2010, "Lack of Association of CFD polymorphisms with advanced age-related macular degeneration." Molec. Vis. 16:2273-2278.

International Search Report, dated Jun. 26, 2008, of PCl/US2007/083172 now, WO 2008/055206.

International Preliminary Report on Patentability, dated May 2, 2009, of PCT/US2007/083172 now, WO 2008/055206.

Written Opinion dated May 2, 2009, of PCT/US2007/083172 now, WO 2008/055206.

Written Opinion dated Nov. 24, 2009 of PCT/US2008/064526, now WO 2008/147883.

International Preliminary Examination Report, dated Nov. 24, 2009 of PCT/US2008/064526, now WO 2008/147883.

International Search Report, dated Aug. 14, 2008, of PCT/US2008/064526, now WO 2008/147883.

International Search Report dated Sep. 15, 2009 of PCT/US09/41785. now WO 2009/134711.

Written Opinion dated Oct. 28. 2010 of PCT/US09/41785, now WO 2009/134711.

International Search Report dated Aug. 10, 2007 of PCT/US06/043103, now WO 2007/056227.

Written Opinion dated Aug. 10. 2007 of PCT/US06/043103. now WO 2007/056227.

* cited by examiner

FIG. 1

| FIG. 1A | FIG. 1B | FIG. 1C |

FIG. 1A

| Kabat# | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | A1 | A2 | A3 | A4 | 24 | 25 | 26 | 27 | A | B | C | D | E | F | P | 28 | A5 | A6 | A7 | A8 | A9 | A10 | A11 | 29 | 30 | 31 | 32 | 33 | 34 | 35 | 36 | 37 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| | | | | | | | | | | | | | | | | | | | | | | | | | | | | | | | | | | | | | | | | | | | | | | | Kabat - CDR L1 | | | | | | | | |
| | | | | | | | | | | | | | | | | | | | | | | | | | | | | | | | | | | | | | | | | | | | | | | | Chothia - CDR L1 | | | | | | | |
| | | | | | | | | | | | | | | | | | | | | | | | | | | | | | | | | | | | | | | | | | | | | | | Contact - CDR L1 | | | | | | | | |
| K1 Consensus | D | I | Q | M | T | Q | S | P | S | S | L | S | A | S | V | G | D | R | V | T | I | T | C | R | A | S | Q | | | | | | | | | | | | G | I | S | S | Y | L | A | | | N | W | Y | Q |
| #111-LC | D | I | Q | V | T | Q | S | P | S | S | L | S | A | S | V | G | D | R | V | T | I | T | C | I | T | S | T | | | | | | | | | | | | D | I | D | D | D | N | M | | | N | W | Y | Q |
| 238-LC | D | I | Q | V | T | Q | S | P | S | S | L | S | A | S | V | G | D | R | V | T | I | T | C | I | T | S | T | | | | | | | | | | | | D | I | D | D | D | N | M | | | N | W | Y | Q |
| 238-1-LC | D | I | Q | V | T | Q | S | P | S | S | L | S | A | S | V | G | D | R | V | T | I | T | C | I | T | S | T | | | | | | | | | | | | D | I | D | D | D | N | M | | | N | W | Y | Q |
| 238-2-LC | D | I | Q | V | T | Q | S | P | S | S | L | S | A | S | V | G | D | R | V | T | I | T | C | I | T | S | T | | | | | | | | | | | | D | I | D | D | D | L | N | | | N | W | Y | Q |
| 238-3-LC | D | I | Q | V | T | Q | S | P | S | S | L | S | A | S | V | G | D | R | V | T | I | T | C | I | T | S | T | | | | | | | | | | | | D | I | D | D | D | I | N | | | N | W | Y | Q |
| 238-4-LC | D | I | Q | V | T | Q | S | P | S | S | L | S | A | S | V | G | D | R | V | T | I | T | C | I | T | S | T | | | | | | | | | | | | D | I | D | D | D | N | A | | | N | W | Y | Q |
| 238-5-LC | D | I | Q | V | T | Q | S | P | S | S | L | S | A | S | V | G | D | R | V | T | I | T | C | I | T | S | T | | | | | | | | | | | | D | I | D | D | D | N | Q | | | N | W | Y | Q |
| 238-6-LC | D | I | Q | V | T | Q | S | P | S | S | L | S | A | S | V | G | D | R | V | T | I | T | C | I | T | S | T | | | | | | | | | | | | D | I | D | D | D | N | N | | | N | W | Y | Q |
| 238-7-LC | D | I | Q | V | T | Q | S | P | S | S | L | S | A | S | V | G | D | R | V | T | I | T | C | I | T | S | T | | | | | | | | | | | | D | I | D | D | D | N | N | | | N | W | Y | Q |
| 238-8-LC | D | I | Q | V | T | Q | S | P | S | S | L | S | A | S | V | G | D | R | V | T | I | T | C | I | T | S | T | | | | | | | | | | | | D | I | D | D | D | N | N | | | N | W | Y | Q |
| 238-9-LC | D | I | Q | V | T | Q | S | P | S | S | L | S | A | S | V | G | D | R | V | T | I | T | C | I | T | S | T | | | | | | | | | | | | D | I | D | D | D | N | N | | | N | W | Y | Q |
| 238-10-LC | D | I | Q | V | T | Q | S | P | S | S | L | S | A | S | V | G | D | R | V | T | I | T | C | I | T | S | T | | | | | | | | | | | | D | I | D | D | D | N | N | | | N | W | Y | Q |
| 238-11-LC | D | I | Q | V | T | Q | S | P | S | S | L | S | A | S | V | G | D | R | V | T | I | T | C | I | T | S | T | | | | | | | | | | | | D | I | D | D | D | N | N | | | N | W | Y | Q |

FIG. 1B

| Kabat# | 38 | 39 | 40 | 41 | 42 | 43 | 44 | 45 | 46 | 47 | 48 | A | 49 | 50 | 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| | | | | | | | | | | | | | | | | B1 | B2 | B3 | B4 | B5 | B6 | B7 | | | | | | | | | | | | | | | | | | | | | | |
| K1 Consensus | Q | K | P | G | K | A | P | K | L | L | I | | Y | A | A | S | S | L | Q | S | G | V | P | S | R | F | S | G | S | G | S | G | T | D | F | T | L | T | I | S | S | L | Q | P |
| #111-LC | Q | K | P | G | K | V | P | K | L | L | I | | Y | S | G | G | N | T | L | R | P | G | V | P | S | R | F | S | G | S | G | S | G | T | D | F | T | L | T | I | S | S | L | Q | P |
| 238-LC | Q | K | P | G | K | V | P | K | L | L | I | | Y | S | G | G | N | T | L | R | P | G | V | P | S | R | F | S | G | S | G | S | G | T | D | F | T | L | T | I | S | S | L | Q | P |
| 238-1-LC | Q | K | P | G | K | V | P | K | L | L | I | | Y | S | G | G | N | T | L | R | P | G | V | P | S | R | F | S | G | S | G | S | G | T | D | F | T | L | T | I | S | S | L | Q | P |
| 238-2-LC | Q | K | P | G | K | V | P | K | L | L | I | | Y | S | G | G | N | T | L | R | P | G | V | P | S | R | F | S | G | S | G | S | G | T | D | F | T | L | T | I | S | S | L | Q | P |
| 238-3-LC | Q | K | P | G | K | V | P | K | L | L | I | | Y | S | G | G | N | T | L | R | P | G | V | P | S | R | F | S | G | S | G | S | G | T | D | F | T | L | T | I | S | S | L | Q | P |
| 238-4-LC | Q | K | P | G | K | V | P | K | L | L | I | | Y | S | G | G | N | T | L | R | P | G | V | P | S | R | F | S | G | S | G | S | G | T | D | F | T | L | T | I | S | S | L | Q | P |
| 238-5-LC | Q | K | P | G | K | V | P | K | L | L | I | | Y | S | G | G | N | T | L | R | P | G | V | P | S | R | F | S | G | S | G | S | G | T | D | F | T | L | T | I | S | S | L | Q | P |
| 238-6-LC | Q | K | P | G | K | V | P | K | L | L | I | | Y | S | G | G | S | T | L | R | P | G | V | P | S | R | F | S | G | S | G | S | G | T | D | F | T | L | T | I | S | S | L | Q | P |
| 238-7-LC | Q | K | P | G | K | V | P | K | L | L | I | | Y | S | G | G | A | T | L | R | P | G | V | P | S | R | F | S | G | S | G | S | G | T | D | F | T | L | T | I | S | S | L | Q | P |
| 238-8-LC | Q | K | P | G | K | V | P | K | L | L | I | | Y | S | G | G | N | T | L | R | P | G | V | P | S | R | F | S | G | S | G | S | G | T | D | F | T | L | T | I | S | S | L | Q | P |
| 238-9-LC | Q | K | P | G | K | V | P | K | L | L | I | | Y | S | G | G | N | T | L | R | P | G | V | P | S | R | F | S | G | S | G | S | G | T | D | F | T | L | T | I | S | S | L | Q | P |
| 238-10-LC | Q | K | P | G | K | V | P | K | L | L | I | | Y | S | G | G | N | T | L | R | P | G | V | P | S | R | F | S | G | S | G | S | G | T | D | F | T | L | T | I | S | S | L | Q | P |
| 238-11-LC | Q | K | P | G | K | V | P | K | L | L | I | | Y | S | G | G | N | T | L | R | P | G | V | P | S | R | F | S | G | S | G | S | G | T | D | F | T | L | T | I | S | S | L | Q | P |

Kabat – CDR L2
Chothia – CDR L2
Contact – CDR L2

| | Kabat# | 81 82 83 84 85 86 87 88 | 89 90 91 92 93 94 95 A B C D E F | 96 97 98 99 100 101 102 103 104 105 106 107 108 | |
|---|---|---|---|---|---|
| | | | Kabat – CDR L3 | | |
| | | | Chothia – CDR L3 | | |
| | | | Contact – CDR L3 | | |
| | K1 | | C1 C2 C3 C4 C5 C6 C7 | C8 C9 | |
| Consensus | | E D F A T Y Y C | Q Q Y N S Y P | - - T F G Q G T K V E I K R | SEQ ID NO: 65 |
| #111-LC | | E D V A T Y Y C | L Q S D S L P | Y T F G Q G T K L E I K | SEQ ID NO: 1 |
| 238-LC | | E D V A T Y Y C | L Q S D S L P | Y T F G Q G T K V E I K | SEQ ID NO: 6 |
| 238-1-LC | | E D V A T Y Y C | L Q S D S L P | Y T F G Q G T K L E I K | SEQ ID NO: 7 |
| 238-2-LC | | E D V A T Y Y C | L Q S D S L P | Y T F G Q G T K V E I K | SEQ ID NO: 8 |
| 238-3-LC | | E D V A T Y Y C | L Q S D S L P | Y T F G Q G T K L E I K | SEQ ID NO: 9 |
| 238-4-LC | | E D V A T Y Y C | L Q S D S L P | Y T F G Q G T K L E I K | SEQ ID NO: 10 |
| 238-5-LC | | E D V A T Y Y C | L Q S D S L P | Y T F G Q G T K L E I K | SEQ ID NO: 11 |
| 238-6-LC | | E D V A T Y Y C | L Q S D S L P | Y T F G Q G T K L E I K | SEQ ID NO: 12 |
| 238-7-LC | | E D V A T Y Y C | L Q S D S L P | Y T F G Q G T K L E I K | SEQ ID NO: 13 |
| 238-8-LC | | E D V A T Y Y C | L Q S D S L P | Y T F G Q G T K L E I K | SEQ ID NO: 14 |
| 238-9-LC | | E D V A T Y Y C | L Q S D S L P | Y T F G Q G T K L E I K | SEQ ID NO: 15 |
| 238-10-LC | | E D V A T Y Y C | L Q S D S L P | Y T F G Q G T K L E I K | SEQ ID NO: 16 |
| 238-11-LC | | E D V A T Y Y C | L Q S D S L P | Y T F G Q G T K L E I K | SEQ ID NO: 17 |

| FIG. 2A | FIG. 2B | FIG. 2C |

| Kabat# | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | A | B | 36 | 37 | 38 | 39 | 40 | 41 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| VH7 Consensus | Q | V | Q | L | V | Q | S | G | S | E | L | K | K | P | G | A | S | V | K | V | S | C | K | A | S | G | Y | T | F | T | S | Y | A | M | N | | | W | V | R | Q | A | P |
| #111-HC | Q | V | Q | L | V | Q | S | G | P | E | L | K | K | P | G | A | S | V | K | V | S | C | K | A | S | G | Y | T | F | T | E | Y | G | M | N | | | W | V | R | Q | A | P |
| 238-HC | E | V | Q | L | V | Q | S | G | P | E | L | K | K | P | G | A | S | V | K | V | S | C | K | A | S | G | Y | T | F | T | N | Y | G | M | N | | | W | V | R | Q | A | P |
| 238-1-HC | Q | V | Q | L | V | Q | S | G | P | E | L | K | K | P | G | A | S | V | K | V | S | C | K | A | S | G | Y | T | F | T | N | Y | G | M | N | | | W | V | R | Q | A | P |
| 238-2-HC | Q | V | Q | L | V | Q | S | G | P | E | L | K | K | P | G | A | S | V | K | V | S | C | K | A | S | G | Y | T | F | T | N | Y | G | M | N | | | W | V | R | Q | A | P |
| 238-3-HC | Q | V | Q | L | V | Q | S | G | P | E | L | K | K | P | G | A | S | V | K | V | S | C | K | A | S | G | Y | T | F | T | N | Y | G | M | N | | | W | V | R | Q | A | P |
| 238-4-HC | Q | V | Q | L | V | Q | S | G | P | E | L | K | K | P | G | A | S | V | K | V | S | C | K | A | S | G | Y | T | F | T | N | Y | G | M | N | | | W | V | R | Q | A | P |
| 238-5-HC | Q | V | Q | L | V | Q | S | G | P | E | L | K | K | P | G | A | S | V | K | V | S | C | K | A | S | G | Y | T | F | T | N | Y | G | M | N | | | W | V | R | Q | A | P |
| 238-6-HC | Q | V | Q | L | V | Q | S | G | P | E | L | K | K | P | G | A | S | V | K | V | S | C | K | A | S | G | Y | T | F | T | N | Y | G | M | N | | | W | V | R | Q | A | P |
| 238-7-HC | Q | V | Q | L | V | Q | S | G | P | E | L | K | K | P | G | A | S | V | K | V | S | C | K | A | S | G | Y | T | F | T | N | Y | G | M | N | | | W | V | R | Q | A | P |
| 238-8-HC | Q | V | Q | L | V | Q | S | G | P | E | L | K | K | P | G | A | S | V | K | V | S | C | K | A | S | G | Y | T | F | T | N | Y | G | M | N | | | W | V | R | Q | A | P |
| 238-9-HC | Q | V | Q | L | V | Q | S | G | P | E | L | K | K | P | G | A | S | V | K | V | S | C | K | A | S | G | Y | T | F | T | N | Y | G | M | N | | | W | V | R | Q | A | P |
| 238-10-HC | Q | V | Q | L | V | Q | S | G | P | E | L | K | K | P | G | A | S | V | K | V | S | C | K | A | S | G | Y | T | F | T | N | Y | G | M | N | | | W | V | R | Q | A | P |
| 238-11-HC | Q | V | Q | L | V | Q | S | G | P | E | L | K | K | P | G | A | S | V | K | V | S | C | K | A | S | G | Y | T | F | T | N | Y | G | M | N | | | W | V | R | Q | A | P |

Chothia - CDR H1: D1 D2 D3 D4 D5 D6
Kabat - CDR H1: D7 D8 D9 D10
Contact - CDR H1

| Kabat# | 42 | 43 | 44 | 45 | 46 | 47 | 48 | 49 | 50 | 51 | 52 | a | b | c | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| VH7 | | | | | | | | | E1 | E2 | E3 | | | E4 | | | | | E5 | E6 | E7 | E10 | E11 | E12 | E13 | E14 | E15 | E16 | E17 | E18 | E19 | | | | | | | | | | | |
| Consensus | G | Q | G | L | E | W | M | G | W | I | N | | | T | M | T | G | N | P | T | Y | A | Q | G | F | T | G | R | F | V | F | S | L | D | T | S | V | S | T | A | Y | L |
| #111-HC | G | Q | G | L | E | W | M | G | W | I | N | | | T | Y | T | G | E | T | T | Y | A | D | D | F | K | G | R | F | V | F | S | L | D | T | S | V | S | T | A | Y | L |
| 238-HC | G | Q | G | L | E | W | M | G | W | I | N | | | T | Y | T | G | E | T | T | Y | A | D | D | P | K | G | R | F | V | P | S | L | D | T | S | V | S | T | A | Y | L |
| 238-1-HC | G | Q | G | L | E | W | M | G | W | I | N | | | T | Y | T | G | E | T | T | Y | A | D | D | P | K | G | R | F | V | P | S | L | D | T | S | V | S | T | A | Y | L |
| 238-2-HC | G | Q | G | L | E | W | M | G | W | I | N | | | T | Y | T | G | E | T | T | Y | A | D | D | P | K | G | R | F | V | P | S | L | D | T | S | V | S | T | A | Y | L |
| 238-3-HC | G | Q | G | L | E | W | M | G | W | I | N | | | T | Y | T | G | E | T | T | Y | A | D | D | P | K | G | R | F | V | P | S | L | D | T | S | V | S | T | A | Y | L |
| 238-4-HC | G | Q | G | L | E | W | M | G | W | I | N | | | T | Y | T | G | E | T | T | Y | A | D | D | P | K | G | R | F | V | P | S | L | D | T | S | V | S | T | A | Y | L |
| 238-5-HC | G | Q | G | L | E | W | M | G | W | I | N | | | T | Y | T | G | E | T | T | Y | A | D | D | P | K | G | R | F | V | P | S | L | D | T | S | V | S | T | A | Y | L |
| 238-6-HC | G | Q | G | L | E | W | M | G | W | I | N | | | T | Y | T | G | E | T | T | Y | A | D | D | P | K | G | R | F | V | P | S | L | D | T | S | V | S | T | A | Y | L |
| 238-7-HC | G | Q | G | L | E | W | M | G | W | I | N | | | T | Y | T | G | E | T | T | Y | A | D | D | P | K | G | R | F | V | P | S | L | D | T | S | V | S | T | A | Y | L |
| 238-8-HC | G | Q | G | L | E | W | M | G | W | I | N | | | T | Y | T | G | E | T | T | Y | A | D | D | P | K | G | R | F | V | P | S | L | D | T | S | V | S | T | A | Y | L |
| 238-9-HC | G | Q | G | L | E | W | M | G | W | I | N | | | T | Y | T | G | E | T | T | Y | A | D | D | P | K | G | R | F | V | P | S | L | D | T | S | V | S | T | A | Y | L |
| 238-10-HC | G | Q | G | L | E | W | M | G | W | I | N | | | T | Y | T | G | E | T | T | Y | A | D | D | P | K | G | R | F | V | P | S | L | D | T | S | V | S | T | A | Y | L |
| 238-11-HC | G | Q | G | L | E | W | M | G | W | I | N | | | T | Y | T | G | E | T | T | Y | A | D | D | P | K | G | R | F | V | P | S | L | D | T | S | V | S | T | A | Y | L |

CDR regions indicated: Kabat – CDR H2 (positions 50–65); Chothia – CDR H2 (positions 52–56); Contact – CDR H2 (positions 47–58).

FIG. 2C

| Kabat# | 81 | 82 | A | B | C | 83 | 84 | 85 | 86 | 87 | 88 | 89 | 90 | 91 | 92 | 93 | 94 | 95 | 96 | 97 | 98 | 99 | 100 | A | B | C | D | E | F | G | H | I | J | K | 101 | 102 | 103 | 104 | 105 | 106 | 107 | 108 | 109 | 110 | 111 | 112 | 113 | |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| | | | | | | | | | | | | | | | | | | | | | | | | | | | | | | | Kabat – CDR H3 | | | | | | | | | | | | | | | | |
| | | | | | | | | | | | | | | | | | | | | | | | | | | | | | | | Chothia – CDR H3 | | | | | | | | | | | | | | | | |
| | | | | | | | | | | | | | | | | | | | | | | | | | | | | | | | Contact – CDR H3 | | | | | | | | | | | | | | | | |
| | | | | | | | | | | | | | | | | | | | | | | | | F1 | F2 | F3 | F4 | F5 | F6 | | | | | | | | | | | | | | | | | | |
| VH7 Consensus | Q | I | S | S | L | K | A | E | D | T | A | V | Y | Y | C | A | R | | | | | | | | | | | | | | | | | | | W | G | Q | G | T | S | L | T | V | S | S | SEQ ID NO: 66 |
| #111-HC | Q | I | S | S | L | K | A | E | D | T | A | V | Y | Y | C | A | R | | | | | | | E | G | G | V | N | N | | | | | | | W | G | Q | G | T | L | V | T | V | S | S | SEQ ID NO: 2 |
| 238-HC | Q | I | S | S | L | K | A | E | D | T | A | V | Y | Y | C | A | R | | | | | | | E | G | G | V | N | N | | | | | | | W | G | Q | G | T | L | V | T | V | S | S | SEQ ID NO: 18 |
| 238-1-HC | Q | I | S | S | L | K | A | E | D | T | A | V | Y | Y | C | A | R | | | | | | | E | G | G | V | N | N | | | | | | | W | G | Q | G | T | L | V | T | V | S | S | SEQ ID NO: 19 |
| 238-2-HC | Q | I | S | S | L | K | A | E | D | T | A | V | Y | Y | C | A | R | | | | | | | E | G | G | V | N | N | | | | | | | W | G | Q | G | T | L | V | T | V | S | S | SEQ ID NO: 20 |
| 238-3-HC | Q | I | S | S | L | K | A | E | D | T | A | V | Y | Y | C | A | R | | | | | | | E | G | G | V | N | N | | | | | | | W | G | Q | G | T | L | V | T | V | S | S | SEQ ID NO: 21 |
| 238-4-HC | Q | I | S | S | L | K | A | E | D | T | A | V | Y | Y | C | A | R | | | | | | | E | G | G | V | N | N | | | | | | | W | G | Q | G | T | L | V | T | V | S | S | SEQ ID NO: 22 |
| 238-5-HC | Q | I | S | S | L | K | A | E | D | T | A | V | Y | Y | C | A | R | | | | | | | E | G | G | V | N | N | | | | | | | W | G | Q | G | T | L | V | T | V | S | S | SEQ ID NO: 23 |
| 238-6-HC | Q | I | S | S | L | K | A | E | D | T | A | V | Y | Y | C | A | R | | | | | | | E | G | G | V | N | N | | | | | | | W | G | Q | G | T | L | V | T | V | S | S | SEQ ID NO: 24 |
| 238-7-HC | Q | I | S | S | L | K | A | E | D | T | A | V | Y | Y | C | A | R | | | | | | | E | G | G | V | N | N | | | | | | | W | G | Q | G | T | L | V | T | V | S | S | SEQ ID NO: 25 |
| 238-8-HC | Q | I | S | S | L | K | A | E | D | T | A | V | Y | Y | C | A | R | | | | | | | E | G | G | V | A | N | | | | | | | W | G | Q | G | T | L | V | T | V | S | S | SEQ ID NO: 26 |
| 238-9-HC | Q | I | S | S | L | K | A | E | D | T | A | V | Y | Y | C | A | R | | | | | | | E | G | G | V | Q | N | | | | | | | W | G | Q | G | T | L | V | T | V | S | S | SEQ ID NO: 27 |
| 238-10-HC | Q | I | S | S | L | K | A | E | D | T | A | V | Y | Y | C | A | R | | | | | | | E | G | G | V | N | A | | | | | | | W | G | Q | G | T | L | V | T | V | S | S | SEQ ID NO: 28 |
| 238-11-HC | Q | I | S | S | L | K | A | E | D | T | A | V | Y | Y | C | A | R | | | | | | | E | G | G | V | N | Q | | | | | | | W | G | Q | G | T | L | V | T | V | S | S | SEQ ID NO: 29 |

```
ATGAAGAAGAATATTGCGTTCCTACTTGCCCTCTCTATGTTTGTCTTTTCTATAGCTACAAACGCGTATGCTGAT
ATCCAGGTGACCCAGTCTCCAGTCTCCATCTCCCTGTCTGCATCTGTAGGAGACCGCGTCACCATCACTTGCATTACC
AGCACTGATATTGATGATGATATGAACTGGTATCAGCAGAAACCAGGGAAAGTTCCTAAGCTCCTGATCTCT
GGAGGCAATACTCTTCGTCCTGGGGTCCCATCTCGGTTCAGTGGCAGTGGATCTGGGACAGATTTCACTCTC
ACCATCAGCAGCCTGCAGCCTGAAGATGTTGCAACGACAACTGTGCTGCTACTGTTGCACCATCTGTCTTCCCGCCATCT
TTTGGCCAGGGTACCAAGGTGGAGATCAAACGAACTGTGGCTGCACCATCTGTCTTCATCTTCCCGCCATCT
GATGAGCAGTTGAAATCTGGAACTGCCTCTGTTGTGTGCCTGCTGAATAACTTCTATCCCAGAGAGGCCAAA
GTACAGTGGAAGGTGGATAACGCCCTCCAATCGGGTAACTCCCAGGAGAGTGTCACAGAGCAGGACAGCAAG
GACAGCACCTACAGCCTCAGCAGCACCCTGACGCTGAGCAAAGCAGACTACGAGAAACACAAAGTCTACGCC
TGCGAAGTCACCCATCAGGGCCTGAGCTCGCCCGTCACAAAGAGCTTCAACAGGGGAGAGTGTTAA
```

FIG. 3

```
DIQVTQSPSSLSASVGDRVTITCITSTDIDDDMNWYQQKPGKVPKLLISGGNTLRPGVPSRFSGSGSGTDFT
LTISSLQPEDVATYYCLQSDSLPYTFGQGTKVEIKRTVAAPSVFIFPPSDEQLKSGTASVVCLLNNFYPREA
KVQWKVDNALQSGNSQESVTEQDSKDSTYSLSSTLTLSKADYEKHKVYACEVTHQGLSSPVTKSFNRGEC
(SEQ ID NO: 47)

FR1-LC:   DIQVTQSPSSLSASVGDRVTITC      (SEQ ID NO: 48)
FR2-LC:   WYQQKPGKVPKLLIS   (SEQ ID NO: 49)
FR3-LC:   GVPSRFSGSGSGTDFTLTISSLQPEDVATYYC   (SEQ ID NO: 50)
FR4-LC:   FGQGTKVEIK   (SEQ ID NO: 51)
HVR1-LC:  ITSTDIDDDMN   (SEQ ID NO: 30)
HVR2-LC:  GGNTLRP   (SEQ ID NO: 35)
HVR3-LC:  LQSDSLPYT   (SEQ ID NO: 38)
CL1:
RTVAAPSVFIFPPSDEQLKSGTASVVCLLNNFYPREAKVQWKVDNALQSGNSQESVTEQDSKDSTYSLSSTL
TLSKADYEKHKVYACEVTHQGLSSPVTKSFNRGEC   (SEQ ID NO: 52)
```

FIG. 4

ATGAAAAAGAATATCGCATTTCTTCTTGCATCTATGTTCGTTTTTTCTATTGCTACAAACGCTACGCTCAG
GTCCAGCTGGTGCAATCTGGACCTGAGTTGAAGAAGCCTGGGGCCTCAGTGAAGGTTTCCTGCAAGGCTTCT
GGATACACCTTCACTAACTATGGAATGAACTGGGTGCGCCAAGCCCCTGGACAAGGGCTTGAGTGGATGGGA
TGGATTAACACCTACACTGGAGAGACAACATATGCTGATGACTTCAAGGGACGGTTTGTCTTCTCCTTGGAC
ACCTCTGTAACAGCCTACCTGCAGATCTGCAGCCTGAAGGCTGAGGACACTGCCGTGTATTACTGTGAG
CGCGAGGGGGGGGTTAATAACTGCACCCTCTGGGGCCAGGGCACCCTGGTCACCGTCTCCTCAGCAGCCTCCACCAAGGGCCCA
TCGGTCTTCCCCCTGGCACCCTCCTCCAAGAGCACCTCTGGGGGCACAGCGGCCCTGGGCTGCCTGGTCAAG
GACTACTTCCCCGAACCGGTGACGGTGTCGTGGAACTCAGGCGCCCTGACCAGCGGCGTGCACACCTTCCCG
GCTGTCCTACAGTCCTCAGGACTCTACTCCCTCAGCAGCGTGGTGACCGTGCCCTCCAGCAGCTTGGGCACC
CAGACCTACATCTGCAACGTGAATCACAAGCCCAGCAACACCAAGGTGGACAAGAAAGTTGAGCCCAAATCT
TGTGACAAAACTCACACATAA

*FIG. 5*

QVQLVQSGPELKKPGASVKVSCKAS*GYTFTNYGMN*WVRQAPGQGLEWMG*WINTYTGETTYADDFKG*RFVFSL
DTSVSTAYLQISSLKAEDTAVYYCER*EGGVNN*WGQGTLVTVSSAAATKGPSVFPLAPSSKSTSGGTAALGCLV
KDYFPEPVTVSWNSGALTSGVHTFPAVLQSSGLYSLSSVVTVPSSSLGTQTYICNVNHKPSNTKVDKKVEPK
SCDKTHT (SEQ ID NO: 54)

FR1-HC:  QVQLVQSGPELKKPGASVKVSCKAS   (SEQ ID NO: 55)
FR2-HC:  WVRQAPGQGLEWMG    (SEQ ID NO: 56)
FR3-HC:  RFVFSLDTSVSTAYLQISSLKAEDTAVYYCER   (SEQ ID NO: 57)
FR4-HC:  WGQGTLVTVSS    (SEQ ID NO: 58)
HVR1-HC: *GYTFTNYGMN*   (SEQ ID NO: 39)
HVR2-HC: *WINTYTGETTYADDFKG*   (SEQ ID NO: 40)
HVR3-HC: *EGGVNN*   (SEQ ID NO: 41)
CH1:
ASTKGPSVFPLAPSSKSTSGGTAALGCLVKDYFPEPVTVSWNSGALTSGVHTFPAVLQSSGLYSLSSVVTVP
SSSLGTQTYICNVNHKPSNTKVDKKVEPKSCDKTHT   (SEQ ID NO: 59)

*FIG. 6*

ATGAAGAAGAGAATATTGCGTTCCTACTTGCCTCTGTTTGTCTTTTCTATAGCTACAAACGCGTATGCTGAT
ATCCAGGTGACCCAGTCTCCATCTCCCCTGTCTGCATCTGTAGGAGACCGCGTCACCATCACTTGCATTACC
AGCACTGATATTGATGATGATATGAACTGGTATCAGCAGAAACCAGGGAAAGTTCCTAAGCTCCTGATCTCT
GGAGGCAATACTCTCGTCCTGGGGTCCTCAGGGTTCAGTGGCAGTGGATCTGGGACAGATTTCACTCTC
ACCATCAGCAGCCTGCAGCCTGAAGATGTTGCAACTTATTACTGTTTGCAACATCTGTCTTCATCTTCCGCCATCT
TTTGGCCAGGGTACCAAGGTGGAGATCAAACGAACTGTGCTGCACCATCTGTCTTCATCTTCCCAGAGAGGCCAAA
GATGAGCAGTTGAAATCTGGAACTGCTTCTGTTGTGTGCCTGCTGAATAACTTCTATCCCAGAGAGACCAAG
GTACAGTGGAAGGTGGATAACGCCCTCCAATCGGGTAACTCCCAGGAGAGTGTCACAGAGCAGGACAGCAAG
GACAGCACCTACAGCCTCAGCAGCACCCTGAGCAAAGCAGACTACGAGAAACACAAAGTCTACGCC
TGCGAAGTCACCCATCAGGGCCTGAGCTCGCCCGTCACAAAGAGCTTCAACAGGGGAGAGTGTTAA

FIG. 7

DIQVTQSPSSLSASVGDRVTITC*ITSTDIDDDMN*WYQQKPGKVPKLLIS*GGNTLRP*GVPSRFSGSGSGTDFT
LTISSLQPEDVATYYC*LQSDSLPYT*FGQGTKVEIKRTVAAPSVFIFPPSDEQLKSGTASVVCLLNNFYPREA
KVQWKVDNALQSGNSQESVTEQDSKDSTYSLSSTLTLSKADYEKHKVYACEVTHQGLSSPVTKSFNRGEC
(SEQ ID NO: 61)

FR1-LC:   DIQVTQSPSSLSASVGDRVTITC    (SEQ ID NO: 48)
FR2-LC:   WYQQKPGKVPKLLIS            (SEQ ID NO: 49)
FR3-LC:   GVPSRFSGSGSGTDFTLTISSLQPEDVATYYC   (SEQ ID NO: 50)
FR4-LC:   FGQGTKVEIK                 (SEQ ID NO: 51)
HVR1-LC:  *ITSTDIDDDMN*              (SEQ ID NO: 30)
HVR2-LC:  *GGNTLRP*                  (SEQ ID NO: 35)
HVR3-LC:  *LQSDSLPYT*                (SEQ ID NO: 38)
CL1:      RTVAAPSVFIFPPSDEQLKSGTASVVCLLNNFYPREAKVQWKVDNALQSGNSQESVTEQDSKDSTYSLSSTL
          TLSKADYEKHKVYACEVTHQGLSSPVTKSFNRGEC    (SEQ ID NO: 52)

FIG. 8

```
ATGAAAAAGAATATCGCATTTCTTCTGCAGTTGCATCTATGTTCGTTTTTCTATTGCTACAAAACGCGTACGCTGAA
GTCCAGCTGGTGCAATCTGGGCCTGAGTTGAAGAAGCCTGGGGCTTCAGTGAAGGTTTCCTGCAAGGCTTCT
GGATACACCTTCACTAACTATGGAATGAACTGGGTGCGCCAAGCCCCTGGACAAGGGCTTGAGTGATGGGA
TGGATTAACACCTACACTGGAGAGACAACATATGCTGATGACTTCAAGGGACGGTTTGTCTTCTCCTTGGAC
ACCTCTGTCAGCACGGCATATCTGCAGATCAGCAGCCTGAAGGCTGAGGACACTGCCGTGTATTACTGTGAG
CGCGAGGGGGGTGTAAATAACTGGGGCCAAGGGACCACCTTGGTCACCGTCTCCTCAGCCTCCACCAAGGGCCCA
TCGGTCTTCCCCCTGGCACCCTCCAGCACCAAGAGCACTTCTGGGGGCACAGCGGCCCTGGGCTGCCTGGTCAAG
GACTACTTCCCCGAACCGGTGACGGTGTCGTGGAACTCAGGCGCCCTGACCAGCGGCGTGCACACCTTCCCG
GCTGTCCTACAGTCCTCAGGACTCTACTCCCTCAGCAGCGTGGTGACCGTGCCCTCCAGCAGCTTGGGCACC
CAGACCTACATCTGCAACGTGAATCACAAGCCCAGCAACACCAAGGTGGACAAGAAAGTTGAGCCCAAATCT
TGTGACAAAACTCACACATAA
```

FIG. 9

```
EVQLVQSGPELKKPGASVKVSCKASGYTFTNYGMNWVRQAPGQGLEWMGWINTYTGETTYADDFKGRFVFSL
DTSVSTAYLQISSLKAEDTAVYYCEREGGVNNWGQGTLVTVSSASTKGPSVFPLAPSSKSTSGGTAALGCLV
KDYFPEPVTVSWNSGALTSGVHTFPAVLQSSGLYSLSSVVTVPSSSLGTQTYICNVNHKPSNTKVDKKVEPK
SCDKTHT    (SEQ ID NO: 63)

FR1-HC:  EVQLVQSGPELKKPGASVKVSCKAS   (SEQ ID NO: 64)
FR2-HC:  WVRQAPGQGLEWMG    (SEQ ID NO: 56)
FR3-HC:  RFVFSLDTSVSTAYLQISSLKAEDTAVYYCER   (SEQ ID NO: 57)
FR4-HC:  WGQGTLVTVSS    (SEQ ID NO: 58)
HVR1-HC: GYTFTNYGMN    (SEQ ID NO: 39)
HVR2-HC: WINTYTGETTYADDFKG   (SEQ ID NO: 40)
HVR3-HC: EGGVNN    (SEQ ID NO: 41)
CH1:
ASTKGPSVFPLAPSSKSTSGGTAALGCLVKDYFPEPVTVSWNSGALTSGVHTFPAVLQSSGLYSLSSVVTVP
SSSLGTQTYICNVNHKPSNTKVDKKVEPKSCDKTHT    (SEQ ID NO: 59)
```

FIG. 10

SEQUENCE LISTING

<160> NUMBER OF SEQ ID NOS: 74

<210> SEQ ID NO 1
<211> LENGTH: 107
<212> TYPE: PRT
<213> ORGANISM: Artificial sequence
<220> FEATURE:
<223> OTHER INFORMATION: Variable Light Chain Domain of Humanized Clone
      #111

<400> SEQUENCE: 1

Asp Ile Gln Val Thr Gln Ser Pro Ser Ser Leu Ser Ala Ser Val
 1               5                  10                  15

Gly Asp Arg Val Thr Ile Thr Cys Ile Thr Ser Thr Asp Ile Asp
                20                  25                  30

Asp Asp Met Asn Trp Tyr Gln Gln Lys Pro Gly Lys Val Pro Lys
                35                  40                  45

Leu Leu Ile Ser Gly Gly Asn Thr Leu Arg Pro Gly Val Pro Ser
                50                  55                  60

Arg Phe Ser Gly Ser Gly Ser Gly Thr Asp Phe Thr Leu Thr Ile
                65                  70                  75

Ser Ser Leu Gln Pro Glu Asp Val Ala Thr Tyr Tyr Cys Leu Gln
                80                  85                  90

Ser Asp Ser Leu Pro Tyr Thr Phe Gly Gln Gly Thr Lys Leu Glu
                95                  100                 105

Ile Lys

<210> SEQ ID NO 2
<211> LENGTH: 115
<212> TYPE: PRT
<213> ORGANISM: Artificial sequence
<220> FEATURE:
<223> OTHER INFORMATION: Variable Heavy Chain Domain of Humanized Clone
      #111

<400> SEQUENCE: 2

Gln Val Gln Leu Val Gln Ser Gly Pro Glu Leu Lys Lys Pro Gly
 1               5                  10                  15

Ala Ser Val Lys Val Ser Cys Lys Ala Ser Gly Tyr Thr Phe Thr
                20                  25                  30

Asn Tyr Gly Met Asn Trp Val Arg Gln Ala Pro Gly Gln Gly Leu
                35                  40                  45

Glu Trp Met Gly Trp Ile Asn Thr Tyr Thr Gly Glu Thr Thr Tyr
            50                  55                  60

Ala Asp Asp Phe Lys Gly Arg Phe Val Phe Ser Leu Asp Thr Ser
        65                  70                  75

Val Ser Thr Ala Tyr Leu Gln Ile Ser Ser Leu Lys Ala Glu Asp
    80                  85                  90

Thr Ala Val Tyr Tyr Cys Glu Arg Glu Gly Gly Val Asn Asn Trp
            95                  100                 105

Gly Gln Gly Thr Leu Val Thr Val Ser Ser
                110                 115

<210> SEQ ID NO 3
<211> LENGTH: 31
<212> TYPE: PRT
<213> ORGANISM: Artificial sequence
<220> FEATURE:
<223> OTHER INFORMATION: Sequence is synthesized (FR3 from VH acceptor
      human framework)

<400> SEQUENCE: 3

Arg Phe Val Phe Ser Leu Asp Thr Ser Val Ser Thr Ala Tyr Leu
 1               5                   10                  15

Gln Ile Ser Ser Leu Lys Ala Glu Asp Thr Ala Val Tyr Tyr Cys
            20                  25                  30

Ser

<210> SEQ ID NO 4
<211> LENGTH: 32
<212> TYPE: PRT
<213> ORGANISM: Artificial sequence
<220> FEATURE:
<223> OTHER INFORMATION: Sequence is synthesized (FR3 from VH acceptor
      human framework)

<400> SEQUENCE: 4

Arg Phe Val Phe Ser Leu Asp Thr Ser Val Ser Thr Ala Tyr Leu
 1               5                   10                  15

Gln Ile Ser Ser Leu Lys Ala Glu Asp Thr Ala Val Tyr Tyr Cys
            20                  25                  30

Ser Arg

<210> SEQ ID NO 5
<211> LENGTH: 10
<212> TYPE: PRT
<213> ORGANISM: Artificial sequence
<220> FEATURE:
<223> OTHER INFORMATION: Sequence is synthesized (FR4 from VL acceptor
      human framework)

<400> SEQUENCE: 5

Phe Gly Gln Gly Thr Lys Val Glu Ile Lys
                5                   10

<210> SEQ ID NO 6
<211> LENGTH: 107
<212> TYPE: PRT
<213> ORGANISM: Artificial sequence
<220> FEATURE:
<223> OTHER INFORMATION: Variable light chain domain of modified
      humanized anti-Factor D Fab 238

<400> SEQUENCE: 6

Asp Ile Gln Val Thr Gln Ser Pro Ser Ser Leu Ser Ala Ser Val

```
                1               5                  10                  15
Gly Asp Arg Val Thr Ile Thr Cys Ile Thr Ser Thr Asp Ile Asp
                20                  25                  30

Asp Asp Met Asn Trp Tyr Gln Gln Lys Pro Gly Lys Val Pro Lys
                35                  40                  45

Leu Leu Ile Ser Gly Gly Asn Thr Leu Arg Pro Gly Val Pro Ser
                50                  55                  60

Arg Phe Ser Gly Ser Gly Ser Gly Thr Asp Phe Thr Leu Thr Ile
                65                  70                  75

Ser Ser Leu Gln Pro Glu Asp Val Ala Thr Tyr Tyr Cys Leu Gln
                80                  85                  90

Ser Asp Ser Leu Pro Tyr Thr Phe Gly Gln Gly Thr Lys Val Glu
                95                  100                 105

Ile Lys

<210> SEQ ID NO 7
<211> LENGTH: 107
<212> TYPE: PRT
<213> ORGANISM: Artificial sequence
<220> FEATURE:
<223> OTHER INFORMATION: Variable light chain domain of modified
      humanized anti-factor D Fab 238-1

<400> SEQUENCE: 7

Asp Ile Gln Val Thr Gln Ser Pro Ser Ser Leu Ser Ala Ser Val
 1              5                  10                  15

Gly Asp Arg Val Thr Ile Thr Cys Ile Thr Ser Thr Asp Ile Asp
                20                  25                  30

Asp Asp Met Asn Trp Tyr Gln Gln Lys Pro Gly Lys Val Pro Lys
                35                  40                  45

Leu Leu Ile Ser Gly Gly Asn Thr Leu Arg Pro Gly Val Pro Ser
                50                  55                  60

Arg Phe Ser Gly Ser Gly Ser Gly Thr Asp Phe Thr Leu Thr Ile
                65                  70                  75

Ser Ser Leu Gln Pro Glu Asp Val Ala Thr Tyr Tyr Cys Leu Gln
                80                  85                  90

Ser Asp Ser Leu Pro Tyr Thr Phe Gly Gln Gly Thr Lys Val Glu
                95                  100                 105

Ile Lys

<210> SEQ ID NO 8
<211> LENGTH: 107
<212> TYPE: PRT
<213> ORGANISM: Artificial sequence
<220> FEATURE:
<223> OTHER INFORMATION: Variable light chain domain of modified
      humanized anti-Factor D Fab 238-2

<400> SEQUENCE: 8

Asp Ile Gln Val Thr Gln Ser Pro Ser Ser Leu Ser Ala Ser Val
 1              5                  10                  15

Gly Asp Arg Val Thr Ile Thr Cys Ile Thr Ser Thr Asp Ile Asp
                20                  25                  30

Asp Asp Leu Asn Trp Tyr Gln Gln Lys Pro Gly Lys Val Pro Lys
                35                  40                  45

Leu Leu Ile Ser Gly Gly Asn Thr Leu Arg Pro Gly Val Pro Ser
                50                  55                  60

Arg Phe Ser Gly Ser Gly Ser Gly Thr Asp Phe Thr Leu Thr Ile
```

```
                65                  70                  75
Ser Ser Leu Gln Pro Glu Asp Val Ala Thr Tyr Tyr Cys Leu Gln
                80                  85                  90

Ser Asp Ser Leu Pro Tyr Thr Phe Gly Gln Gly Thr Lys Leu Glu
                95                 100                 105

Ile Lys

<210> SEQ ID NO 9
<211> LENGTH: 107
<212> TYPE: PRT
<213> ORGANISM: Artificial sequence
<220> FEATURE:
<223> OTHER INFORMATION: Variable light chain domain of modified
      humanized anti-Factor D Fab 238-3

<400> SEQUENCE: 9

Asp Ile Gln Val Thr Gln Ser Pro Ser Ser Leu Ser Ala Ser Val
 1               5                  10                  15

Gly Asp Arg Val Thr Ile Thr Cys Ile Thr Ser Thr Asp Ile Asp
                20                  25                  30

Asp Asp Ile Asn Trp Tyr Gln Gln Lys Pro Gly Lys Val Pro Lys
                35                  40                  45

Leu Leu Ile Ser Gly Gly Asn Thr Leu Arg Pro Gly Val Pro Ser
                50                  55                  60

Arg Phe Ser Gly Ser Gly Ser Gly Thr Asp Phe Thr Leu Thr Ile
                65                  70                  75

Ser Ser Leu Gln Pro Glu Asp Val Ala Thr Tyr Tyr Cys Leu Gln
                80                  85                  90

Ser Asp Ser Leu Pro Tyr Thr Phe Gly Gln Gly Thr Lys Leu Glu
                95                 100                 105

Ile Lys

<210> SEQ ID NO 10
<211> LENGTH: 107
<212> TYPE: PRT
<213> ORGANISM: Artificial sequence
<220> FEATURE:
<223> OTHER INFORMATION: Variable light chain domain of modified
      humanized anti-Factor D Fab 238-4

<400> SEQUENCE: 10

Asp Ile Gln Val Thr Gln Ser Pro Ser Ser Leu Ser Ala Ser Val
 1               5                  10                  15

Gly Asp Arg Val Thr Ile Thr Cys Ile Thr Ser Thr Asp Ile Asp
                20                  25                  30

Asp Asp Met Ala Trp Tyr Gln Gln Lys Pro Gly Lys Val Pro Lys
                35                  40                  45

Leu Leu Ile Ser Gly Gly Asn Thr Leu Arg Pro Gly Val Pro Ser
                50                  55                  60

Arg Phe Ser Gly Ser Gly Ser Gly Thr Asp Phe Thr Leu Thr Ile
                65                  70                  75

Ser Ser Leu Gln Pro Glu Asp Val Ala Thr Tyr Tyr Cys Leu Gln
                80                  85                  90

Ser Asp Ser Leu Pro Tyr Thr Phe Gly Gln Gly Thr Lys Leu Glu
                95                 100                 105

Ile Lys

<210> SEQ ID NO 11
```

```
<211> LENGTH: 107
<212> TYPE: PRT
<213> ORGANISM: Artificial sequence
<220> FEATURE:
<223> OTHER INFORMATION: Variable light chain domain of modified
      humanized anti-Factor D Fab 238-5

<400> SEQUENCE: 11

Asp Ile Gln Val Thr Gln Ser Pro Ser Ser Leu Ser Ala Ser Val
 1               5                  10                  15

Gly Asp Arg Val Thr Ile Thr Cys Ile Thr Ser Thr Asp Ile Asp
                20                  25                  30

Asp Asp Met Gln Trp Tyr Gln Gln Lys Pro Gly Lys Val Pro Lys
                35                  40                  45

Leu Leu Ile Ser Gly Gly Asn Thr Leu Arg Pro Gly Val Pro Ser
                50                  55                  60

Arg Phe Ser Gly Ser Gly Ser Gly Thr Asp Phe Thr Leu Thr Ile
                65                  70                  75

Ser Ser Leu Gln Pro Glu Asp Val Ala Thr Tyr Tyr Cys Leu Gln
                80                  85                  90

Ser Asp Ser Leu Pro Tyr Thr Phe Gly Gln Gly Thr Lys Leu Glu
                95                 100                 105

Ile Lys

<210> SEQ ID NO 12
<211> LENGTH: 107
<212> TYPE: PRT
<213> ORGANISM: Artificial sequence
<220> FEATURE:
<223> OTHER INFORMATION: Variable light chain domain of modified
      humanized anti-Factor D Fab 238-6

<400> SEQUENCE: 12

Asp Ile Gln Val Thr Gln Ser Pro Ser Ser Leu Ser Ala Ser Val
 1               5                  10                  15

Gly Asp Arg Val Thr Ile Thr Cys Ile Thr Ser Thr Asp Ile Asp
                20                  25                  30

Asp Asp Met Asn Trp Tyr Gln Gln Lys Pro Gly Lys Val Pro Lys
                35                  40                  45

Leu Leu Ile Ser Gly Gly Ser Thr Leu Arg Pro Gly Val Pro Ser
                50                  55                  60

Arg Phe Ser Gly Ser Gly Ser Gly Thr Asp Phe Thr Leu Thr Ile
                65                  70                  75

Ser Ser Leu Gln Pro Glu Asp Val Ala Thr Tyr Tyr Cys Leu Gln
                80                  85                  90

Ser Asp Ser Leu Pro Tyr Thr Phe Gly Gln Gly Thr Lys Leu Glu
                95                 100                 105

Ile Lys

<210> SEQ ID NO 13
<211> LENGTH: 107
<212> TYPE: PRT
<213> ORGANISM: Artificial sequence
<220> FEATURE:
<223> OTHER INFORMATION: Variable light chain domain of modified
      humanized anti-Factor D Fab 238-7

<400> SEQUENCE: 13

Asp Ile Gln Val Thr Gln Ser Pro Ser Ser Leu Ser Ala Ser Val
 1               5                  10                  15
```

```
Gly Asp Arg Val Thr Ile Thr Cys Ile Thr Ser Thr Asp Ile Asp
            20                  25                  30

Asp Asp Met Asn Trp Tyr Gln Gln Lys Pro Gly Lys Val Pro Lys
            35                  40                  45

Leu Leu Ile Ser Gly Gly Ala Thr Leu Arg Pro Gly Val Pro Ser
            50                  55                  60

Arg Phe Ser Gly Ser Gly Ser Gly Thr Asp Phe Thr Leu Thr Ile
            65                  70                  75

Ser Ser Leu Gln Pro Glu Asp Val Ala Thr Tyr Tyr Cys Leu Gln
            80                  85                  90

Ser Asp Ser Leu Pro Tyr Thr Phe Gly Gln Gly Thr Lys Leu Glu
            95                  100                 105

Ile Lys

<210> SEQ ID NO 14
<211> LENGTH: 107
<212> TYPE: PRT
<213> ORGANISM: Artificial sequence
<220> FEATURE:
<223> OTHER INFORMATION: Variable light chain domain of modified
      humanized anti-Factor D Fab 238-8

<400> SEQUENCE: 14

Asp Ile Gln Val Thr Gln Ser Pro Ser Ser Leu Ser Ala Ser Val
 1               5                  10                  15

Gly Asp Arg Val Thr Ile Thr Cys Ile Thr Ser Thr Asp Ile Asp
            20                  25                  30

Asp Asp Met Asn Trp Tyr Gln Gln Lys Pro Gly Lys Val Pro Lys
            35                  40                  45

Leu Leu Ile Ser Gly Gly Asn Thr Leu Arg Pro Gly Val Pro Ser
            50                  55                  60

Arg Phe Ser Gly Ser Gly Ser Gly Thr Asp Phe Thr Leu Thr Ile
            65                  70                  75

Ser Ser Leu Gln Pro Glu Asp Val Ala Thr Tyr Tyr Cys Leu Gln
            80                  85                  90

Ser Asp Ser Leu Pro Tyr Thr Phe Gly Gln Gly Thr Lys Leu Glu
            95                  100                 105

Ile Lys

<210> SEQ ID NO 15
<211> LENGTH: 107
<212> TYPE: PRT
<213> ORGANISM: Artificial sequence
<220> FEATURE:
<223> OTHER INFORMATION: Variable light chain domain of modified
      humanized anti-Factor D Fab 238-9

<400> SEQUENCE: 15

Asp Ile Gln Val Thr Gln Ser Pro Ser Ser Leu Ser Ala Ser Val
 1               5                  10                  15

Gly Asp Arg Val Thr Ile Thr Cys Ile Thr Ser Thr Asp Ile Asp
            20                  25                  30

Asp Asp Met Asn Trp Tyr Gln Gln Lys Pro Gly Lys Val Pro Lys
            35                  40                  45

Leu Leu Ile Ser Gly Gly Asn Thr Leu Arg Pro Gly Val Pro Ser
            50                  55                  60

Arg Phe Ser Gly Ser Gly Ser Gly Thr Asp Phe Thr Leu Thr Ile
            65                  70                  75
```

Ser Ser Leu Gln Pro Glu Asp Val Ala Thr Tyr Tyr Cys Leu Gln
            80                  85                  90

Ser Asp Ser Leu Pro Tyr Thr Phe Gly Gln Gly Thr Lys Leu Glu
            95                  100                 105

Ile Lys

<210> SEQ ID NO 16
<211> LENGTH: 107
<212> TYPE: PRT
<213> ORGANISM: Artificial sequence
<220> FEATURE:
<223> OTHER INFORMATION: Variable light chain domain of modified
      humanized anti-Factor D Fab 238-10

<400> SEQUENCE: 16

Asp Ile Gln Val Thr Gln Ser Pro Ser Ser Leu Ser Ala Ser Val
 1               5                  10                  15

Gly Asp Arg Val Thr Ile Thr Cys Ile Thr Ser Thr Asp Ile Asp
                20                  25                  30

Asp Asp Met Asn Trp Tyr Gln Gln Lys Pro Gly Lys Val Pro Lys
                35                  40                  45

Leu Leu Ile Ser Gly Gly Asn Thr Leu Arg Pro Gly Val Pro Ser
            50                  55                  60

Arg Phe Ser Gly Ser Gly Ser Gly Thr Asp Phe Thr Leu Thr Ile
 65                  70                  75

Ser Ser Leu Gln Pro Glu Asp Val Ala Thr Tyr Tyr Cys Leu Gln
            80                  85                  90

Ser Asp Ser Leu Pro Tyr Thr Phe Gly Gln Gly Thr Lys Leu Glu
            95                  100                 105

Ile Lys

<210> SEQ ID NO 17
<211> LENGTH: 107
<212> TYPE: PRT
<213> ORGANISM: Artificial sequence
<220> FEATURE:
<223> OTHER INFORMATION: Variable light chain domain of modified
      humanized anti-Factor D Fab 238-11

<400> SEQUENCE: 17

Asp Ile Gln Val Thr Gln Ser Pro Ser Ser Leu Ser Ala Ser Val
 1               5                  10                  15

Gly Asp Arg Val Thr Ile Thr Cys Ile Thr Ser Thr Asp Ile Asp
                20                  25                  30

Asp Asp Met Asn Trp Tyr Gln Gln Lys Pro Gly Lys Val Pro Lys
                35                  40                  45

Leu Leu Ile Ser Gly Gly Asn Thr Leu Arg Pro Gly Val Pro Ser
            50                  55                  60

Arg Phe Ser Gly Ser Gly Ser Gly Thr Asp Phe Thr Leu Thr Ile
 65                  70                  75

Ser Ser Leu Gln Pro Glu Asp Val Ala Thr Tyr Tyr Cys Leu Gln
            80                  85                  90

Ser Asp Ser Leu Pro Tyr Thr Phe Gly Gln Gly Thr Lys Leu Glu
            95                  100                 105

Ile Lys

<210> SEQ ID NO 18
<211> LENGTH: 115
<212> TYPE: PRT

```
<213> ORGANISM: Artificial sequence
<220> FEATURE:
<223> OTHER INFORMATION: Variable heavy chain domain of modified
      humanized anti-Factor D Fab 238

<400> SEQUENCE: 18

Gln Val Gln Leu Val Gln Ser Gly Pro Glu Leu Lys Lys Pro Gly
 1               5                  10                  15

Ala Ser Val Lys Val Ser Cys Lys Ala Ser Gly Tyr Thr Phe Thr
                20                  25                  30

Asn Tyr Gly Met Asn Trp Val Arg Gln Ala Pro Gly Gln Gly Leu
                35                  40                  45

Glu Trp Met Gly Trp Ile Asn Thr Tyr Thr Gly Glu Thr Thr Tyr
                50                  55                  60

Ala Asp Asp Phe Lys Gly Arg Phe Val Phe Ser Leu Asp Thr Ser
                65                  70                  75

Val Ser Thr Ala Tyr Leu Gln Ile Ser Ser Leu Lys Ala Glu Asp
                80                  85                  90

Thr Ala Val Tyr Tyr Cys Glu Arg Glu Gly Gly Val Asn Asn Trp
                95                  100                 105

Gly Gln Gly Thr Leu Val Thr Val Ser Ser
                110                 115

<210> SEQ ID NO 19
<211> LENGTH: 115
<212> TYPE: PRT
<213> ORGANISM: Artificial sequence
<220> FEATURE:
<223> OTHER INFORMATION: Variable heavy chain domain of modified
      humanized anti-Factor D Fab 238-1

<400> SEQUENCE: 19

Glu Val Gln Leu Val Gln Ser Gly Pro Glu Leu Lys Lys Pro Gly
 1               5                  10                  15

Ala Ser Val Lys Val Ser Cys Lys Ala Ser Gly Tyr Thr Phe Thr
                20                  25                  30

Asn Tyr Gly Met Asn Trp Val Arg Gln Ala Pro Gly Gln Gly Leu
                35                  40                  45

Glu Trp Met Gly Trp Ile Asn Thr Tyr Thr Gly Glu Thr Thr Tyr
                50                  55                  60

Ala Asp Asp Phe Lys Gly Arg Phe Val Phe Ser Leu Asp Thr Ser
                65                  70                  75

Val Ser Thr Ala Tyr Leu Gln Ile Ser Ser Leu Lys Ala Glu Asp
                80                  85                  90

Thr Ala Val Tyr Tyr Cys Glu Arg Glu Gly Gly Val Asn Asn Trp
                95                  100                 105

Gly Gln Gly Thr Leu Val Thr Val Ser Ser
                110                 115

<210> SEQ ID NO 20
<211> LENGTH: 115
<212> TYPE: PRT
<213> ORGANISM: Artificial sequence
<220> FEATURE:
<223> OTHER INFORMATION: Variable heavy chain domain of modified
      humanized anti-Factor D Fab 238-2

<400> SEQUENCE: 20

Gln Val Gln Leu Val Gln Ser Gly Pro Glu Leu Lys Lys Pro Gly
 1               5                  10                  15
```

```
Ala Ser Val Lys Val Ser Cys Lys Ala Ser Gly Tyr Thr Phe Thr
             20                  25                  30

Asn Tyr Gly Met Asn Trp Val Arg Gln Ala Pro Gly Gln Gly Leu
         35                  40                  45

Glu Trp Met Gly Trp Ile Asn Thr Tyr Thr Gly Glu Thr Thr Tyr
     50                  55                  60

Ala Asp Asp Phe Lys Gly Arg Phe Val Phe Ser Leu Asp Thr Ser
 65                  70                  75

Val Ser Thr Ala Tyr Leu Gln Ile Ser Ser Leu Lys Ala Glu Asp
         80                  85                  90

Thr Ala Val Tyr Tyr Cys Glu Arg Glu Gly Gly Val Asn Asn Trp
             95                 100                 105

Gly Gln Gly Thr Leu Val Thr Val Ser Ser
                110                 115

<210> SEQ ID NO 21
<211> LENGTH: 115
<212> TYPE: PRT
<213> ORGANISM: Artificial sequence
<220> FEATURE:
<223> OTHER INFORMATION: Variable heavy chain domain of modified
      humanized anti-Factor D Fab 238-3

<400> SEQUENCE: 21

Gln Val Gln Leu Val Gln Ser Gly Pro Glu Leu Lys Lys Pro Gly
 1               5                  10                  15

Ala Ser Val Lys Val Ser Cys Lys Ala Ser Gly Tyr Thr Phe Thr
             20                  25                  30

Asn Tyr Gly Met Asn Trp Val Arg Gln Ala Pro Gly Gln Gly Leu
         35                  40                  45

Glu Trp Met Gly Trp Ile Asn Thr Tyr Thr Gly Glu Thr Thr Tyr
     50                  55                  60

Ala Asp Asp Phe Lys Gly Arg Phe Val Phe Ser Leu Asp Thr Ser
 65                  70                  75

Val Ser Thr Ala Tyr Leu Gln Ile Ser Ser Leu Lys Ala Glu Asp
         80                  85                  90

Thr Ala Val Tyr Tyr Cys Glu Arg Glu Gly Gly Val Asn Asn Trp
             95                 100                 105

Gly Gln Gly Thr Leu Val Thr Val Ser Ser
                110                 115

<210> SEQ ID NO 22
<211> LENGTH: 115
<212> TYPE: PRT
<213> ORGANISM: Artificial sequence
<220> FEATURE:
<223> OTHER INFORMATION: Variable heavy chain domain of modified
      humanized anti-Factor D FAB 238-4

<400> SEQUENCE: 22

Gln Val Gln Leu Val Gln Ser Gly Pro Glu Leu Lys Lys Pro Gly
 1               5                  10                  15

Ala Ser Val Lys Val Ser Cys Lys Ala Ser Gly Tyr Thr Phe Thr
             20                  25                  30

Asn Tyr Gly Met Asn Trp Val Arg Gln Ala Pro Gly Gln Gly Leu
         35                  40                  45

Glu Trp Met Gly Trp Ile Asn Thr Tyr Thr Gly Glu Thr Thr Tyr
     50                  55                  60

Ala Asp Asp Phe Lys Gly Arg Phe Val Phe Ser Leu Asp Thr Ser
 65                  70                  75
```

```
                     65                  70                  75
Val Ser Thr Ala Tyr Leu Gln Ile Ser Ser Leu Lys Ala Glu Asp
             80                  85                  90

Thr Ala Val Tyr Tyr Cys Glu Arg Glu Gly Gly Val Asn Asn Trp
                 95                 100                 105

Gly Gln Gly Thr Leu Val Thr Val Ser Ser
                110                 115

<210> SEQ ID NO 23
<211> LENGTH: 115
<212> TYPE: PRT
<213> ORGANISM: Artificial sequence
<220> FEATURE:
<223> OTHER INFORMATION: Variable heavy chain domain of modified
      humanized anti-Factor D Fab 238-5

<400> SEQUENCE: 23

Gln Val Gln Leu Val Gln Ser Gly Pro Glu Leu Lys Lys Pro Gly
  1               5                  10                  15

Ala Ser Val Lys Val Ser Cys Lys Ala Ser Gly Tyr Thr Phe Thr
                 20                  25                  30

Asn Tyr Gly Met Asn Trp Val Arg Gln Ala Pro Gly Gln Gly Leu
                 35                  40                  45

Glu Trp Met Gly Trp Ile Asn Thr Tyr Thr Gly Glu Thr Thr Tyr
             50                  55                  60

Ala Asp Asp Phe Lys Gly Arg Phe Val Phe Ser Leu Asp Thr Ser
         65                  70                  75

Val Ser Thr Ala Tyr Leu Gln Ile Ser Ser Leu Lys Ala Glu Asp
             80                  85                  90

Thr Ala Val Tyr Tyr Cys Glu Arg Glu Gly Gly Val Asn Asn Trp
                 95                 100                 105

Gly Gln Gly Thr Leu Val Thr Val Ser Ser
                110                 115

<210> SEQ ID NO 24
<211> LENGTH: 115
<212> TYPE: PRT
<213> ORGANISM: Artificial sequence
<220> FEATURE:
<223> OTHER INFORMATION: Variable heavy chain domain of modified
      humanized anti-Factor D Fab 238-6

<400> SEQUENCE: 24

Gln Val Gln Leu Val Gln Ser Gly Pro Glu Leu Lys Lys Pro Gly
  1               5                  10                  15

Ala Ser Val Lys Val Ser Cys Lys Ala Ser Gly Tyr Thr Phe Thr
                 20                  25                  30

Asn Tyr Gly Met Asn Trp Val Arg Gln Ala Pro Gly Gln Gly Leu
                 35                  40                  45

Glu Trp Met Gly Trp Ile Asn Thr Tyr Thr Gly Glu Thr Thr Tyr
             50                  55                  60

Ala Asp Asp Phe Lys Gly Arg Phe Val Phe Ser Leu Asp Thr Ser
         65                  70                  75

Val Ser Thr Ala Tyr Leu Gln Ile Ser Ser Leu Lys Ala Glu Asp
             80                  85                  90

Thr Ala Val Tyr Tyr Cys Glu Arg Glu Gly Gly Val Asn Asn Trp
                 95                 100                 105

Gly Gln Gly Thr Leu Val Thr Val Ser Ser
                110                 115
```

<210> SEQ ID NO 25
<211> LENGTH: 115
<212> TYPE: PRT
<213> ORGANISM: Artificial sequence
<220> FEATURE:
<223> OTHER INFORMATION: Variable heavy chain domain of modified humanized anti-Factor D Fab 238-7

<400> SEQUENCE: 25

```
Gln Val Gln Leu Val Gln Ser Gly Pro Glu Leu Lys Lys Pro Gly
 1               5                  10                  15

Ala Ser Val Lys Val Ser Cys Lys Ala Ser Gly Tyr Thr Phe Thr
            20                  25                  30

Asn Tyr Gly Met Asn Trp Val Arg Gln Ala Pro Gly Gln Gly Leu
        35                  40                  45

Glu Trp Met Gly Trp Ile Asn Thr Tyr Thr Gly Glu Thr Thr Tyr
    50                  55                  60

Ala Asp Asp Phe Lys Gly Arg Phe Val Phe Ser Leu Asp Thr Ser
65                  70                  75

Val Ser Thr Ala Tyr Leu Gln Ile Ser Ser Leu Lys Ala Glu Asp
            80                  85                  90

Thr Ala Val Tyr Tyr Cys Glu Arg Glu Gly Gly Val Asn Asn Trp
        95                 100                 105

Gly Gln Gly Thr Leu Val Thr Val Ser Ser
                110                 115
```

<210> SEQ ID NO 26
<211> LENGTH: 115
<212> TYPE: PRT
<213> ORGANISM: Artificial sequence
<220> FEATURE:
<223> OTHER INFORMATION: Variable heavy chain domain of modified humanized anti-Factor D Fab 238-8

<400> SEQUENCE: 26

```
Gln Val Gln Leu Val Gln Ser Gly Pro Glu Leu Lys Lys Pro Gly
 1               5                  10                  15

Ala Ser Val Lys Val Ser Cys Lys Ala Ser Gly Tyr Thr Phe Thr
            20                  25                  30

Asn Tyr Gly Met Asn Trp Val Arg Gln Ala Pro Gly Gln Gly Leu
        35                  40                  45

Glu Trp Met Gly Trp Ile Asn Thr Tyr Thr Gly Glu Thr Thr Tyr
    50                  55                  60

Ala Asp Asp Phe Lys Gly Arg Phe Val Phe Ser Leu Asp Thr Ser
65                  70                  75

Val Ser Thr Ala Tyr Leu Gln Ile Ser Ser Leu Lys Ala Glu Asp
            80                  85                  90

Thr Ala Val Tyr Tyr Cys Glu Arg Glu Gly Gly Val Ala Asn Trp
        95                 100                 105

Gly Gln Gly Thr Leu Val Thr Val Ser Ser
                110                 115
```

<210> SEQ ID NO 27
<211> LENGTH: 115
<212> TYPE: PRT
<213> ORGANISM: Artificial sequence
<220> FEATURE:
<223> OTHER INFORMATION: Variable heavy chain domain of modified humanized anti-Factor D Fab 238-9

-continued

<400> SEQUENCE: 27

Gln Val Gln Leu Val Gln Ser Gly Pro Glu Leu Lys Lys Pro Gly
1               5                   10                  15

Ala Ser Val Lys Val Ser Cys Lys Ala Ser Gly Tyr Thr Phe Thr
            20                  25                  30

Asn Tyr Gly Met Asn Trp Val Arg Gln Ala Pro Gly Gln Gly Leu
        35                  40                  45

Glu Trp Met Gly Trp Ile Asn Thr Tyr Thr Gly Glu Thr Thr Tyr
    50                  55                  60

Ala Asp Asp Phe Lys Gly Arg Phe Val Phe Ser Leu Asp Thr Ser
65                  70                  75

Val Ser Thr Ala Tyr Leu Gln Ile Ser Ser Leu Lys Ala Glu Asp
                80                  85                  90

Thr Ala Val Tyr Tyr Cys Glu Arg Glu Gly Gly Val Gln Asn Trp
            95                  100                 105

Gly Gln Gly Thr Leu Val Thr Val Ser Ser
        110                 115

<210> SEQ ID NO 28
<211> LENGTH: 115
<212> TYPE: PRT
<213> ORGANISM: Artificial sequence
<220> FEATURE:
<223> OTHER INFORMATION: Variable heavy chain domain of modified
      humanized anti-Factor D Fab 238-10

<400> SEQUENCE: 28

Gln Val Gln Leu Val Gln Ser Gly Pro Glu Leu Lys Lys Pro Gly
1               5                   10                  15

Ala Ser Val Lys Val Ser Cys Lys Ala Ser Gly Tyr Thr Phe Thr
            20                  25                  30

Asn Tyr Gly Met Asn Trp Val Arg Gln Ala Pro Gly Gln Gly Leu
        35                  40                  45

Glu Trp Met Gly Trp Ile Asn Thr Tyr Thr Gly Glu Thr Thr Tyr
    50                  55                  60

Ala Asp Asp Phe Lys Gly Arg Phe Val Phe Ser Leu Asp Thr Ser
65                  70                  75

Val Ser Thr Ala Tyr Leu Gln Ile Ser Ser Leu Lys Ala Glu Asp
                80                  85                  90

Thr Ala Val Tyr Tyr Cys Glu Arg Glu Gly Gly Val Asn Ala Trp
            95                  100                 105

Gly Gln Gly Thr Leu Val Thr Val Ser Ser
        110                 115

<210> SEQ ID NO 29
<211> LENGTH: 115
<212> TYPE: PRT
<213> ORGANISM: Artificial sequence
<220> FEATURE:
<223> OTHER INFORMATION: Variable heavy chain doman of modified
      humanized anti-Factor D Fab 238-11

<400> SEQUENCE: 29

Gln Val Gln Leu Val Gln Ser Gly Pro Glu Leu Lys Lys Pro Gly
1               5                   10                  15

Ala Ser Val Lys Val Ser Cys Lys Ala Ser Gly Tyr Thr Phe Thr
            20                  25                  30

Asn Tyr Gly Met Asn Trp Val Arg Gln Ala Pro Gly Gln Gly Leu
        35                  40                  45

```
Glu Trp Met Gly Trp Ile Asn Thr Tyr Thr Gly Glu Thr Thr Tyr
            50                  55                  60

Ala Asp Asp Phe Lys Gly Arg Phe Val Phe Ser Leu Asp Thr Ser
            65                  70                  75

Val Ser Thr Ala Tyr Leu Gln Ile Ser Ser Leu Lys Ala Glu Asp
            80                  85                  90

Thr Ala Val Tyr Tyr Cys Glu Arg Glu Gly Gly Val Asn Gln Trp
            95                  100                 105

Gly Gln Gly Thr Leu Val Thr Val Ser Ser
            110                 115

<210> SEQ ID NO 30
<211> LENGTH: 11
<212> TYPE: PRT
<213> ORGANISM: Artificial sequence
<220> FEATURE:
<223> OTHER INFORMATION: HVR-L1 of #111 and 238 to 238-1, 238-6 to
      238-11

<400> SEQUENCE: 30

Ile Thr Ser Thr Asp Ile Asp Asp Asp Met Asn
            5                   10

<210> SEQ ID NO 31
<211> LENGTH: 11
<212> TYPE: PRT
<213> ORGANISM: Artificial sequence
<220> FEATURE:
<223> OTHER INFORMATION: HVR-L1 of modified humanized anti-Factor D Fab
      238-2

<400> SEQUENCE: 31

Ile Thr Ser Thr Asp Ile Asp Asp Asp Leu Asn
            5                   10

<210> SEQ ID NO 32
<211> LENGTH: 11
<212> TYPE: PRT
<213> ORGANISM: Artificial sequence
<220> FEATURE:
<223> OTHER INFORMATION: HVR-L1 of modified humanized anti-Factor D Fab
      238-3

<400> SEQUENCE: 32

Ile Thr Ser Thr Asp Ile Asp Asp Asp Ile Asn
            5                   10

<210> SEQ ID NO 33
<211> LENGTH: 11
<212> TYPE: PRT
<213> ORGANISM: Artificial sequence
<220> FEATURE:
<223> OTHER INFORMATION: HVR-L1 of modified humanized anti-Factor D Fab
      238-4

<400> SEQUENCE: 33

Ile Thr Ser Thr Asp Ile Asp Asp Asp Met Ala
            5                   10

<210> SEQ ID NO 34
<211> LENGTH: 11
<212> TYPE: PRT
<213> ORGANISM: Artificial sequence
<220> FEATURE:
<223> OTHER INFORMATION: HVR-L1 of modified humanized anti-Factor D Fab
      238-5
```

```
<400> SEQUENCE: 34

Ile Thr Ser Thr Asp Ile Asp Asp Asp Met Gln
                5                   10

<210> SEQ ID NO 35
<211> LENGTH: 7
<212> TYPE: PRT
<213> ORGANISM: Artificial sequence
<220> FEATURE:
<223> OTHER INFORMATION: HVR-L2 of #111 and 238 to 238-5 and 238-8 to
      238-11

<400> SEQUENCE: 35

Gly Gly Asn Thr Leu Arg Pro
                5

<210> SEQ ID NO 36
<211> LENGTH: 7
<212> TYPE: PRT
<213> ORGANISM: Artificial sequence
<220> FEATURE:
<223> OTHER INFORMATION: HVR-L2 of modified humanized anti-Factor D Fab
      238-6

<400> SEQUENCE: 36

Gly Gly Ser Thr Leu Arg Pro
                5

<210> SEQ ID NO 37
<211> LENGTH: 7
<212> TYPE: PRT
<213> ORGANISM: Artificial sequence
<220> FEATURE:
<223> OTHER INFORMATION: HVR-L2 of modified humanized anti-Factor D Fab
      238-7

<400> SEQUENCE: 37

Gly Gly Ala Thr Leu Arg Pro
                5

<210> SEQ ID NO 38
<211> LENGTH: 9
<212> TYPE: PRT
<213> ORGANISM: Artificial sequence
<220> FEATURE:
<223> OTHER INFORMATION: HVR-L3 of #111 and 238 to 238-11

<400> SEQUENCE: 38

Leu Gln Ser Asp Ser Leu Pro Tyr Thr
                5

<210> SEQ ID NO 39
<211> LENGTH: 10
<212> TYPE: PRT
<213> ORGANISM: Artificial sequence
<220> FEATURE:
<223> OTHER INFORMATION: HVR-H1 of #111 and 238 to 238-11

<400> SEQUENCE: 39

Gly Tyr Thr Phe Thr Asn Tyr Gly Met Asn
                5                   10

<210> SEQ ID NO 40
<211> LENGTH: 17
<212> TYPE: PRT
<213> ORGANISM: Artificial sequence
<220> FEATURE:
```

```
<223> OTHER INFORMATION: HVR-H2 of #111 and 238 to 238-11

<400> SEQUENCE: 40

Trp Ile Asn Thr Tyr Thr Gly Glu Thr Thr Tyr Ala Asp Asp Phe
 1               5                  10                  15
Lys Gly

<210> SEQ ID NO 41
<211> LENGTH: 6
<212> TYPE: PRT
<213> ORGANISM: Artificial sequence
<220> FEATURE:
<223> OTHER INFORMATION: HVR-H3  of #111 and 238 to 238-7

<400> SEQUENCE: 41

Glu Gly Gly Val Asn Asn
                 5

<210> SEQ ID NO 42
<211> LENGTH: 6
<212> TYPE: PRT
<213> ORGANISM: Artificial sequence
<220> FEATURE:
<223> OTHER INFORMATION: HVR-H3 of modified humanized anti-Factor D Fab
      238-8

<400> SEQUENCE: 42

Glu Gly Gly Val Ala Asn
                 5

<210> SEQ ID NO 43
<211> LENGTH: 6
<212> TYPE: PRT
<213> ORGANISM: Artificial sequence
<220> FEATURE:
<223> OTHER INFORMATION: HVR-H3 of modified humanized anti-Factor D Fab
      238-9

<400> SEQUENCE: 43

Glu Gly Gly Val Gln Asn
                 5

<210> SEQ ID NO 44
<211> LENGTH: 6
<212> TYPE: PRT
<213> ORGANISM: Artificial sequence
<220> FEATURE:
<223> OTHER INFORMATION: HVR-H3 of modified humanized anti-Factor D Fab
      238-10

<400> SEQUENCE: 44

Glu Gly Gly Val Asn Ala
                 5

<210> SEQ ID NO 45
<211> LENGTH: 6
<212> TYPE: PRT
<213> ORGANISM: Artificial sequence
<220> FEATURE:
<223> OTHER INFORMATION: HVR-H3 of modified humanized anti-Factor D Fab
      238-11

<400> SEQUENCE: 45

Glu Gly Gly Val Asn Gln
                 5

<210> SEQ ID NO 46
```

```
<211> LENGTH: 714
<212> TYPE: DNA
<213> ORGANISM: Artificial sequence
<220> FEATURE:
<223> OTHER INFORMATION: Light chain domain of modified humanized
      anti-Factor D Fab 238

<400> SEQUENCE: 46
atgaagaaga atattgcgtt cctacttgcc tctatgtttg tcttttctat         50
agctacaaac gcgtatgctg atatccaggt gacccagtct ccatcctccc        100
tgtctgcatc tgtaggagac cgcgtcacca tcacttgcat taccagcact        150
gatattgatg atgatatgaa ctggtatcag cagaaaccag ggaaagttcc        200
taagctcctg atctctggag gcaatactct tcgtcctggg gtcccatctc        250
ggttcagtgg cagtggatct gggacagatt tcactctcac catcagcagc        300
ctgcagcctg aagatgttgc aacttattac tgtttgcaaa gtgattcttt        350
gccgtacacg tttggccagg gtaccaaggt ggagatcaaa cgaactgtgg        400
ctgcaccatc tgtcttcatc ttcccgccat ctgatgagca gttgaaatct        450
ggaactgctt ctgttgtgtg cctgctgaat aacttctatc ccagagaggc        500
caaagtacag tggaaggtgg ataacgccct ccaatcgggt aactcccagg        550
agagtgtcac agagcaggac agcaaggaca gcacctacag cctcagcagc        600
accctgacgc tgagcaaagc agactacgag aaacacaaag tctacgcctg        650
cgaagtcacc catcagggcc tgagctcgcc cgtcacaaag agcttcaaca        700
ggggagagtg ttaa                                               714

<210> SEQ ID NO 47
<211> LENGTH: 214
<212> TYPE: PRT
<213> ORGANISM: Artificial sequence
<220> FEATURE:
<223> OTHER INFORMATION: Light chain domain of modified humanized
      anti-Factor D Fab 238

<400> SEQUENCE: 47

Asp Ile Gln Val Thr Gln Ser Pro Ser Ser Leu Ser Ala Ser Val
 1               5                  10                  15

Gly Asp Arg Val Thr Ile Thr Cys Ile Thr Ser Thr Asp Ile Asp
                20                  25                  30

Asp Asp Met Asn Trp Tyr Gln Gln Lys Pro Gly Lys Val Pro Lys
                35                  40                  45

Leu Leu Ile Ser Gly Gly Asn Thr Leu Arg Pro Gly Val Pro Ser
                50                  55                  60

Arg Phe Ser Gly Ser Gly Ser Gly Thr Asp Phe Thr Leu Thr Ile
 65                  70                  75

Ser Ser Leu Gln Pro Glu Asp Val Ala Thr Tyr Tyr Cys Leu Gln
                80                  85                  90

Ser Asp Ser Leu Pro Tyr Thr Phe Gly Gln Gly Thr Lys Val Glu
                95                 100                 105

Ile Lys Arg Thr Val Ala Ala Pro Ser Val Phe Ile Phe Pro Pro
                110                 115                 120

Ser Asp Glu Gln Leu Lys Ser Gly Thr Ala Ser Val Val Cys Leu
                125                 130                 135

Leu Asn Asn Phe Tyr Pro Arg Glu Ala Lys Val Gln Trp Lys Val
                140                 145                 150
```

Asp Asn Ala Leu Gln Ser Gly Asn Ser Gln Glu Ser Val Thr Glu
            155                 160                 165

Gln Asp Ser Lys Asp Ser Thr Tyr Ser Leu Ser Ser Thr Leu Thr
            170                 175                 180

Leu Ser Lys Ala Asp Tyr Glu Lys His Lys Val Tyr Ala Cys Glu
            185                 190                 195

Val Thr His Gln Gly Leu Ser Ser Pro Val Thr Lys Ser Phe Asn
            200                 205                 210

Arg Gly Glu Cys

<210> SEQ ID NO 48
<211> LENGTH: 23
<212> TYPE: PRT
<213> ORGANISM: Artificial sequence
<220> FEATURE:
<223> OTHER INFORMATION: FR1-LC of light chain domain of modified
      humanized anti-Factor D Fab 238

<400> SEQUENCE: 48

Asp Ile Gln Val Thr Gln Ser Pro Ser Ser Leu Ser Ala Ser Val
 1               5                  10                  15

Gly Asp Arg Val Thr Ile Thr Cys
                20

<210> SEQ ID NO 49
<211> LENGTH: 15
<212> TYPE: PRT
<213> ORGANISM: Artificial sequence
<220> FEATURE:
<223> OTHER INFORMATION: FR2-LC of light chain domain of modified
      humanized anti-Factor D Fab 238

<400> SEQUENCE: 49

Trp Tyr Gln Gln Lys Pro Gly Lys Val Pro Lys Leu Leu Ile Ser
 1               5                  10                  15

<210> SEQ ID NO 50
<211> LENGTH: 32
<212> TYPE: PRT
<213> ORGANISM: Artificial sequence
<220> FEATURE:
<223> OTHER INFORMATION: FR3-LC of light chain domain of modified
      humanized anti-Factor D Fab 238

<400> SEQUENCE: 50

Gly Val Pro Ser Arg Phe Ser Gly Ser Gly Ser Gly Thr Asp Phe
 1               5                  10                  15

Thr Leu Thr Ile Ser Ser Leu Gln Pro Glu Asp Val Ala Thr Tyr
                20                  25                  30

Tyr Cys

<210> SEQ ID NO 51
<211> LENGTH: 10
<212> TYPE: PRT
<213> ORGANISM: Artificial sequence
<220> FEATURE:
<223> OTHER INFORMATION: FR4-LC of light chain domain of modified
      humanized anti-Factor D Fab 238

<400> SEQUENCE: 51

Phe Gly Gln Gly Thr Lys Val Glu Ile Lys
 1               5                  10

<210> SEQ ID NO 52

<211> LENGTH: 107
<212> TYPE: PRT
<213> ORGANISM: Artificial sequence
<220> FEATURE:
<223> OTHER INFORMATION: CL1 of light chain domain of modified
      humanized anti-Factor D Fab 238 to 238-1

<400> SEQUENCE: 52

```
Arg Thr Val Ala Ala Pro Ser Val Phe Ile Phe Pro Pro Ser Asp
  1               5                  10                  15

Glu Gln Leu Lys Ser Gly Thr Ala Ser Val Val Cys Leu Leu Asn
             20                  25                  30

Asn Phe Tyr Pro Arg Glu Ala Lys Val Gln Trp Lys Val Asp Asn
         35                  40                  45

Ala Leu Gln Ser Gly Asn Ser Gln Glu Ser Val Thr Glu Gln Asp
     50                  55                  60

Ser Lys Asp Ser Thr Tyr Ser Leu Ser Ser Thr Leu Thr Leu Ser
 65                  70                  75

Lys Ala Asp Tyr Glu Lys His Lys Val Tyr Ala Cys Glu Val Thr
             80                  85                  90

His Gln Gly Leu Ser Ser Pro Val Thr Lys Ser Phe Asn Arg Gly
         95                 100                 105

Glu Cys
```

<210> SEQ ID NO 53
<211> LENGTH: 741
<212> TYPE: DNA
<213> ORGANISM: Artificial sequence
<220> FEATURE:
<223> OTHER INFORMATION: Heavy chain domain of modified humanized
      anti-Factor D Fab 238

<400> SEQUENCE: 53

| atgaaaaaga atatcgcatt tcttcttgca tctatgttcg ttttttctat | 50 |
| tgctacaaac gcgtacgctc aggtccagct ggtgcaatct gggcctgagt | 100 |
| tgaagaagcc tggggcctca gtgaaggttt cctgcaaggc ttctggatac | 150 |
| accttcacta actatggaat gaactgggtg cgccaagccc tggacaagg | 200 |
| gcttgagtgg atgggatgga ttaacaccta cactggagag acaacatatg | 250 |
| ctgatgactt caagggacgg tttgtcttct ccttggacac ctctgtcagc | 300 |
| acggcatatc tgcagatcag cagcctcaag gctgaggaca ctgccgtgta | 350 |
| ttactgtgag cgcgaggggg gggttaataa ctggggccaa gggaccctgg | 400 |
| tcaccgtctc ctcagcctcc accaagggcc catcggtctt ccccctggca | 450 |
| ccctcctcca agagcaccte tgggggcaca gcggccctgg gctgcctggt | 500 |
| caaggactac ttccccgaac cggtgacggt gtcgtggaac tcaggcgccc | 550 |
| tgaccagcgg cgtgcacacc ttcccggctg tcctacagtc ctcaggactc | 600 |
| tactccctca gcagcgtggt gaccgtgccc tccagcagct tgggcaccca | 650 |
| gacctacatc tgcaacgtga atcacaagcc cagcaacacc aaggtggaca | 700 |
| agaaagttga gcccaaatct tgtgacaaaa ctcacacata a | 741 |

<210> SEQ ID NO 54
<211> LENGTH: 223
<212> TYPE: PRT
<213> ORGANISM: Artificial sequence
<220> FEATURE:
<223> OTHER INFORMATION: Heavy chain domain of modified humanized anti-Factor D Fab 238

<400> SEQUENCE: 54

Gln Val Gln Leu Val Gln Ser Gly Pro Glu Leu Lys Lys Pro Gly
 1               5                  10                  15

Ala Ser Val Lys Val Ser Cys Lys Ala Ser Gly Tyr Thr Phe Thr
            20                  25                  30

Asn Tyr Gly Met Asn Trp Val Arg Gln Ala Pro Gly Gln Gly Leu
        35                  40                  45

Glu Trp Met Gly Trp Ile Asn Thr Tyr Thr Gly Glu Thr Thr Tyr
    50                  55                  60

Ala Asp Asp Phe Lys Gly Arg Phe Val Phe Ser Leu Asp Thr Ser
65                  70                  75

Val Ser Thr Ala Tyr Leu Gln Ile Ser Ser Leu Lys Ala Glu Asp
                80                  85                  90

Thr Ala Val Tyr Tyr Cys Glu Arg Glu Gly Gly Val Asn Asn Trp
            95                 100                 105

Gly Gln Gly Thr Leu Val Thr Val Ser Ser Ala Ser Thr Lys Gly
        110                 115                 120

Pro Ser Val Phe Pro Leu Ala Pro Ser Ser Lys Ser Thr Ser Gly
    125                 130                 135

Gly Thr Ala Ala Leu Gly Cys Leu Val Lys Asp Tyr Phe Pro Glu
140                 145                 150

Pro Val Thr Val Ser Trp Asn Ser Gly Ala Leu Thr Ser Gly Val
                155                 160                 165

His Thr Phe Pro Ala Val Leu Gln Ser Ser Gly Leu Tyr Ser Leu
            170                 175                 180

Ser Ser Val Val Thr Val Pro Ser Ser Ser Leu Gly Thr Gln Thr
        185                 190                 195

Tyr Ile Cys Asn Val Asn His Lys Pro Ser Asn Thr Lys Val Asp
    200                 205                 210

Lys Lys Val Glu Pro Lys Ser Cys Asp Lys Thr His Thr
215                 220

<210> SEQ ID NO 55
<211> LENGTH: 25
<212> TYPE: PRT
<213> ORGANISM: Artificial sequence
<220> FEATURE:
<223> OTHER INFORMATION: FR1-HC of heavy chain domain of modified
      humanized anti-Factor D Fab 238

<400> SEQUENCE: 55

Gln Val Gln Leu Val Gln Ser Gly Pro Glu Leu Lys Lys Pro Gly
 1               5                  10                  15

Ala Ser Val Lys Val Ser Cys Lys Ala Ser
            20                  25

<210> SEQ ID NO 56
<211> LENGTH: 14
<212> TYPE: PRT
<213> ORGANISM: Artificial sequence
<220> FEATURE:
<223> OTHER INFORMATION: FR2-HC of heavy chain domain of modified
      humanized anti-Factor D Fab 238

<400> SEQUENCE: 56

Trp Val Arg Gln Ala Pro Gly Gln Gly Leu Glu Trp Met Gly
                5                  10

```
<210> SEQ ID NO 57
<211> LENGTH: 32
<212> TYPE: PRT
<213> ORGANISM: Artificial sequence
<220> FEATURE:
<223> OTHER INFORMATION: FR3-HC of heavy chain domain of modified
      humanized anti-Factor D Fab 238

<400> SEQUENCE: 57

Arg Phe Val Phe Ser Leu Asp Thr Ser Val Ser Thr Ala Tyr Leu
 1               5                  10                  15

Gln Ile Ser Ser Leu Lys Ala Glu Asp Thr Ala Val Tyr Tyr Cys
             20                  25                  30

Glu Arg

<210> SEQ ID NO 58
<211> LENGTH: 11
<212> TYPE: PRT
<213> ORGANISM: Artificial sequence
<220> FEATURE:
<223> OTHER INFORMATION: FR4-HC of heavy chain domain of modified
      humanized anti-Factor D Fab 238

<400> SEQUENCE: 58

Trp Gly Gln Gly Thr Leu Val Thr Val Ser Ser
                 5                  10

<210> SEQ ID NO 59
<211> LENGTH: 108
<212> TYPE: PRT
<213> ORGANISM: Artificial sequence
<220> FEATURE:
<223> OTHER INFORMATION: CH1 of heavy chain domain of modified
      humanized anti-Factor D Fab 238 to 238-1

<400> SEQUENCE: 59

Ala Ser Thr Lys Gly Pro Ser Val Phe Pro Leu Ala Pro Ser Ser
 1               5                  10                  15

Lys Ser Thr Ser Gly Gly Thr Ala Ala Leu Gly Cys Leu Val Lys
             20                  25                  30

Asp Tyr Phe Pro Glu Pro Val Thr Val Ser Trp Asn Ser Gly Ala
             35                  40                  45

Leu Thr Ser Gly Val His Thr Phe Pro Ala Val Leu Gln Ser Ser
             50                  55                  60

Gly Leu Tyr Ser Leu Ser Ser Val Val Thr Val Pro Ser Ser Ser
             65                  70                  75

Leu Gly Thr Gln Thr Tyr Ile Cys Asn Val Asn His Lys Pro Ser
             80                  85                  90

Asn Thr Lys Val Asp Lys Lys Val Glu Pro Lys Ser Cys Asp Lys
             95                  100                 105

Thr His Thr

<210> SEQ ID NO 60
<211> LENGTH: 714
<212> TYPE: DNA
<213> ORGANISM: Artificial sequence
<220> FEATURE:
<223> OTHER INFORMATION: Light chain domain of modified humanized
      anti-Factor D Fab 238-1

<400> SEQUENCE: 60
atgaagaaga atattgcgtt cctacttgcc tctatgtttg tctttttctat            50
```

```
agctacaaac gcgtatgctg atatccaggt gacccagtct ccatcctccc            100
tgtctgcatc tgtaggagac cgcgtcacca tcacttgcat taccagcact            150
gatattgatg atgatatgaa ctggtatcag cagaaaccag ggaaagttcc            200
taagctcctg atctctggag caatactct tcgtcctggg gtcccatctc             250
ggttcagtgg cagtggatct gggacagatt tcactctcac catcagcagc            300
ctgcagcctg aagatgttgc aacttattac tgtttgcaaa gtgattcttt            350
gccgtacacg tttggccagg gtaccaaggt ggagatcaaa cgaactgtgg            400
ctgcaccatc tgtcttcatc ttcccgccat ctgatgagca gttgaaatct            450
ggaactgctt ctgttgtgtg cctgctgaat aacttctatc ccagagaggc            500
caaagtacag tggaaggtgg ataacgccct ccaatcgggt aactcccagg            550
agagtgtcac agagcaggac agcaaggaca gcacctacag cctcagcagc            600
accctgacgc tgagcaaagc agactacgag aaacacaaag tctacgcctg            650
cgaagtcacc catcagggcc tgagctcgcc cgtcacaaag agcttcaaca            700
ggggagagtg ttaa                                                   714
```

<210> SEQ ID NO 61
<211> LENGTH: 214
<212> TYPE: PRT
<213> ORGANISM: Artificial sequence
<220> FEATURE:
<223> OTHER INFORMATION: Light chain domain of modified humanized
      anti-Factor D Fab 238-1

<400> SEQUENCE: 61

```
Asp Ile Gln Val Thr Gln Ser Pro Ser Ser Leu Ser Ala Ser Val
  1               5                  10                  15

Gly Asp Arg Val Thr Ile Thr Cys Ile Thr Ser Thr Asp Ile Asp
                 20                  25                  30

Asp Asp Met Asn Trp Tyr Gln Gln Lys Pro Gly Lys Val Pro Lys
                 35                  40                  45

Leu Leu Ile Ser Gly Gly Asn Thr Leu Arg Pro Gly Val Pro Ser
                 50                  55                  60

Arg Phe Ser Gly Ser Gly Ser Gly Thr Asp Phe Thr Leu Thr Ile
                 65                  70                  75

Ser Ser Leu Gln Pro Glu Asp Val Ala Thr Tyr Tyr Cys Leu Gln
                 80                  85                  90

Ser Asp Ser Leu Pro Tyr Thr Phe Gly Gln Gly Thr Lys Val Glu
                 95                 100                 105

Ile Lys Arg Thr Val Ala Ala Pro Ser Val Phe Ile Phe Pro Pro
                110                 115                 120

Ser Asp Glu Gln Leu Lys Ser Gly Thr Ala Ser Val Val Cys Leu
                125                 130                 135

Leu Asn Asn Phe Tyr Pro Arg Glu Ala Lys Val Gln Trp Lys Val
                140                 145                 150

Asp Asn Ala Leu Gln Ser Gly Asn Ser Gln Glu Ser Val Thr Glu
                155                 160                 165

Gln Asp Ser Lys Asp Ser Thr Tyr Ser Leu Ser Ser Thr Leu Thr
                170                 175                 180

Leu Ser Lys Ala Asp Tyr Glu Lys His Lys Val Tyr Ala Cys Glu
                185                 190                 195

Val Thr His Gln Gly Leu Ser Ser Pro Val Thr Lys Ser Phe Asn
                200                 205                 210
```

Arg Gly Glu Cys

<210> SEQ ID NO 62
<211> LENGTH: 741
<212> TYPE: DNA
<213> ORGANISM: Artificial sequence
<220> FEATURE:
<223> OTHER INFORMATION: Heavy chain domain of modified humanized anti-Factor D Fab 238-1

<400> SEQUENCE: 62

| | |
|---|---|
| atgaaaaaga atatcgcatt tcttcttgca tctatgttcg tttttctat | 50 |
| tgctacaaac gcgtacgctg aagtccagct ggtgcaatct gggcctgagt | 100 |
| tgaagaagcc tggggcctca gtgaaggttt cctgcaaggc ttctggatac | 150 |
| accttcacta actatggaat gaactgggtg cgccaagccc tggacaagg | 200 |
| gcttgagtgg atgggatgga ttaacaccta cactggagag acaacatatg | 250 |
| ctgatgactt caagggacgg tttgtcttct ccttggacac ctctgtcagc | 300 |
| acggcatatc tgcagatcag cagcctcaag gctgaggaca ctgccgtgta | 350 |
| ttactgtgag cgcgaggggg gggttaataa ctggggccaa gggaccctgg | 400 |
| tcaccgtctc ctcagcctcc accaagggcc catcggtctt ccccctggca | 450 |
| ccctcctcca agagcacctc tgggggcaca gcggccctgg gctgcctggt | 500 |
| caaggactac ttccccgaac cggtgacggt gtcgtggaac tcaggcgccc | 550 |
| tgaccagcgg cgtgcacacc ttcccggctg tcctacagtc ctcaggactc | 600 |
| tactccctca gcagcgtggt gaccgtgccc tccagcagct gggcaccca | 650 |
| gacctacatc tgcaacgtga atcacaagcc cagcaacacc aaggtggaca | 700 |
| agaaagttga gcccaaatct tgtgacaaaa ctcacacata a | 741 |

<210> SEQ ID NO 63
<211> LENGTH: 223
<212> TYPE: PRT
<213> ORGANISM: Artificial sequence
<220> FEATURE:
<223> OTHER INFORMATION: Heavy chain domain of modified humanized anti-Factor D Fab 238-1

<400> SEQUENCE: 63

Glu Val Gln Leu Val Gln Ser Gly Pro Glu Leu Lys Lys Pro Gly
 1               5                  10                  15

Ala Ser Val Lys Val Ser Cys Lys Ala Ser Gly Tyr Thr Phe Thr
                20                  25                  30

Asn Tyr Gly Met Asn Trp Val Arg Gln Ala Pro Gly Gln Gly Leu
            35                  40                  45

Glu Trp Met Gly Trp Ile Asn Thr Tyr Thr Gly Glu Thr Thr Tyr
        50                  55                  60

Ala Asp Asp Phe Lys Gly Arg Phe Val Phe Ser Leu Asp Thr Ser
    65                  70                  75

Val Ser Thr Ala Tyr Leu Gln Ile Ser Ser Leu Lys Ala Glu Asp
            80                  85                  90

Thr Ala Val Tyr Tyr Cys Glu Arg Glu Gly Gly Val Asn Asn Trp
            95                 100                 105

Gly Gln Gly Thr Leu Val Thr Val Ser Ser Ala Ser Thr Lys Gly
            110                 115                 120

Pro Ser Val Phe Pro Leu Ala Pro Ser Ser Lys Ser Thr Ser Gly

```
                 125                 130                 135
Gly Thr Ala Ala Leu Gly Cys Leu Val Lys Asp Tyr Phe Pro Glu
            140                 145                 150

Pro Val Thr Val Ser Trp Asn Ser Gly Ala Leu Thr Ser Gly Val
            155                 160                 165

His Thr Phe Pro Ala Val Leu Gln Ser Ser Gly Leu Tyr Ser Leu
            170                 175                 180

Ser Ser Val Val Thr Val Pro Ser Ser Ser Leu Gly Thr Gln Thr
            185                 190                 195

Tyr Ile Cys Asn Val Asn His Lys Pro Ser Asn Thr Lys Val Asp
            200                 205                 210

Lys Lys Val Glu Pro Lys Ser Cys Asp Lys Thr His Thr
            215                 220

<210> SEQ ID NO 64
<211> LENGTH: 25
<212> TYPE: PRT
<213> ORGANISM: Artificial sequence
<220> FEATURE:
<223> OTHER INFORMATION: FR1-HC of heavy chain domain of modified
      humanized anti-Factor D Fab 238-1

<400> SEQUENCE: 64

Glu Val Gln Leu Val Gln Ser Gly Pro Glu Leu Lys Lys Pro Gly
  1               5                  10                  15

Ala Ser Val Lys Val Ser Cys Lys Ala Ser
            20                  25

<210> SEQ ID NO 65
<211> LENGTH: 107
<212> TYPE: PRT
<213> ORGANISM: Artificial sequence
<220> FEATURE:
<223> OTHER INFORMATION: VL Kappa I consensus sequence

<400> SEQUENCE: 65

Asp Ile Gln Met Thr Gln Ser Pro Ser Ser Leu Ser Ala Ser Val
  1               5                  10                  15

Gly Asp Arg Val Thr Ile Thr Cys Arg Ala Ser Gln Gly Ile Ser
            20                  25                  30

Ser Tyr Leu Ala Trp Tyr Gln Gln Lys Pro Gly Lys Ala Pro Lys
            35                  40                  45

Leu Leu Ile Tyr Ala Ala Ser Ser Leu Gln Ser Gly Val Pro Ser
            50                  55                  60

Arg Phe Ser Gly Ser Gly Ser Gly Thr Asp Phe Thr Leu Thr Ile
            65                  70                  75

Ser Ser Leu Gln Pro Glu Asp Phe Ala Thr Tyr Tyr Cys Gln Gln
            80                  85                  90

Tyr Asn Ser Tyr Pro Thr Phe Gly Gln Gly Thr Lys Val Glu Ile
            95                 100                 105

Lys Arg

<210> SEQ ID NO 66
<211> LENGTH: 109
<212> TYPE: PRT
<213> ORGANISM: Artificial sequence
<220> FEATURE:
<223> OTHER INFORMATION: VH7 subgroup VII consensus sequence

<400> SEQUENCE: 66
```

```
Gln Val Gln Leu Val Gln Ser Gly Ser Glu Leu Lys Lys Pro Gly
 1               5                  10                  15

Ala Ser Val Lys Val Ser Cys Lys Ala Ser Gly Tyr Thr Phe Thr
            20                  25                  30

Ser Tyr Ala Met Asn Trp Val Arg Gln Ala Pro Gly Gln Gly Leu
            35                  40                  45

Glu Trp Met Gly Trp Ile Asn Thr Asn Thr Gly Asn Pro Thr Tyr
            50                  55                  60

Ala Gln Gly Phe Thr Gly Arg Phe Val Phe Ser Leu Asp Thr Ser
            65                  70                  75

Val Ser Thr Ala Tyr Leu Gln Ile Ser Ser Leu Lys Ala Glu Asp
            80                  85                  90

Thr Ala Val Tyr Tyr Cys Ala Arg Trp Gly Gln Gly Thr Ser Leu
            95                 100                 105

Thr Val Ser Ser
```

<210> SEQ ID NO 67
<211> LENGTH: 37
<212> TYPE: DNA
<213> ORGANISM: Artificial sequence
<220> FEATURE:
<223> OTHER INFORMATION: Synthesized Oligonucleotide Primer for
      pAEP1-283 VL

<400> SEQUENCE: 67 tttcccttg atatccaggt gacccagtct ccatcct                              37

<210> SEQ ID NO 68
<211> LENGTH: 42
<212> TYPE: DNA
<213> ORGANISM: Artificial sequence
<220> FEATURE:
<223> OTHER INFORMATION: Synthesized Oligonucleotide Primer for
      pAEPI-238-VL

<400> SEQUENCE: 68 tttcccttg gtaccctggc caaacgtgta cggcaaagaa tc                        42

<210> SEQ ID NO 69
<211> LENGTH: 41
<212> TYPE: DNA
<213> ORGANISM: Artificial sequence
<220> FEATURE:
<223> OTHER INFORMATION: Synthesized Oligonucleotide Primer for p238

<400> SEQUENCE: 69
tttgggtttc gtacgctcag gtccagctgg tgcaatctgg g                        41

<210> SEQ ID NO 70
<211> LENGTH: 47
<212> TYPE: DNA
<213> ORGANISM: Artificial sequence
<220> FEATURE:
<223> OTHER INFORMATION: Synthesized Oligonucleotide Primer for p238

<400> SEQUENCE: 70
tttgggtttg ggcccttggt ggaggctgag gagacggtga ccagggt                  47

<210> SEQ ID NO 71
<211> LENGTH: 41
<212> TYPE: DNA
<213> ORGANISM: Artificial sequence
<220> FEATURE:
<223> OTHER INFORMATION: Synthesized Oligonucleotide Primer for p238-1

```
<400> SEQUENCE: 71
tttgggtttc gtacgctgaa gtccagctgg tgcaatctgg  g                    41

<210> SEQ ID NO 72
<211> LENGTH: 47
<212> TYPE: DNA
<213> ORGANISM: Artificial sequence
<220> FEATURE:
<223> OTHER INFORMATION: Synthesized Oligonucleotide Primer for p238-1

<400> SEQUENCE: 72
tttgggtttg ggcccttggt ggaggctgag gagacggtga  ccaggt               47

<210> SEQ ID NO 73
<211> LENGTH: 107
<212> TYPE: PRT
<213> ORGANISM: Artificial sequence
<220> FEATURE:
<223> OTHER INFORMATION: Variable light chain composite of modified
      humanized anti-Factor D Fab clones
<220> FEATURE:
<221> NAME/KEY: Xaa
<222> LOCATION: 33-34
<223> OTHER INFORMATION: Unknown amino acid
<220> FEATURE:
<221> NAME/KEY: Xaa
<222> LOCATION: 52
<223> OTHER INFORMATION: Unknown amino acid
<220> FEATURE:
<221> NAME/KEY: Xaa
<222> LOCATION: 104
<223> OTHER INFORMATION: Unknown amino acid

<400> SEQUENCE: 73

Asp Ile Gln Val Thr Gln Ser Pro Ser Ser Leu Ser Ala Ser Val
 1               5                  10                  15

Gly Asp Arg Val Thr Ile Thr Cys Ile Thr Ser Thr Asp Ile Asp
                20                  25                  30

Asp Asp Xaa Xaa Trp Tyr Gln Gln Lys Pro Gly Lys Val Pro Lys
                35                  40                  45

Leu Leu Ile Ser Gly Gly Xaa Thr Leu Arg Pro Gly Val Pro Ser
                50                  55                  60

Arg Phe Ser Gly Ser Gly Ser Gly Thr Asp Phe Thr Leu Thr Ile
                65                  70                  75

Ser Ser Leu Gln Pro Glu Asp Val Ala Thr Tyr Tyr Cys Leu Gln
                80                  85                  90

Ser Asp Ser Leu Pro Tyr Thr Phe Gly Gln Gly Thr Lys Xaa Glu
                95                  100                 105

Ile Lys

<210> SEQ ID NO 74
<211> LENGTH: 115
<212> TYPE: PRT
<213> ORGANISM: Artificial sequence
<220> FEATURE:
<223> OTHER INFORMATION: Variable heavy chain composite of modified
      humanized Anti-Factor D Fab Clones
<220> FEATURE:
<221> NAME/KEY: Xaa
<222> LOCATION: 1
<223> OTHER INFORMATION: Unknown amino acid
<220> FEATURE:
<221> NAME/KEY: Xaa
<222> LOCATION: 103
<223> OTHER INFORMATION: Unknown amino acid
<220> FEATURE:
```

```
<221> NAME/KEY: Xaa
<222> LOCATION: 104
<223> OTHER INFORMATION: Unknown amino acid

<400> SEQUENCE: 74

Xaa Val Gln Leu Val Gln Ser Gly Pro Glu Leu Lys Lys Pro Gly
 1               5                  10                  15

Ala Ser Val Lys Val Ser Cys Lys Ala Ser Gly Tyr Thr Phe Thr
             20                  25                  30

Asn Tyr Gly Met Asn Trp Val Arg Gln Ala Pro Gly Gln Gly Leu
             35                  40                  45

Glu Trp Met Gly Trp Ile Asn Thr Tyr Thr Gly Glu Thr Thr Tyr
             50                  55                  60

Ala Asp Asp Phe Lys Gly Arg Phe Val Phe Ser Leu Asp Thr Ser
             65                  70                  75

Val Ser Thr Ala Tyr Leu Gln Ile Ser Ser Leu Lys Ala Glu Asp
             80                  85                  90

Thr Ala Val Tyr Tyr Cys Glu Arg Glu Gly Gly Val Xaa Xaa Trp
             95                 100                 105

Gly Gln Gly Thr Leu Val Thr Val Ser Ser
             110                 115
```

HUMANIZED ANTI-FACTOR D ANTIBODIES AND USES THEREOF

CROSS REFERENCE TO RELATED APPLICATIONS

This non-provisional application filed under 37 CFR §1.53(b), claims the benefit under 35 USC §119(e) to U.S. Provisional Application Ser. No. 61/048,431, filed on Apr. 28, 2008 and U.S. Provisional Application Ser. No. 61/048,689 filed on Apr. 29, 2008, the contents of which are hereby incorporated by reference in their entirety.

BACKGROUND OF THE INVENTION

The complement system plays a central role in the clearance of immune complexes and the immune response to infectious agents, foreign antigens, virus-infected cells and tumor cells. However, complement is also involved in pathological inflammation and in autoimmune diseases. Therefore, inhibition of excessive or uncontrolled activation of the complement cascade could provide clinical benefit to patients with such diseases and conditions.

The complement system encompasses two distinct activation pathways, designated the classical and the alternative pathways (V. M. Holers, In *Clinical Immunology: Principles and Practice*, ed. R. R. Rich, Mosby Press; 1996, 363-391). The classical pathway is a calcium/magnesium-dependent cascade which is normally activated by the formation of antigen-antibody complexes. The alternative pathway is a magnesium-dependent cascade which is activated by deposition and activation of C3 on certain susceptible surfaces (e.g. cell wall polysaccharides of yeast and bacteria, and certain biopolymer materials). Activation of the complement pathway generates biologically active fragments of complement proteins, e.g. C3a, C4a and C5a anaphylatoxins and C5b-9 membrane attack complexes (MAC), which mediate inflammatory activities involving leukocyte chemotaxis, activation of macrophages, neutrophils, platelets, mast cells and endothelial cells, vascular permeability, cytolysis, and tissue injury.

Factor D is a highly specific serine protease essential for activation of the alternative complement pathway. It cleaves factor B bound to C3b, generating the C3b/Bb enzyme which is the active component of the alternative pathway C3/C5 convertases. Factor D may be a suitable target for inhibition, since its plasma concentration in humans is very low (1.8 µg/ml), and it has been shown to be the limiting enzyme for activation of the alternative complement pathway (P. H. Lesavre and H. J. Müller-Eberhard. *J. Exp. Med.,* 1978; 148: 1498-1510; J. E. Volanakis et al., *New Eng. J. Med.,* 1985; 312: 395-401).

The down-regulation of complement activation has been demonstrated to be effective in treating several disease indications in animal models and in ex vivo studies, e.g. systemic lupus erythematosus and glomerulonephritis (Y. Wang et al., *Proc. Natl. Acad. Sci.;* 1996, 93: 8563-8568), rheumatoid arthritis (Y. Wang et al., *Proc. Natl. Acad. Sci.,* 1995; 92: 8955-8959), cardiopulmonary bypass and hemodialysis (C. S. Rinder, *J. Clin. Invest.,* 1995; 96: 1564-1572), hyperacute rejection in organ transplantation (T. J. Kroshus et al., *Transplantation,* 1995; 60:1194-1202), myocardial infarction (J. W. Homeister et al., *J. Immunol.,* 1993; 150: 1055-1064; H. F. Weisman et al., *Science,* 1990; 249: 146-151), reperfusion injury (E. A. Amsterdam et al., *Am. J. Physiol.,* 1995; 268: H448-H457), and adult respiratory distress syndrome (R. Rabinovici et al., *J. Immunol.,* 1992; 149: 1744-1750). In addition, other inflammatory conditions and autoimmune/immune complex diseases are also closely associated with complement activation (V. M. Holers, ibid., B. P. Morgan. *Eur. J. Clin. Invest.,* 1994: 24: 219-228), including thermal injury, severe asthma, anaphylactic shock, bowel inflammation, urticaria, angioedema, vasculitis, multiple sclerosis, myasthenia gravis, membranoproliferative glomerulonephritis, and Sjögren's syndrome.

There is a need for antibody therapeutics in the field of complement-mediated disorders, and humanized anti-Factor D antibodies, and antibody variants thereof, and fragments thereof (e.g. antigen-binding fragments), of the present invention provide high affinity antibodies useful to meet this need.

SUMMARY OF THE INVENTION

In one aspect, the present invention relates generally to antibodies capable of inhibiting biological activities associated with Factor D.

In one aspect, the present invention relates to humanized anti-Factor D antibodies, having a variety of therapeutically desired characteristics. The invention includes the amino acid sequences of the HVRs of these humanized anti-Factor D antibodies, and their corresponding nucleic acid sequences. The invention includes the amino acid sequences of the variable domains of the heavy and light chain of the humanized anti-Factor D antibodies, and their corresponding nucleic acid sequences. The invention includes the amino acid sequences of the heavy and light chain of the humanized anti-Factor D antibodies, and their corresponding nucleic acid sequences.

In one aspect, specific antibodies within the scope of this invention include, without limitation humanized anti-Factor D antibodies, comprising HVRs of humanized anti-Factor D Fab clones #238, 238-1, 238-2, 238-3, 238-4, 238-5, 238-6, 238-7, 238-8, 238-9, 238-10 or 238-11. In one embodiment, the humanized anti-Factor D antibodies comprise the variable domains of the heavy and/or light chains of humanized anti-Factor D Fab clones #238,238-1, 238-2, 238-3, 238-4, 238-5, 238-6, 238-7, 238-8, 238-9, 238-10 or 238-11. In one embodiment, the humanized anti-Factor D antibodies comprise the heavy and/or light chains of humanized anti-Factor D Fab clones #238, 238-1, 238-2, 238-3, 238-4, 238-5, 238-6, 238-7, 238-8, 238-9, 238-10 or 238-11. In one embodiment, the invention includes the humanized anti-factor D Fab clones #238, 238-1, 238-2, 238-3, 238-4, 238-5, 238-6, 238-7, 238-8, 238-9, 238-10 or 238-11. In one embodiment, the invention includes antibody fragments (e.g. antigen-binding fragments) of full-length antibodies of humanized anti-Factor D Fab clones #238, 238-1, 238-2, 238-3, 238-4, 238-5, 238-6, 238-7, 238-8, 238-9, 238-10 or 238-11. In one embodiment, the invention includes full-length antibodies or antigen-binding fragments thereof, comprising the antigen-binding sequences of the heavy chain and/or the light chain of humanized anti-Factor D Fab clones #238, 238-1, 238-2, 238-3, 238-4, 238-5, 238-6, 238-7, 238-8, 238-9, 238-10 or238-11. In one embodiment, such antigen-binding sequences comprise at least one, two, or three of the HVRs of the heavy chain. In one embodiment, such antigen-binding sequences comprise at least one, two, or three of the HVRs of the light chain. In one embodiment, such antigen-binding sequences comprise at least a portion or all of the heavy chain variable domain. In one embodiment, such antigen-binding sequences comprise at least a portion or all of the light chain variable domain.

In one aspect, the present invention provides antibody fragments (e.g. antigen-binding fragments) or full-length antibodies of humanized anti-Factor D Fab clone #111, comprising at least one modification of the sequence of humanized anti-Factor D Fab clone #111, wherein such full-length antibodies or such antigen-binding fragments comprise the antigen-binding sequences of the heavy chain and/or the light chain of humanized anti-Factor D Fab clone #111. In one embodiment, the antibody fragments (e.g. antigen-binding fragments) or full-length antibodies of humanized anti-Factor D Fab clone #111, comprising at least one modification of the sequence of humanized anti-Factor D Fab clone #111, comprising the antigen-binding sequences of the heavy chain and/or the light chain of humanized anti-Factor D Fab clone #111, further bind essentially to the same epitope as humanized antibody Fab clone #111. In one embodiment, such antigen-binding sequences comprise at least one, two or three of the HVRs of the heavy chain. In one embodiment, such antigen-binding sequences comprise at least one, two or three of the HVRs of the light chain. In one embodiment, such antigen-binding sequences comprise at least a portion or all of the heavy chain variable domain. In one embodiment, such antigen-binding sequences comprise at least a portion or all of the light chain variable domain. In one embodiment, such modification in said antibody fragments or said full-length antibodies, is in the heavy chain. In one embodiment, such modification in said antibody fragments or said full-length antibodies, is in the light chain. In one embodiment, such modification in said antibody fragments or said full-length antibodies, is in the heavy chain variable domain. In one embodiment, such modification in said antibody fragments or said full-length antibodies, is in the light chain variable domain. In one embodiment, such modification in said antibody fragments or said full-length antibodies, is in at least one, two or three of the HVRs of the heavy chain. In one embodiment, such modification in said antibody fragments or said full-length antibodies, is in at least one, two or three of the HVRs of the light chain.

In one aspect, the invention concerns antibodies of the present invention, or fragments thereof (e.g. antigen-binding fragments), which bind to Factor D with a binding affinity of at least about $10^{-9}$ to $10^{-12}$M.

In one aspect, the invention concerns antibodies of the present invention, or fragments thereof (e.g. antigen-binding fragments), wherein a Fab fragment of such antibodies inhibits a biological function of Factor D in a Fab fragment to Factor D molar ratio of about 0.05:1 (0.05) to about 10:1 (10), or about 0.09:1 (0.09) to about 8:1 (8), or about 0.1:1 (0.1) to about 6:1 (6), or about 0.15:1 (0.15) to about 5:1 (5), or about 0.19:1 (0.19) to about 4:1 (4), or about 0.2:1 (0.2) to about 3:1 (3), or about 0.3:1 (0.3) to about 2:1 (2), or about 0.4:1 (0.4) to about 1:1 (1), or about 0.5:1 (0.5) to about 1:2 (0.5), or about 0.6:1 (0.6) to about 1:3 (0.33), or about 0.7:1 (0.7) to about 1:4 (0.25), or about 0.8:1 (0.8) to about 1:5 (0.2) or about 0.9:1 (0.9) to about 1:6 (0.17).

In one aspect, the antibodies of the present invention include human, humanized or chimeric antibodies.

In another aspect, the present invention includes antibody fragments (e.g. antigen-binding fragments) of humanized anti-Factor D antibodies. The antibody fragments of the present invention may, for example, be Fab, Fab', F(ab')$_2$, scFv, (scFv)$_2$, dAb, complementarity determining region (CDR) fragments, linear antibodies, single-chain antibody molecules, minibodies, diabodies, or multispecific antibodies formed from antibody fragments.

In other aspects of the invention, the present invention includes compositions comprising an antibody of the invention, or fragment thereof (e.g. antigen-binding fragment). In another embodiment, the invention provides cell lines and vectors encoding at least a portion of an antibody of the invention, or fragment thereof (e.g. antigen-binding fragment). In one aspect, the invention includes method of making, method of producing, and method of using antibodies, or fragments thereof (e.g. antigen-binding fragments) and compositions of the invention. In one embodiment, the method of making an antibody of the invention, or fragment thereof (e.g. antigen-binding fragment), wherein the method comprises (a) culturing a host cell, for example a eukaryotic or CHO cell, comprising a vector, further comprising a polynucleotide encoding an antibody of the invention, or fragment thereof (e.g. antigen-binding fragment), under conditions suitable for expression of the polynucleotide encoding the antibody, or fragment thereof (e.g. antigen-binding fragment) and (b) isolating the antibody, or fragment thereof (e.g. antigen-binding fragment).

In a still further aspect, the invention concerns a composition of matter comprising an antibody of the invention, or fragment thereof (e.g. antigen-binding fragment), as described herein, in combination with a carrier. Optionally, the carrier is a pharmaceutically acceptable carrier.

Another aspect of the present invention is the use of these humanized antibodies or antibody fragments thereof (e.g. antigen-binding fragments), for the preparation of a medicament or composition for the prevention and/or treatment of disorders associated with excessive or uncontrolled complement activation. They include complement activation during cardiopulmonary bypass operations; complement activation due to ischemia-reperfusion following acute myocardial infarction, aneurysm, stroke, hemorrhagic shock, crush injury, multiple organ failure, hypobolemic shock, intestinal ischemia or other events causing ischemia. Complement activation has also been shown to be associated with inflammatory conditions such as severe burns, endotoxemia, septic shock, adult respiratory distress syndrome, hemodialysis; anaphylactic shock, severe asthma, angioedema, Crohn's disease, sickle cell anemia, poststreptococcal glomerulonephritis and pancreatitis. The disorder may be the result of an adverse drug reaction, drug allergy, IL-2 induced vascular leakage syndrome or radiographic contrast media allergy. It also includes autoimmune disease such as systemic lupus erythematosus, myasthenia gravis, rheumatoid arthritis, Alzheimer's disease and multiple sclerosis. In another embodiment, complement activation is also associated with transplant rejection. In another embodiment, complement activation is also associated with ocular diseases (all ocular conditions and diseases the pathology of which involve complement, including the classical and the alternative pathway of complement), such as, for example, without limitation, macular degenerative disease, such as all stages of age-related macular degeneration (AMD), including dry and wet (non-exudative and exudative) forms, diabetic retinopathy and other ischemia-related retinopathies, choroidal neovascularization (CNV), uveitis, diabetic macular edema, pathological myopia, von Hippel-Lindau disease, histoplasmosis of the eye, Central Retinal Vein Occlusion (CRVO), corneal neovascularization, and retinal neovascularization. In one example, complement-associated eye conditions include age-related macular degeneration (AMD), including non-exudative (e.g intermediate dry AMD or geographic atrophy (GA)) and exudative (e.g. wet AMD (choroidal neovascularization (CNV)) AMD, diabetic retinopathy (DR), endophthalmitis and uveitis. In a further example, nonexudative AMD may include the presence of hard drusen, soft drusen, geographic atrophy and/or pigment clumping. In another example, complement-associated eye conditions include age-related macular degeneration (AMD), including early AMD (e.g.

includes multiple small to one or more non-extensive medium sized drusen), intermediate AMD (e.g. includes extensive medium drusen to one or more large drusen) and advanced AMD (e.g. includes geographic atrophy or advanced wet AMD (CNV). In a further example, intermediate dry AMD may include large confluent drusen. In a further example, geographic atrophy may include photoreceptor and/or Retinal Pigmented Epithelial (RPE) loss. In a further example, the area of geographic atrophy may be small or large and/or may be in the macula area or in the peripheral retina. In one example, the complement-associated eye condition is intermediate dry AMD. In one example, the complement-associated eye condition is geographic atrophy. In one example, the complement-associated eye condition is wet AMD (choroidal neovascularization (CNV)).

In another aspect, the invention provides a kit, comprising an antibody of the invention, or fragment thereof (e.g. antigen-binding fragment). In one embodiment, the invention provides a kit, comprising an antibody of the invention, or fragment thereof (e.g. antigen-binding fragment) and instructions for use. In one embodiment, the invention concerns a kit comprising an antibody of the invention, or fragment thereof (e.g. antigen-binding fragment) and instructions for administering said antibody, to treat a complement-associated disorder. In one embodiment, the invention provides a kit comprising a first container comprising a composition comprising one or more one or more antibodies of the invention, or antibody fragments thereof (e.g. antigen-binding fragments); and a second container comprising a buffer. In one embodiment, the buffer is pharmaceutically acceptable. In one embodiment, a composition comprising an antibody of the invention, or fragment thereof (e.g. antigen-binding fragment) further comprises a carrier, which in some embodiments is pharmaceutically acceptable. In one embodiment, a kit further comprises instructions for administering the composition (e.g the antibody, or antibody fragment thereof (e.g. antigen-binding fragment) to a subject. In one embodiment, a kit further comprises instructions for use of the kit.

In one aspect, the invention concerns an article of manufacture containing materials useful for the treatment, prevention and/or diagnosis of complement-associated disorders. In one embodiment, the invention concerns an article of manufacture, comprising: (a) a container; (b) a label on the container; and (c) a composition of matter comprising an antibody, or variant thereof or fragment thereof (e.g. antigen-binding fragment), of the present invention, contained with the container, wherein the label on said container indicates that the composition can be used for treatment, prevention and/or diagnosis of complement-associated disorders.

In one aspect, the invention provides use of an anti-Factor D antibody of the invention, or antibody fragment thereof (e.g. antigen-binding fragment), nucleic acid of the invention, expression vector of the invention or host cell of the invention, in the preparation of a medicament for the therapeutic and/or prophylactic treatment of a disease, such as a complement-associated eye condition. In one embodiment, the complement-associated eye condition is selected from age-related macular degeneration (AMD), including non-exudative (e.g intermediate dry AMD or geographic atrophy (GA)) and exudative (e.g. wet AMD (choroidal neovascularization (CNV)) AMD, diabetic retinopathy (DR), endophthalmitis and uveitis. In one example, the complement-associated eye condition is intermediate dry AMD. In one example, the complement-associated eye condition is geographic atrophy. In one example, the complement-associated eye condition is wet AMD (choroidal neovascularization (CNV)).

In one aspect, the invention provides use of an article of manufacture of the invention in the preparation of a medicament for the therapeutic and/or prophylactic treatment of a disease, such as a complement-associated eye condition. In one embodiment, the complement-associated eye condition is selected from age-related macular degeneration (AMD), including non-exudative (e.g intermediate dry AMD or geographic atrophy (GA)) and exudative (e.g. wet AMD (choroidal neovascularization (CNV)) AMD, diabetic retinopathy (DR), endophthalmitis and uveitis. In one example, the complement-associated eye condition is intermediate dry AMD. In one example, the complement-associated eye condition is geographic atrophy. In one example, the complement-associated eye condition is wet AMD (choroidal neovascularization (CNV)).

In one aspect, the invention provides use of a kit of the invention in the preparation of a medicament for the therapeutic and/or prophylactic treatment of a disease, such as a complement-associated eye condition. In one embodiment, the complement-associated eye condition is selected from age-related macular degeneration (AMD), including non-exudative (e.g intermediate dry AMD or geographic atrophy (GA)) and exudative (e.g. wet AMD (choroidal neovascularization (CNV)) AMD, diabetic retinopathy (DR), endophthalmitis and uveitis. In one example, the complement-associated eye condition is intermediate dry AMD. In one example, the complement-associated eye condition is geographic atrophy. In one example, the complement-associated eye condition is wet AMD (choroidal neovascularization (CNV)).

BRIEF DESCRIPTION OF THE FIGURES

FIGS. 1A-1C shows the alignment of sequences of the variable light chain domains for the following: humanized anti-Factor D Fab clone #111 (SEQ ID NO: 1), humanized anti-Factor D Fabs, 238, 238-1, 238-2, 238-3, 238-4, 238-5, 238-6, 238-7, 238-8, 238-9, 238-10 and 238-11 (SEQ ID NOs: 6-17, respectively) and VL Kappa I consensus sequence (SEQ ID NO: 65). Positions are numbered according to Kabat and hypervariable regions (in accordance with Kabat+Chothia HVR definitions) are boxed (HVRs: (1) HVR-L1 identified as A1-A11 (ITSTDIDDDMN (SEQ ID NO: 30), ITSTDIDDDLN (SEQ ID NO: 31), ITSTDIDDDIN (SEQ ID NO: 32), ITSTDIDDDMA (SEQ ID NO: 33) or ITSTDIDDDMQ (SEQ ID NO: 34)), (2) HVR-L2 identified as B1-B7 (GGNTLRP (SEQ ID NO: 35), GGSTLRP (SEQ ID NO: 36) or GGATLRP (SEQ ID NO: 37)), (3) HVR-L3 identified as C1-C9 (LQSDSLPYT (SEQ ID NO: 38)). Amino acid changes in each humanized anti-Factor D Fab are bold and italicized.

FIG. 2A-C shows the alignment of sequences of the variable heavy chain domains for the following: humanized anti-Factor D Fab clone #111 (SEQ ID NO: 2) and humanized anti-Factor D Fabs, 238, 238-1, 238-2, 238-3, 238-4, 238-5, 238-6, 238-7, 238-8, 238-9, 238-10 and 238-11 (SEQ ID NOs: 18-29, respectively) and VH subgroup 7 consensus sequence (SEQ ID NO: 66). Positions are numbered according to Kabat and hypervariable regions (in accordance with Kabat+Chothia HVR definitions) are boxed (HVRs: (1) HVR-H1 identified as D1-D10 (GYTFTNYGMN (SEQ ID NO: 39), (2) HVR-H2 identified as E1-E19 (WINTYTGETTYADDFKG (SEQ ID NO: 40), (3) HVR-H3 identified as F1-F6 (EGGVNN (SEQ ID NO: 41), EGGVAN (SEQ ID NO: 42), EGGVQN (SEQ ID NO: 43), EGGVNA (SEQ ID NO: 44) or EGGVNQ (SEQ ID NO: 45)). Amino acid changes in each humanized anti-Factor D Fab are bold and italicized.

FIG. 3 shows the nucleotide sequence (SEQ ID NO: 46) of the light chain of humanized anti-Factor D Fab 238. The nucleotide sequence encodes for the light chain of humanized anti-Factor D Fab 238 with the start and stop codon shown in bold and underlined. The codon corresponding to the first amino acid in FIG. 4 (SEQ ID NO: 47) is bold and italicized.

FIG. 4 shows the amino acid sequence (SEQ ID NO: 47) of the light chain for humanized anti-Factor D Fab 238. The amino acid sequence lacks the N-terminus signal sequence of the polypeptide encoded by SEQ ID NO: 46 shown in FIG. 3. The HVR sequences are bold and italicized. Variable regions are regions not underlined while first constant domain CL1 is underlined. Framework (FR) regions and HVR regions are shown:

Figure 11:
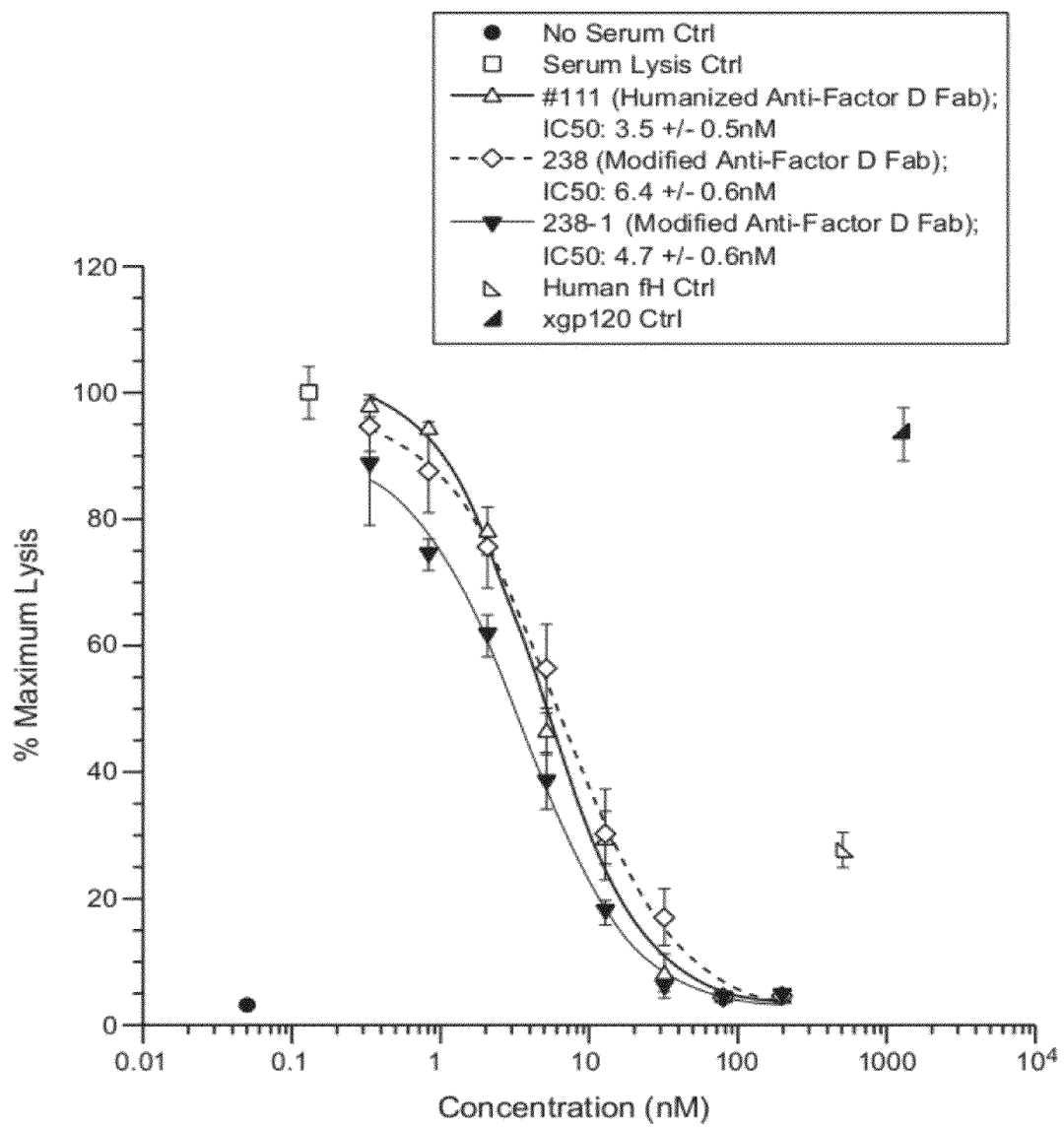

```
FR1-LC,      (SEQ ID NO: 48)
FR2-LC,      (SEQ ID NO: 49)
FR3-LC,      (SEQ ID NO: 50)
FR4-LC,      (SEQ ID NO: 51)
HVR1-LC,     (SEQ ID NO: 30, (ITSTDIDDDMN)),
HVR2-LC,     (SEQ ID NO: 35 (GGNTLRP)),
HVR3-LC      (SEQ ID NO: 38 (LQSDSLPYT))
and
CL1.         (SEQ ID NO: 52)
```

FIG. 5 shows the nucleotide sequence (SEQ ID NO: 53) of the heavy chain of humanized anti-Factor D Fab 238. The nucleotide sequence encodes for the heavy chain of humanized anti-Factor D Fab 238 with the start and stop codon shown in bold and underlined. The codon corresponding to the first amino acid in FIG. 6 (SEQ ID NO: 54) is bold and italicized.

FIG. 6 shows the amino acid sequence (SEQ ID NO: 54) of the heavy chain for humanized anti-Factor D Fab 238. The amino acid sequence lacks the N-terminus signal sequence of the polypeptide encoded by SEQ ID NO: 53 shown in FIG. 5. The HVR sequences are bold and italicized. Variable regions are regions not underlined while first constant domain CH1 is underlined. Framework (FR) regions and HVR regions are shown:

```
FR1-HC,      (SEQ ID NO: 55)
FR2-HC,      (SEQ ID NO: 56)
FR3-HC,      (SEQ ID NO: 57)
FR4-HC,      (SEQ ID NO: 58)
HVR1-HC,     (SEQ ID NO: 39 (GYTFTNYGMN))
HVR2-HC,     (SEQ ID NO: 40 (WINTYTGETTYADDFKG))
HVR3-HC      (SEQ ID NO: 41 (EGGVNN))
and
CH1.         (SEQ ID NO: 59)
```

FIG. 7 shows the nucleotide sequence (SEQ ID NO: 60) of the light chain of humanized anti-Factor D Fab 238-1. The nucleotide sequence encodes for the light chain of humanized anti-Factor D Fab 238-1 with the start and stop codon shown in bold and underlined. The codon corresponding to the first amino acid in FIG. 8 (SEQ ID NO: 61) is bold and italicized.

FIG. 8 shows the amino acid sequence (SEQ ID NO: 61) of the light chain for humanized anti-Factor D Fab 238-1. The amino acid sequence lacks the N-terminus signal sequence of the polypeptide encoded by SEQ ID NO: 60 shown in FIG. 7. The HVR sequences are bold and italicized. Variable regions are regions not underlined while first constant domain CL1 is underlined. Framework (FR) regions and HVR regions are shown:

```
FR1-LC,      (SEQ ID NO: 48)
FR2-LC,      (SEQ ID NO: 49)
FR3-LC,      (SEQ ID NO: 50)
FR4-LC,      (SEQ ID NO: 51)
HVR1-LC,     (SEQ ID NO: 30 (ITSTDIDDDMN))
HVR2-LC,     (SEQ ID NO: 35 (GGNTLRP))
HVR3-LC      (SEQ ID NO: 38 (LQSDSLPYT))
and
CL1.         (SEQ ID NO: 52)
```

FIG. 9 shows the nucleotide sequence (SEQ ID NO: 62) of the heavy chain of humanized anti-Factor D Fab 238-1. The nucleotide sequence encodes for the heavy chain of humanized anti-Factor D Fab 238-1 with the start and stop codon shown in bold and underlined. The codon corresponding to the first amino acid in FIG. 10 (SEQ ID NO: 63) is bold and italicized.

FIG. 10 shows the amino acid sequence (SEQ ID NO: 63) of the heavy chain for humanized anti-Factor D Fab 238-1. The amino acid sequence lacks the N-terminus signal sequence of the polypeptide encoded by SEQ ID NO: 62 shown in FIG. 9. The HVR sequences are bold and italicized. Variable regions are regions not underlined while first constant domain CH1 is underlined. Framework (FR) regions and HVR regions are shown:

```
FR1-HC,      (SEQ ID NO: 64)
FR2-HC,      (SEQ ID NO: 56)
FR3-HC,      (SEQ ID NO: 57)
FR4-HC,      (SEQ ID NO: 58)
HVR1-HC,     (SEQ ID NO: 39 (GYTFTNYGMN))
HVR2-HC,     (SEQ ID NO: 40 (WINTYTGETTYADDFKG))
HVR3-HC      (SEQ ID NO: 41 (EGGVNN))
and
CH1.         (SEQ ID NO: 59)
```

FIG. 11 shows the hemolytic assay results, showing inhibition of the alternative complement activity, for humanized anti-Factor D Fab clone #111 and humanized anti-Factor D Fabs 238 and 238-1. $IC_{50}$ values are shown.

Figure 12:
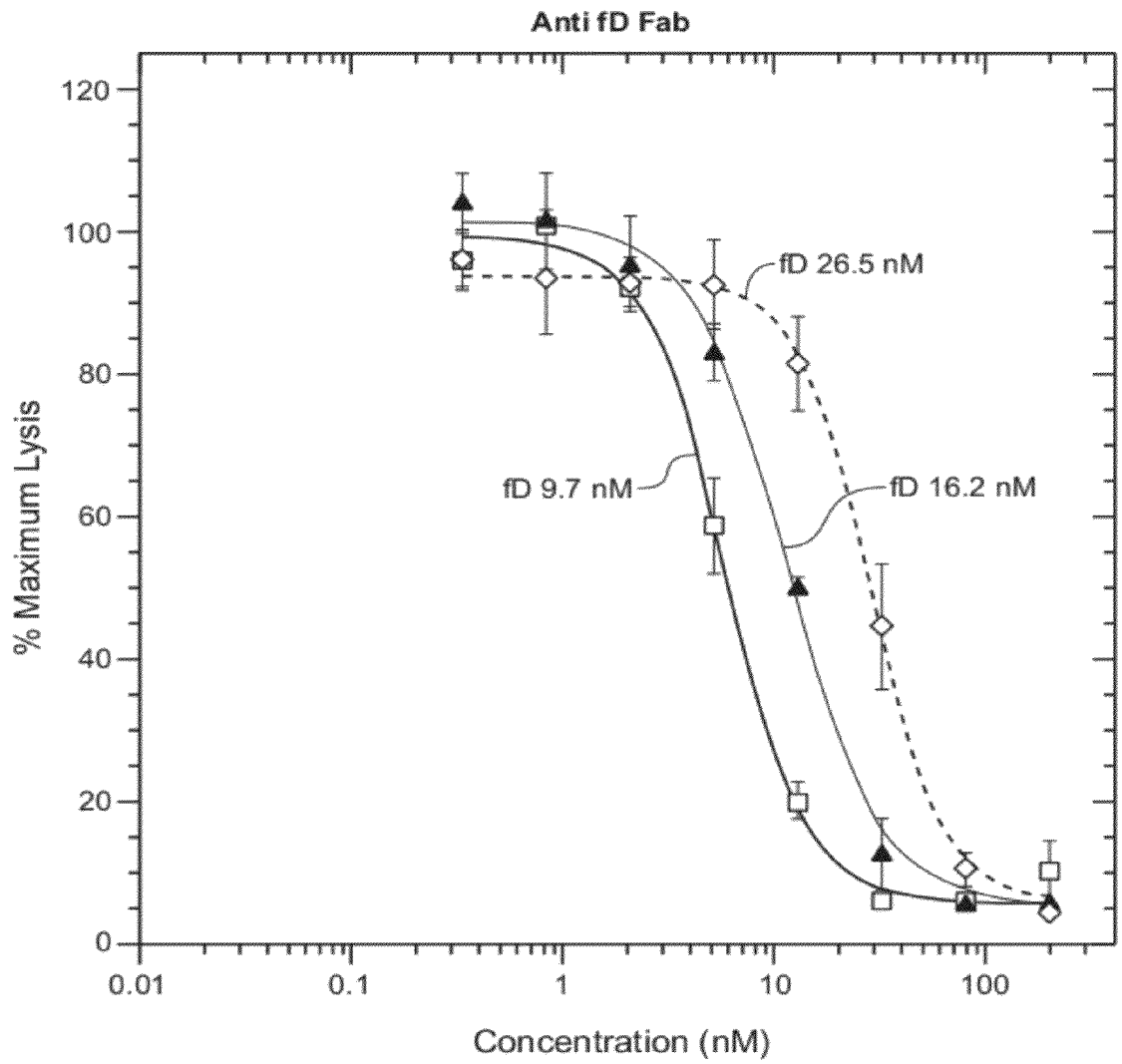

FIG. 12 shows the hemolytic assay results, showing inhibition of the alternative pathway (AP) complement activity, for humanized anti-Factor D Fab 238, at three serum concentrations (9.7 nM, 16.2 nM and 26.5 nM) of Factor D. Table 3 shows the $IC_{50}$ (nM) and $IC_{90}$ (nM) values (values represent the average of three repeated experiments), corresponding to the three serum concentrations of Factor D. The antibody to target Factor D molar ratios are also shown in Table 3.

Figure 13:
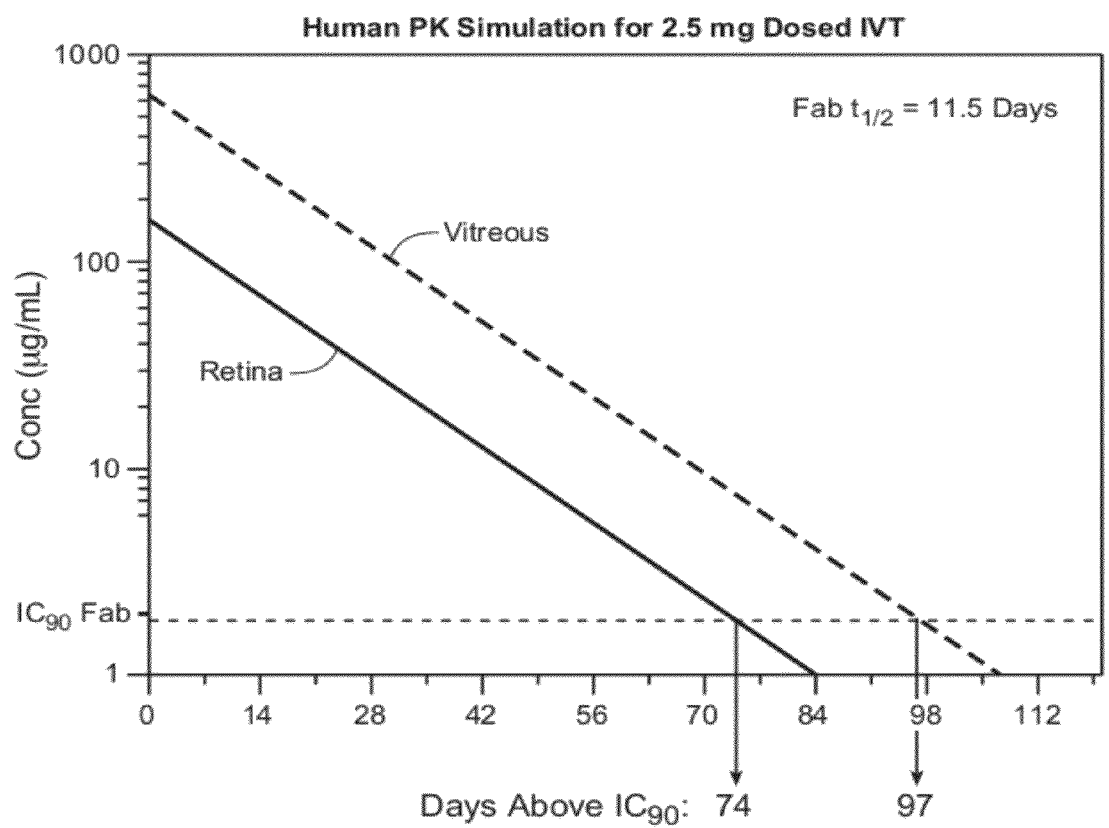

FIG. 13 shows the simulated duration of inhibition of the alternative pathway (AP) complement activation in a human eye using a single intravitreal (IVT) injection of anti-Factor D Fab 238 at a 2.5 mg dose (assuming a half-life ($t_{1/2}$) of anti-Factor D Fab 238=11.5 days, based on interspecies scaling from the rabbit). A single IVT injection of anti-Factor D Fab 238 was estimated to inhibit AP complement activation in the retinal tissue for at least about 74 days and in the vitreous humor for at least about 97 days. In FIG. 13, the dashed line shows the simulated anti-Factor D Fab 238 concentration in the vitreous humor following intravitreal administration. In FIG. 13, the solid line shows the simulated anti-Factor D Fab 238 concentration in the retinal tissue following intravitreal administration. The difference in the concentration in the vitreous humor and retinal tissue is based upon an estimate of the retinal tissue partition coefficient of 20%; in other words, 20% of the total drug administered to the vitreous humor will have access to the retinal tissue.

DETAILED DESCRIPTION OF THE INVENTION

I. Definitions

Terms used throughout this application are to be construed with ordinary and typical meaning to those of ordinary skill in the art. However, Applicants desire that the following terms be given the particular definition as defined below.

The phrase "substantially identical" with respect to an antibody chain polypeptide sequence may be construed as an antibody chain exhibiting at least 70%, or 80%, or 90% or 95% sequence identity to the reference polypeptide sequence. The term with respect to a nucleic acid sequence may be construed as a sequence of nucleotides exhibiting at least about 85%, or 90%, or 95% or 97% sequence identity to the reference nucleic acid sequence.

The term "identity" or "homology" shall be construed to mean the percentage of amino acid residues in the candidate sequence that are identical with the residue of a corresponding sequence to which it is compared, after aligning the sequences and introducing gaps, if necessary to achieve the maximum percent identity for the entire sequence, and not considering any conservative substitutions as part of the sequence identity. Neither N- or C-terminal extensions nor insertions shall be construed as reducing identity or homology. Methods and computer programs for the alignment are well known in the art. Sequence identity may be measured using sequence analysis software.

The term "antibody" is used in the broadest sense, and specifically covers monoclonal antibodies (including full length monoclonal antibodies), polyclonal antibodies, and multispecific antibodies (e.g., bispecific antibodies). Antibodies (Abs) and immunoglobulins (Igs) are glycoproteins having the same structural characteristics. While antibodies exhibit binding specificity to a specific target, immunoglobulins include both antibodies and other antibody-like molecules which lack target specificity. Native antibodies and immunoglobulins are usually heterotetrameric glycoproteins of about 150,000 daltons, composed of two identical light (L) chains and two identical heavy (H) chains. Each heavy chain has at one end a variable domain ($V_H$) followed by a number of constant domains. Each light chain has a variable domain at one end ($V_L$) and a constant domain at its other end.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In one example, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

As used herein, "anti-human Factor D antibody" means an antibody which specifically binds to human Factor D in such a manner so as to inhibit or substantially reduce complement activation.

The term "Factor D" is used herein to refer to native sequence and variant Factor D polypeptides.

A "native sequence" Factor D, is a polypeptide having the same amino acid sequence as a Factor D polypeptide derived from nature, regardless of its mode of preparation. Thus, native sequence Factor D can be isolated from nature or can be produced by recombinant and/or synthetic means. In addition to a mature Factor D protein, such as a mature human Factor D protein (NM_001928), the term "native sequence Factor D", specifically encompasses naturally-occurring precursor forms of Factor D (e.g., an inactive preprotein, which is proteolytically cleaved to produce the active form), naturally-occurring variant forms (e.g., alternatively spliced forms) and naturally-occurring allelic variants of Factor D, as well as structural conformational variants of Factor D molecules having the same amino acid sequence as a Factor D polypeptide derived from nature. Factor D polypeptides of non-human animals, including higher primates and non-human mammals, are specifically included within this definition.

"Factor D variant" means an active Factor D polypeptide as defined below having at least about 80% amino acid sequence identity to a native sequence Factor D polypeptide, such as the native sequence human Factor D polypeptide (NM_001928). Ordinarily, a Factor D variant will have at least about 80% amino acid sequence identity, or at least about 85% amino acid sequence identity, or at least about 90% amino acid sequence identity, or at least about 95% amino acid sequence identity, or at least about 98% amino acid sequence identity, or at least about 99% amino acid sequence identity with the mature human amino acid sequence (NM_001928).

"Percent (%) amino acid sequence identity" is defined as the percentage of amino acid residues in a candidate sequence that are identical with the amino acid residues in a reference Factor D sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. Sequence identity is then calculated relative to the longer sequence, i.e. even if a shorter sequence shows 100% sequence identity with a portion of a longer sequence, the overall sequence identity will be less than 100%.

"Percent (%) nucleic acid sequence identity" is defined as the percentage of nucleotides in a candidate sequence that are identical with the nucleotides in a reference Factor D-encoding sequence, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. Sequence identity is then calculated relative to the longer sequence, i.e. even if a shorter sequence shows 100% sequence identity with a portion of a longer sequence, the overall sequence identity will be less than 100%.

An "isolated" nucleic acid molecule is a nucleic acid molecule that is identified and separated from at least one contaminant nucleic acid molecule with which it is ordinarily associated in the natural source of the nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes nucleic acid molecules contained in cells that ordinarily express an encoded polypeptide where, for example, the nucleic acid molecule is in a chromosomal location different from that of natural cells.

An "isolated" Factor D polypeptide-encoding nucleic acid molecule is a nucleic acid molecule that is identified and separated from at least one contaminant nucleic acid molecule with which it is ordinarily associated in the natural source of the Factor D-encoding nucleic acid. An isolated Factor D polypeptide-encoding nucleic acid molecule is other than in the form or setting in which it is found in nature. Isolated Factor D polypeptide-encoding nucleic acid molecules therefore are distinguished from the encoding nucleic acid molecule(s) as they exists in natural cells. However, an isolated Factor D-encoding nucleic acid molecule includes Factor D-encoding nucleic acid molecules contained in cells that ordinarily express Factor D where, for example, the nucleic acid molecule is in a chromosomal location different from that of natural cells.

The term "antagonist" is used in the broadest sense, and includes any molecule that is capable of neutralizing, blocking, partially or fully inhibiting, abrogating, reducing or interfering with a Factor D biological activity. Factor D antagonists include, without limitation, anti-Factor D antibodies, and antibody variants thereof, antigen-binding fragments thereof, other binding polypeptides, peptides, and non-peptide small molecules, that bind to Factor D and are capable of neutralizing, blocking, partially or fully inhibiting, abrogating, reducing or interfering with Factor D activities, such as the ability of Factor D to participate in the pathology of a complement-associated eye condition.

A "small molecule" is defined herein to have a molecular weight below about 600, preferable below about 1000 daltons.

"Active" or "activity" or "biological activity" in the context of a Factor D antagonist of the present invention is the ability to antagonize (partially or fully inhibit) a biological activity of Factor D. One example of a biological activity of a Factor D antagonist is the ability to achieve a measurable improvement in the state, e.g. pathology, of a Factor D-associated disease or condition, such as, for example, a complement-associated eye condition. The activity can be determined in in vitro or in vivo tests, including binding assays, alternative pathway hemolysis assays (e.g. assays measuring inhibition of the alternative pathway complement activity or activation), using a relevant animal model, or human clinical trials.

The term "complement-associated disorder" is used in the broadest sense and includes disorders associated with excessive or uncontrolled complement activation. They include complement activation during cardiopulmonary bypass operations; complement activation due to ischemia-reperfusion following acute myocardial infarction, aneurysm, stroke, hemorrhagic shock, crush injury, multiple organ failure, hypobolemic shock, intestinal ischemia or other events causing ischemia. Complement activation has also been shown to be associated with inflammatory conditions such as severe burns, endotoxemia, septic shock, adult respiratory distress syndrome, hemodialysis; anaphylactic shock, severe asthma, angioedema, Crohn's disease, sickle cell anemia, poststreptococcal glomerulonephritis and pancreatitis. The disorder may be the result of an adverse drug reaction, drug allergy, IL-2 induced vascular leakage syndrome or radiographic contrast media allergy. It also includes autoimmune disease such as systemic lupus erythematosus, myasthenia gravis, rheumatoid arthritis, Alzheimer's disease and multiple sclerosis. Complement activation is also associated with transplant rejection. Complement activation is also associated with ocular diseases such as age-related macular degeneration, diabetic retinopathy and other ischemia-related retinopathies, choroidal neovascularization (CNV), uveitis, diabetic macular edema, pathological myopia, von Hippel-Lindau disease, histoplasmosis of the eye, Central Retinal Vein Occlusion (CRVO), corneal neovascularization, and retinal neovascularization.

The term "complement-associated eye condition" is used in the broadest sense and includes all eye conditions the pathology of which involves complement, including the classical and the alternative pathways, and in particular the alternative pathway of complement. Complement-associated eye conditions include, without limitation, macular degenerative diseases, such as all stages of age-related macular degeneration (AMD), including dry and wet (non-exudative and exudative) forms, choroidal neovascularization (CNV), uveitis, diabetic and other ischemia-related retinopathies, and other intraocular neovascular diseases, such as diabetic macular edema, pathological myopia, von Hippel-Lindau disease, histoplasmosis of the eye, Central Retinal Vein Occlusion (CRVO), corneal neovascularization, and retinal neovascularization. In one example, complement-associated eye conditions includes age-related macular degeneration (AMD), including non-exudative (e.g. intermediate dry AMD or geographic atrophy (GA)) and exudative (e.g. wet AMD (choroidal neovascularization (CNV)) AMD, diabetic retinopathy (DR), endophthalmitis and uveitis. In a further example, non-exudative AMD may include the presence of hard drusen, soft drusen, geographic atrophy and/or pigment clumping. In one example, complement-associated eye conditions include age-related macular degeneration (AMD), including early AMD (e.g. includes multiple small to one or more non-extensive medium sized drusen), intermediate AMD (e.g. includes extensive medium drusen to one or more large drusen) and advanced AMD (e.g. includes geographic atrophy or advanced wet AMD (CNV). (Ferris et al., AREDS Report No. 18; Sallo et al., Eye Res., 34(3): 238-40 (2009); Jager et al., *New Engl. J. Med.*, 359(1): 1735 (2008)). In a further example, intermediate dry AMD may include large confluent drusen. In a further example, geographic atrophy may include photoreceptor and/or Retinal Pigmented Epithelial (RPE) loss. In a further example, the area of geographic atrophy may be small or large and/or may be in the macula area or in the peripheral retina. In one example, complement-associated eye condition is intermediate dry AMD. In one example, complement-associated eye condition is geographic atrophy. In one example, complement-associated eye condition is wet AMD (choroidal neovascularization (CNV)).

"Treatment" is an intervention performed with the intention of preventing the development or altering the pathology of a disorder. Accordingly, "treatment" refers to both therapeutic treatment and prophylactic or preventative measures. Those in need of treatment include those already with the disorder as well as those in which the disorder is to be prevented. In treatment of an immune related disease, a therapeutic agent may directly alter the magnitude of response of a component of the immune response, or render the disease more susceptible to treatment by other therapeutic agents, e.g., antibiotics, antifungals, anti-inflammatory agents, chemotherapeutics, etc.

The "pathology" of a disease, such as a complement-associated eye condition, includes all phenomena that compromise the well-being of the patient. This includes, without limitation, abnormal or uncontrollable cell growth (neutrophilic, eosinophilic, monocytic, lymphocytic cells), antibody production, auto-antibody production, complement production, interference with the normal functioning of neighboring cells, release of cytokines or other secretory products at abnormal levels, suppression or aggravation of any inflammatory or immunological response, infiltration of inflammatory cells (neutrophilic, eosinophilic, monocytic, lymphocytic) into cellular spaces, etc.

The term "mammal" as used herein refers to any animal classified as a mammal, including, without limitation, humans, higher primates, domestic and farm animals, and zoo, sports or pet animals such horses, pigs, cattle, dogs, cats and ferrets, etc. In one embodiment of the invention, the mammal is a human.

Administration "in combination with" one or more further therapeutic agents includes simultaneous (concurrent) and consecutive administration in any order.

"Therapeutically effective amount" is the amount of a "Factor D antagonist" which is required to achieve a measurable improvement in the state, e.g. pathology, of the target disease or condition, such as, for example, a complement-associated eye condition.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature that can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology*, Wiley Interscience Publishers, (1995).

"Stringent conditions" or "high stringency conditions", as defined herein, may be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42 C; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., *Molecular Cloning: A Laboratory Manual*, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/mL denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

The term "variable" in the context of variable domain of antibodies, refers to the fact that certain portions of the variable domains differ extensively in sequence among antibodies and are used in the binding and specificity of each particular antibody for its particular target. However, the variability is not evenly distributed through the variable domains of antibodies. It is concentrated in three segments called complementarity determining regions (CDRs) also known as hypervariable regions (HVRs) both in the light chain and the heavy chain variable domains. The more highly conserved portions of variable domains are called the framework (FR). The variable domains of native heavy and light chains each comprise four FR regions, largely a adopting α-sheet configuration, connected by three CDRs, which form loops connecting, and in some cases forming part of, the α-sheet structure. The CDRs in each chain are held together in close proximity by the FR regions and, with the CDRs from the other chain, contribute to the formation of the target binding site of antibodies (see Kabat et al.). As used herein, numbering of immunoglobulin amino acid residues is done according to the immunoglobulin amino acid residue numbering system of Kabat et al., (Sequences of Proteins of Immunological Interest, National Institute of Health, Bethesda, Md. 1987), unless otherwise indicated.

The term "hypervariable region", "HVR", or "HV", when used herein refers to the regions of an antibody variable domain which are hypervariable in sequence and/or form structurally defined loops. Generally, antibodies comprise six hypervariable regions; three in the VH (H1, H2, H3), and three in the VL (L1, L2, L3). A number of hypervariable region delineations are in use and are encompassed herein. The Kabat Complementarity Determining Regions (CDRs) are based on sequence variability and are the most commonly used (Kabat et al., Sequences of *Proteins of Immunological Interest,* 5th Ed. Public Health Service, National Institutes of Health, Bethesda, Md. (1991)). Chothia refers instead to the location of the structural loops (Chothia and Lesk *J. Mol. Biol.* 196:901-917 (1987)). The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software. The "contact" hypervariable regions are based on an analysis of the available complex crystal structures. The residues from each of these hypervariable regions are noted below.

| Loop | Kabat | AbM | Chothia | Contact |
|------|-------|-----|---------|---------|
| L1 | L24-L34 | L24-L34 | L24-L34 | L30-L36 |
| L2 | L50-L56 | L50-L56 | L50-L56 | L46-L55 |
| L3 | L89-L97 | L89-L97 | L89-L97 | L89-L96 |
| H1 | H31-H35B | H26-H35B | H26-H32 . . . 34 | H30-H35B |
| | | (Kabat Numbering) | | |
| H1 | H31-H35 | H26-H35 | H26-H32 | H30-H35 |
| | | (Chothia Numbering) | | |
| H2 | H50-H65 | H50-H58 | H52-H56 | H47-H58 |
| H3 | H95-H102 | H95-H102 | H95-H102 | H93-H101 |

Hypervariable regions may comprise "extended hypervariable regions" as follows: 24-36 or 24-34 (L1), 46-56 or 50-56 (L2) and 89-97 (L3) in the VL and 26-35B (H1), 50-65, 47-65 or 49-65 (H2) and 93-102, 94-102 or 95-102 (H3) in the VH. The variable domain residues are numbered according to Kabat et al., supra for each of these definitions.

"Framework" or "FR" residues are those variable domain residues other than the hypervariable region residues or CDR residues herein defined.

The term "variable domain residue numbering as in Kabat" or "amino acid position numbering as in Kabat", and variations thereof, refers to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991). Using this numbering system, the actual linear amino acid sequence may contain fewer or additional amino acids corresponding to a shortening of, or insertion into, a FR or CDR of the variable domain. For example, a heavy chain variable domain may include a single amino acid insert (residue 52a according to Kabat) after residue 52 of H2 and inserted residues (e.g. residues 82a, 82b, and 82c, etc according to Kabat) after heavy chain FR residue 82. The Kabat numbering of residues may be determined for a given antibody by alignment at regions of homology of the sequence of the antibody with a "standard" Kabat numbered sequence.

The Kabat numbering system is generally used when referring to a residue in the variable domain (approximately residues 1-107 of the light chain and residues 1-113 of the heavy chain) (e.g, Kabat et al., Sequences of Immunological Interest. 5th Ed. Public Health Service, National Institutes of Health, Bethesda, Md. (1991), expressly incorporated herein by reference). The "EU numbering system" or "EU index" is generally used when referring to a residue in an immunoglobulin heavy chain constant region (e.g., the EU index reported in Kabat et al., supra; hinge region in constant domain of heavy chain is approximately residues 216-230 (EU numbering) of the heavy chain). The "EU index as in Kabat" refers to the residue numbering of the human IgG1 EU antibody. Unless stated otherwise herein, references to residue numbers in the variable domain of antibodies means residue numbering by the Kabat numbering system. Unless stated otherwise herein, references to residue numbers in the constant domain of antibodies means residue numbering by the EU numbering system (e.g., see U.S. Provisional Application No. 60/640, 323, Figures for EU numbering).

As used herein, "polypeptide" refers generally to peptides and proteins having more than about ten amino acids. In one example, the polypeptide is a mammalian protein, examples of which include Factor D and fragments and/or variants of Factor D. In another example, the polypeptide is a full length antibody, or antibody fragment thereof (e.g. antigen-binding fragment), that binds human Factor D, examples of which include Fab, Fab', F(ab')$_2$, and F$_v$ fragments; diabodies, linear antibodies; single-chain antibody molecules; and multispecific antibodies formed from antibody fragments (e.g. antigen-binding fragment).

A "variant" or "amino acid sequence variant" of a starting polypeptide is a polypeptide that comprises an amino acid sequence different from that of the starting polypeptide. Generally, a variant will possess at least 80% sequence identity, preferably at least 90% sequence identity, more preferably at least 95% sequence identity, and most preferably at least 98% sequence identity with the native polypeptide. Percentage sequence identity is determined for example, by the Fitch et al., *Proc. Natl. Acad. Sci. USA,* 80: 1382-1386 (1983), version of the algorithm described by Needleman et al., *J. Mol. Biol.,* 48: 443-453 (1970), after aligning the sequences to provide for maximum homology. Amino acid sequence variants of a polypeptide may be prepared by introducing appropriate nucleotide changes into DNA encoding the polypeptide, or by peptide synthesis. Such variants include, for example, deletions from, and/or insertions into and/or substitutions of, residues within the amino acid sequence of the polypeptide of interest. Any combination of deletion, insertion, and substitution is made to arrive at the final construct, provided that the final construct possesses the desired characteristics. The amino acid changes also may alter post-translational processes of the polypeptide, such as changing the number or position of glycosylation sites. Methods for generating amino acid sequence variants of polypeptides are described in U.S. Pat. No. 5,534,615, expressly incorporated herein by reference, for example.

An "antibody variant" or "modified antibody" of a starting antibody is an antibody that comprises an amino acid sequence different from that of the starting antibody, wherein one or more of the amino acid residues of the starting antibody have been modified. Generally, an antibody variant will possess at least 80% sequence identity, preferably at least 90% sequence identity, more preferably at least 95% sequence identity, and most preferably at least 98% sequence identity with the starting antibody. Percentage sequence identity is determined for example, by the Fitch et al., *Proc. Natl. Acad. Sci. USA,* 80: 1382-1386 (1983), version of the algorithm described by Needleman et al., *J. Mol. Biol.,* 48: 443-453 (1970), after aligning the sequences of the starting antibody and the candidate antibody variant to provide for maximum homology. Identity or similarity with respect to the parent sequenced is defined herein as the percentage of amino acid residues in the candidate variant sequence that are identical (i.e. same residue) or similar (i.e. amino acid residue from the same group based on common side-chain properties, see below) with the parent antibody residues, after aligning the sequences and introducing gaps, if necessary, to achieve the maximum percent sequence identity. Amino acid sequence variants of an antibody may be prepared by introducing appropriate nucleotide changes into DNA encoding the antibody, or by peptide synthesis. Such variants include, for example, deletions from, and/or insertions into and/or substitutions of, residues within the amino acid sequence of the antibody of interest. Any combination of deletion, insertion, and substitution is made to arrive at the final construct, provided that the final construct possesses the desired characteristics. The amino acid changes also may alter post-translational processes of the antibody, such as changing the number or position of glycosylation sites. Methods for generating antibody sequence variants of antibodies are similar to those for generating amino acid sequence variants of polypeptides described in U.S. Pat. No. 5,534,615, expressly incorporated herein by reference, for example.

A "deamidated" variant of a polypeptide molecule is a polypeptide wherein one or more asparagine (N or Asn) residue(s) of the original polypeptide have been converted to aspartate (D or Asp), i.e. the neutral amide side chain has been converted to a residue with an overall acidic character. Deamidation may be prevented by converting asparagines (N or Asn) to glutamine (Q or Gln) or alanine (A or Ala) or serine (S or Ser) (Amphlett, G. et al., *Pharm. Biotechnol.,* 9:1-140 (1996)).

An "oxidized" variant of a polypeptide molecule is a polypeptide wherein one or more methionine (M or Met) or tryptophan (W or Trp) residue(s) of the original polypeptide have been converted to sulfone or sulfoxide through the sulfur of methionine. Oxidation may be prevented by converting methionine (M or Met) to leucine (L or Leu) or isoleucine (I or lle) (Amphlett, G. et al., *Pharm. Biotechnol.,* 9:1-140 (1996)).

A "pyroglutamate" variant of a polypeptide molecule is a polypeptide wherein one or more glutamine (Q or Gln) residues(s) of the original polypeptide have been converted to pyroglutamate which occurs when glutamine residues, for example N-terminal glutamine residues, spontaneously cyclize resulting in pyroglutamate. Pyroglutamate conversion may be prevented by converting glutamine (Q or Gln) residue(s) to glutamate (E or Glu) (Amphlett, G. et al., *Pharm. Biotechnol.,* 9:1-140 (1996)).

The term "antibody fragment" refers to a portion of a full-length antibody, generally the target binding or variable region. Examples of antibody fragments include Fab, Fab', F(ab')$_2$ and Fv fragments. The phrase "functional fragment or analog" of an antibody is a compound having qualitative biological activity in common with a full-length antibody. For example, a functional fragment or analog of an anti-human Factor D antibody is one which can bind to Factor D in such a manner so as to prevent or substantially reduce the complement activation. As used herein, "functional fragment" with respect to antibodies, refers to Fv, F(ab) and F(ab')$_2$ fragments. An "Fv" fragment is the minimum antibody fragment which contains a complete target recognition and binding site. This region consists of a dimer of one heavy and one light chain variable domain in a tight, non-covalent association ($V_H$-$V_L$ dimer). It is in this configuration that the three CDRs of each variable domain interact to define an target binding site on the surface of the $V_H$-$V_L$ dimer. Collectively, the six CDRs confer target binding specificity to the antibody. However, even a single variable domain (or half of an Fv comprising only three CDRs specific for an target) has the ability to recognize and bind target. "Single-chain Fv" or "sFv" antibody fragments comprise the $V_H$ and $V_L$ domains of an antibody, wherein these domains are present in a single polypeptide chain. Generally, the Fv polypeptide further comprises a polypeptide linker between the $V_H$ and $V_L$ domains which enables the sFv to form the desired structure for target binding.

The Fab fragment contains the constant domain of the light chain and the first constant domain (CH1) of the heavy chain. Fab' fragments differ from Fab fragments by the addition of a few residues at the carboxyl terminus of the heavy chain CH1 domain including one or more cysteines from the antibody hinge region. F(ab') fragments are produced by cleavage of the disulfide bond at the hinge cysteines of the F(ab')$_2$ pepsin digestion product. Additional chemical couplings of antibody fragments (e.g. antigen-binding fragments) are known to those of ordinary skill in the art.

As used herein, "library" refers to a plurality of antibody or antibody fragment sequences (for example, polypeptides of the invention), or the nucleic acids that encode these sequences, the sequences being different in the combination of variant amino acids that are introduced into these sequences according to the methods of the invention.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single targetic site. Furthermore, in contrast to conventional (polyclonal) antibody preparations which typically include different antibodies directed against different determinants (epitopes), each monoclonal antibody is directed against a single determinant on the target. In addition to their specificity, monoclonal antibodies are advantageous in that they may be synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies for use with the present invention may be isolated from phage antibody libraries using the well known techniques. The parent monoclonal antibodies to be used in accordance with the present invention may be made by the hybridoma method first described by Kohler and Milstein, Nature 256, 495 (1975), or may be made by recombinant methods.

"Humanized" forms of non-human (e.g. murine) antibodies are chimeric immunoglobulins, immunoglobulin chains or fragments thereof (such as Fv, Fab, Fab', F(ab')$_2$ or other target-binding subsequences of antibodies) which contain minimal sequence derived from non-human immunoglobulin. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody may also comprise at least a portion of an immunoglobulin constant region (Fc), typically that of a human immunoglobulin template chosen.

The terms "cell", "cell line" and "cell culture" include progeny. It is also understood that all progeny may not be precisely identical in DNA content, due to deliberate or inadvertent mutations. Variant progeny that have the same function or biological property, as screened for in the originally transformed cell, are included. The "host cells" used in the present invention generally are prokaryotic or eukaryotic hosts.

The term "vector" means a DNA construct containing a DNA sequence which is operably linked to a suitable control sequence capable of effecting the expression of the DNA in a suitable host. Such control sequences include a promoter to effect transcription, an optional operator sequence to control such transcription, a sequence encoding suitable mRNA ribosome binding sites, and sequences which control the termination of transcription and translation. The vector may be a plasmid, a phage particle, or simply a potential genomic insert. Once transformed into a suitable host, the vector may replicate and function independently of the host genome, or may in some instances, integrate into the genome itself. In the present specification, "plasmid" and "vector" are sometimes used interchangeably, as the plasmid is the most commonly used form of vector. However, the invention is intended to include such other forms of vectors which serve equivalent function as and which are, or become, known in the art.

The word "label" when used herein refers to a detectable compound or composition which can be conjugated directly or indirectly to a molecule or protein, e.g., an antibody. The label may itself be detectable (e.g., radioisotope labels or fluorescent labels) or, in the case of an enzymatic label, may catalyze chemical alteration of a substrate compound or composition which is detectable.

As used herein, "solid phase" means a non-aqueous matrix to which the antibody of the present invention can adhere. Example of solid phases encompassed herein include those formed partially or entirely of glass (e.g. controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g. an affinity chromatography column).

"Phage display" is a technique by which variant polypeptides are displayed as fusion proteins to at least a portion of coat protein on the surface of phage, e.g., filamentous phage, particles. A utility of phage display lies in the fact that large libraries of randomized protein variants can be rapidly and efficiently sorted for those sequences that bind to a target antigen with high affinity. Display of peptide and protein libraries on phage has been used for screening millions of polypeptides for ones with specific binding properties. Polyvalent phage display methods have been used for displaying small random peptides and small proteins through fusions to either gene III or gene VIII of filamentous phage. Wells and Lowman (1992) Curr. Opin. Struct. Biol. 3:355-362, and references cited therein. In a monovalent phage display, a protein or peptide library is fused to a gene III or a portion thereof, and expressed at low levels in the presence of wild type gene III protein so that phage particles display one copy or none of the fusion proteins. Avidity effects are reduced relative to polyvalent phage so that sorting is on the basis of intrinsic ligand affinity, and phagemid vectors are used, which simplify DNA manipulations. Lowman and Wells (1991) Methods: A companion to Methods in Enzymology 3:205-0216.

A "phagemid" is a plasmid vector having a bacterial origin of replication, e.g., Co1E1, and a copy of an intergenic region of a bacteriophage. The phagemid may be used on any known bacteriophage, including filamentous bacteriophage and lambdoid bacteriophage. The plasmid will also generally contain a selectable marker for antibiotic resistance. Segments of DNA cloned into these vectors can be propagated as plasmids. When cells harboring these vectors are provided with all genes necessary for the production of phage particles, the mode of replication of the plasmid changes to rolling circle replication to generate copies of one strand of the plasmid DNA and package phage particles. The phagemid may form infectious or non-infectious phage particles. This term includes phagemids which contain a phage coat protein gene or fragment thereof linked to a heterologous polypeptide gene as a gene fusion such that the heterologous polypeptide is displayed on the surface of the phage particle.

A "variant Fc region" comprises an amino acid sequence which differs from that of another Fc region by virtue of at least one "amino acid modification" as herein defined. Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. The variant Fc region herein will preferably possess at least about 80% homology with a native sequence Fc region and/or with an Fc region of a parent polypeptide, and most preferably at least about 90% homology therewith, more preferably at least about 95% homology therewith. Examples of "native sequence human Fc regions" are shown in FIG. 23 of WO 00/42072 and include a native sequence human IgG1 Fc region (non-A and A allotypes); native sequence human IgG2 Fc region; native sequence human IgG3 Fc region; and native sequence human IgG4 Fc region as well as naturally occurring variants thereof. Native sequence murine Fc regions are shown in FIG. 22A of WO 00/42072.

According to this invention, "altered" FcRn binding affinity is one which has either enhanced or diminished FcRn binding activity compared to a parent polypeptide or to a polypeptide comprising a native sequence Fc region. In one example, the antibody with altered FcRn binding affinity has increased binding to FcRn at pH 6.0 and/or decreased binding to FcRn at pH 7.0. The variant which "displays increased binding" to an FcR binds at least one FcR with better affinity that the parent polypeptide. The variant which "displays decreased binding" to an FcR, binds at least one FcR with worse affinity than a parent polypeptide. The variant which binds an FcR with "better affinity" than a parent polypeptide, is one which binds an FcR with substantially better binding affinity than the parent antibody, when the amounts of polypeptide variant and parent polypeptide in the binding assay are essentially the same. For example, the polypeptide variant with improved FcR binding affinity may display from about 1.15 fold to about 100 fold, e.g from about 1.2 fold to about 50 fold improvement in FcR binding affinity compared to the parent polypeptide, where FcR binding affinity is determined.

An "amino acid modification" refers to a change in the amino acid sequence of a predetermined amino acid sequence. Exemplary modifications include an amino acid substitution, insertion and/or deletion. One example of an amino acid modification herein is a substitution.

An "amino acid modification at" a specified position, e.g. of the Fc region, refers to the substitution or deletion of the specified residues, or the insertion of at least one amino acid residues adjacent the specified residue. By insertion "adjacent" a specified residue is meant insertion within one to two residues thereof. The insertion may be N-terminal or C-terminal to the specified residue.

An "amino acid substitution" refers to the replacement of at least one existing amino acid residue in a predetermined amino acid sequence with another different "replacement" amino acid residue. The replacement residue or residues may be "naturally occurring amino acid residues" (i.e., encoded by the genetic code) and selected from the group consisting of: alanine (ala); arginine (Arg); asparagine (Asn); aspartic acid (Asp); cysteine (Cys); glutamine (Gln); glutamic acid (Glu); glycine (Gly), histidine (His); isoleucine (Ile); leucine (Leu); lysine (Lys); methionine (Met); phenylalanine (Phe); proline (Pro); serine (Ser); threonine (Thr); tryptophan (Trp); tyrosine (Tyr); and valine (Val). Substitution with one or more non-naturally occurring amino acid residues is also encompassed by the definition of an amino acid substitution herein. A "non-naturally occurring amino acid residue" refers to a residue, other than those naturally occurring amino acid residues listed above, which is able to covalently bind adjacent amino acid residue(s) in a polypeptide chain. Examples of non-naturally occurring amino acid residues include norleucine, ornithine, norvaline, homoserine and other amino acid residue analogues such as those described in Ellman et al., *Meth. Enzym*, 202: 301-336 (1991). To generate such non-naturally occurring amino acid residues, the procedures of Noren et al., *Science*, 244: 182 (1989) and Ellman et al., supra, can be used. Briefly, these procedures involve chemically activating a suppressor tRNA with a non-naturally occurring amino acid residue followed by in vitro transcription and translation of the RNA.

An "amino acid insertion" refers to the incorporation of at least one amino acid into a predetermined amino acid sequence. While the insertion will usually consist of the insertion of one or two amino acid residues, the present application contemplates larger "peptide insertions", e.g. insertion of about three to about five or even up to about ten amino acid residues. The inserted residue(s) may be naturally occurring or non-naturally occurring as disclosed above.

An "amino acid deletion" refers to the removal of at least one amino acid residue from a predetermined amino acid sequence.

II. Detailed Description

The invention herein provides Factor D antagonists, including anti-Factor D antibodies, and variants thereof, and fragments thereof (e.g. antigen-binding fragments) useful for the prevention and treatment of complement-associated conditions, including eye conditions (all eye conditions and diseases the pathology of which involves complement, including the classical and the alternative pathways, and in particular the alternative pathway of complement), such as, for example, macular degenerative diseases, such as all stages of age-related macular degeneration (AMD), including dry and wet (non-exudative and exudative) forms, choroidal neovascularization (CNV), uveitis, diabetic and other ischemia-related retinopathies, endophthalmitis, and other intraocular neovascular diseases, such as diabetic macular edema, pathological myopia, von Hippel-Lindau disease, histoplasmosis of the eye, Central Retinal Vein Occlusion (CRVO), corneal neovascularization, and retinal neovascularization. One group of complement-associated eye conditions includes age-related macular degeneration (AMD), including non-exudative (e.g. intermediate dry AMD or geographic atrophy (GA)) and exudative (e.g. wet AMD (choroidal neovascularization (CNV)) AMD, diabetic retinopathy (DR), endophthalmitis and uveitis. In one example, complement-associated eye condition is intermediate dry AMD. In one example, complement-associated eye condition is geographic atrophy. In one example, complement-associated eye condition is wet AMD (choroidal neovascularization (CNV)).

AMD is age-related degeneration of the macula, which is the leading cause of irreversible visual dysfunction in individuals over the age of 60. Two types of AMD exist, non-exudative (dry) and exudative (wet) AMD. The dry, or non-exudative, form involves atrophic and hypertrophic changes in the retinal pigment epithelium (RPE) underlying the central retina (macula) as well as deposits (drusen) on the RPE. Patients with nonexudative AMD can progress to the wet, or exudative, form of AMD, in which abnormal blood vessels called choroidal neovascular membranes (CNVMs) develop under the retina, leak fluid and blood, and ultimately cause a blinding disciform scar in and under the retina. Nonexudative AMD, which is usually a precursor of exudative AMD, is more common. The presentation of nonexudative AMD varies: hard drusen, soft drusen, RPE geographic atrophy, and pigment clumping can be present. Complement components are deposited on the RPE early in AMD and are major constituents of drusen.

1. Humanized Anti-Factor D Antibodies

The invention herein includes the production and use of humanized anti-Factor D antibodies, and fragments thereof. Exemplary methods for generating antibodies are described in more detail in the following sections.

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., *Nature*, 321:522-525 (1986); Riechmann et al., *Nature*, 332:323-327 (1988); Verhoeyen et al., *Science*, 239:1534-1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies can in some instances be important to reduce antigenicity and/or HAMA response (human anti-mouse antibody) when the antibody is intended for human therapeutic use. Reduction or elimination of a HAMA response is generally a significant aspect of clinical development of suitable therapeutic agents. See, e.g., Khaxzaeli et al., J. Natl. Cancer Inst. (1988), 80:937; Jaffers et al., Transplantation (1986), 41:572; Shawler et al., J. Immunol. (1985), 135:1530; Sears et al., J. Biol. Response Mod. (1984), 3:138; Miller et al., Blood (1983), 62:988; Hakimi et al., J. Immunol. (1991), 147:1352; Reichmann et al., Nature (1988), 332:323; Junghans et al., Cancer Res. (1990), 50:1495. As described herein, the invention provides antibodies that are humanized such that HAMA response is reduced or eliminated. Variants of these antibodies can further be obtained using routine methods known in the art, some of which are further described below. According to the so-called "best-fit" method, the sequence of the variable domain of a rodent antibody is screened against the entire library of known human variable domain sequences. The human V domain sequence which is closest to that of the rodent is identified and the human framework region (FR) within it accepted for the humanized antibody (Sims et al., *J. Immunol.* 151:2296 (1993); Chothia et al., *J. Mol. Biol.*, 196: 901 (1987)). Another method uses a particular framework region derived from the consensus sequence of all human antibodies of a particular subgroup of light or heavy chains. The same framework may be used for several different humanized antibodies (Carter et al., *Proc. Natl. Acad. Sci. USA,* 89:4285 (1992); Presta et al., *J. Immunol.* 151:2623 (1993)).

For example, an amino acid sequence from an antibody as described herein can serve as a starting (parent) sequence for diversification of the framework and/or hypervariable sequence(s). A selected framework sequence to which a starting hypervariable sequence is linked is referred to herein as an acceptor human framework. While the acceptor human frameworks may be from, or derived from, a human immunoglobulin (the VL and/or VH regions thereof), the acceptor human frameworks may be from, or derived from, a human consensus framework sequence as such frameworks have been demonstrated to have minimal, or no, immunogenicity in human patients. An "acceptor human framework" for the purposes herein is a framework comprising the amino acid sequence of a VL or VH framework derived from a human immunoglobulin framework, or from a human consensus framework. An acceptor human framework "derived from" a human immunoglobulin framework or human consensus framework may comprise the same amino acid sequence thereof, or may contain pre-existing amino acid sequence changes. Where pre-existing amino acid changes are present, preferably no more than 5 and preferably 4 or less, or 3 or less, pre-existing amino acid changes are present. In one embodiment, the VH acceptor human framework is identical in sequence to the VH human immunoglobulin framework sequence or human consensus framework sequence. In one embodiment, the VL acceptor human framework is identical in sequence to the VL human immunoglobulin framework sequence or human consensus framework sequence. A "human consensus framework" is a framework which represents the most commonly occurring amino acid residue in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al. In one embodiment, for the VL, the subgroup is subgroup kappa I as in Kabat et al. In one embodiment, for the VH, the subgroup is subgroup III as in Kabat et al.

Where the acceptor is derived from a human immunoglobulin, one may optionally select a human framework sequence that is selected based on its homology to the donor framework sequence by aligning the donor framework sequence with various human framework sequences in a collection of human framework sequences, and select the most homologous framework sequence as the acceptor. The acceptor human framework may be from or derived from human antibody germlne sequences available in the public databases.

In one embodiment, human consensus frameworks herein are from, or derived from, VH subgroup VII and/or VL kappa subgroup I consensus framework sequences.

In one embodiment, the human framework template used for generation of an anti-Factor D antibody may comprise framework sequences from a template comprising a combination of VI-4.1b+ (VH7 family) and JH4d for VH chain and/or a combination of DPK4 (Vκl family) and JK2 for VL chain.

In one embodiment, the VH acceptor human framework comprises one, two, three or all of the following framework sequences:

```
                       (amino acids 1-25 of SEQ ID NO: 2)
FR1 comprising QVQLVQSGPELKKPGASVKVSCKAS, (amino acids 36-49 of SEQ ID NO: 2)
FR2 comprising WVRQAPGQGLE, (amino acids 67-98 of SEQ ID NO: 2)
FR3 comprising RFVFSLDTSVSTAYLQISSLKAEDTAVYYCER, (amino acids 67-97 of SEQ ID NO: 2)
RFVFSLDTSVSTAYLQISSLKAEDTAVYYCE, (amino acids 67-96 of SEQ ID NO: 2)
RFVFSLDTSVSTAYLQISSLKAEDTAVYYC, (SEQ ID NO: 3)
RFVFSLDTSVSTAYLQISSLKAEDTAVYYCS,
or (SEQ ID NO: 4)
RFVFSLDTSVSTAYLQISSLKAEDTAVYYCSR, (amino acids 105-115 of SEQ ID NO: 2)
FR4 comprising WGQGTLVTVSS.
```

In one embodiment, the VL acceptor human framework may comprise one, two, three or all of the following framework sequences:

```
                       (amino acids 1-23 of SEQ ID NO: 1)
FR1 comprising DIQVTQSPSSLSASVGDRVTITC, (amino acids 35-49 of SEQ ID NO: 1)
FR2 comprising WYQQKPGKVPKLLIS, (amino acids 57-88 of SEQ ID NO: 1)
FR3 comprising GVPSRFSGSGSGTDFTLTISSLQPEDVATYYC, (amino acids 98-107 of SEQ ID NO: 1)
FR4 comprising FGQGTKLEIK,
or (SEQ ID NO: 5)
FGQGTKVEIK.
```

While the acceptor may be identical in sequence to the human framework sequence selected, whether that be from a human immunoglobulin or a human consensus framework, the present invention contemplates that the acceptor sequence may comprise pre-existing amino acid substitutions relative to the human immunoglobulin sequence or human consensus framework sequence. These pre-existing substitutions are preferably minimal; usually four, three, two or one amino acid differences only relative to the human immunoglobulin sequence or consensus framework sequence.

Hypervariable region residues of the non-human antibody are incorporated into the VL and/or VH acceptor human frameworks. For example, one may incorporate residues corresponding to the Kabat CDR residues, the Chothia hypervariable loop residues, the Abm residues, and/or contact residues. Optionally, the extended hypervariable region residues as follows are incorporated: 24-36 or 24-34 (L1), 46-56 or 50-56 (L2) and 89-97 (L3), 26-35B (H1), 50-65, 47-65 or 49-65 (H2) and 93-102, 94-102, or 95-102 (H3).

In one aspect, the invention provides an anti-Factor D antibody comprising a heavy chain variable domain comprising SEQ ID NO: 2. In one aspect, the invention provides an anti-Factor D antibody comprising a light chain variable domain comprising SEQ ID NO: 1. In one aspect, the invention provides an anti-Factor D antibody comprising a heavy chain variable domain comprising SEQ ID NO: 2 and a light chain variable domain comprising SEQ ID NO: 1. In one example, the invention provides a fragment of said anti-Factor D antibodies (e.g. antigen-binding fragments).

In one aspect, the invention provides an anti-Factor D antibody comprising a heavy chain variable domain comprising an amino acid sequence having at least 90%, 91%, 92%, 93%, 94%, 95%, 96%, 97%, 98% or 99% sequence identity to an amino acid sequence of SEQ ID NO: 2. In some embodiments, an amino acid sequence having at least 90%, 91%, 92%, 93%, 94%, 95%, 96%, 97%, 98% or 99% sequence identity contains substitutions, insertions, or deletions relative to the reference sequence, but an antibody comprising that amino acid sequence retains the ability to bind to Factor D. In some embodiments, a total of 1 to 10 amino acids have been substituted, inserted, or deleted in a sequence of SEQ ID NO: 2. In some embodiments, the substitutions, insertions or deletions occur in regions outside the HVRs (i.e., in the FRs). In some embodiments, an anti-Factor D antibody comprises a heavy chain variable domain comprising an amino acid sequence of SEQ ID NO: 2. In one example, the invention provides a fragment of said anti-Factor D antibodies (e.g. antigen-binding fragments).

In some embodiments, the invention provides an anti-Factor D antibody comprising a light chain variable domain comprising an amino acid sequence having at least 90%, 91%, 92%, 93%, 94%, 95%, 96%, 97%, 98% or 99% sequence identity to an amino acid sequence of SEQ ID NO: 1. In some embodiments, an amino acid sequence having at least 90%, 91%, 92%, 93%, 94%, 95%, 96%, 97%, 98% or 99% sequence identity contains substitutions, insertions, or deletions relative to the reference sequence, but an antibody comprising that amino acid sequence retains the ability to bind to Factor D. In some embodiments, a total of 1 to 10 amino acids have been substituted, inserted, or deleted in a sequence of SEQ ID NO: 1. In some embodiments, the substitutions, insertions or deletions occur in regions outside the HVRs (i.e., in the FRs). In some embodiments, an anti-Factor D antibody comprises a light chain variable domain comprising an amino acid sequence of SEQ ID NO: 1. In one example, the invention provides a fragment of said anti-Factor D antibodies (e.g. antigen-binding fragments).

An anti-Factor D antibody may comprise any suitable framework variable domain sequence, provided that the antibody retains the ability to bind Factor D. For example, in some embodiments, anti-Factor D antibodies of the invention comprise a heavy chain variable domain framework sequence that is a combination of VI.4.1 b+ and JH4d (See FIG. 3). In some embodiments, anti-Factor D antibodies of the invention comprise a human subgroup VII heavy chain framework consensus sequence. In some embodiments, anti-Factor D antibodies of the invention comprise a heavy chain variable domain framework sequence comprising FR1 comprising amino acids 1-25 of SEQ ID NO: 2, FR2 comprising amino acids 36-49 of SEQ ID NO: 2, FR3 comprising amino acids 67-98 of SEQ ID NO: 2 and FR4 comprising amino acids 105-115 of SEQ ID NO: 2 In one embodiment of these antibodies, the heavy chain variable domain sequence comprises substitution(s) at position 40 and/or 88 (Kabat numbering). In one embodiment of these antibodies, position 40 is cysteine (C) or alanine (A) and/or position 88 is cysteine (C) or alanine (A). In some embodiments, anti-Factor D antibodies of the invention comprise a light chain variable domain framework sequence that is a combination of DPK4 and JK2 (See FIG. 4). In some embodiments, anti-Factor D antibodies of the invention comprise a human kappa I (κI) light chain framework consensus sequence. In some embodiments, anti-Factor D antibodies of the invention comprise a light chain variable domain framework sequence comprising FR1 comprising amino acids 1-23 of SEQ ID NO: 1, FR2 comprising amino acids 35-49 of SEQ ID NO: 1, FR3 comprising amino acids 57-88 of SEQ ID NO: 1 and FR4 comprising amino acids 98-107 of SEQ ID NO: 1. In one embodiment of these antibodies, the light chain variable framework sequence comprises one or more substitution(s) at position 15, 43 and/or 104, (Kabat numbering). In one embodiment of these antibodies, position 15 is cysteine (C) or valine (V), position 43 is cysteine (C) or alanine (A), position 104 is valine (V) or leucine (L). In one example, the invention provides a fragment of said anti-Factor D antibodies (e.g. antigen-binding fragments).

Further, an anti-Factor D antibody may comprise any suitable constant domain sequence, provided that the antibody retains the ability to bind Factor D. For example, in some embodiments, anti-Factor D antibodies of the invention comprise at least a portion of a heavy chain constant domain. In one embodiment, anti-Factor D antibodies of the invention comprise a heavy chain constant domain of either one or a combination of an α, δ, ε, γ, or μ heavy chain. Depending on the amino acid sequence of the constant domain of their heavy chains ($C_H$), immunoglobulins can be assigned to different classes or isotypes. There are five classes of immunoglobulins: IgA, IgD, IgE, IgG, and IgM, having heavy chains designated α, δ, ε, γ, and μ, respectively. The γ and α classes are further divided into subclasses on the basis of relatively minor differences in $C_H$ sequence and function, e.g., humans express the following subclasses: IgG1, IgG2, IgG3, IgG4, IgA1, and IgA2. In one embodiment, anti-Factor D antibodies of the invention comprise a heavy chain constant domain comprising substitutions at amino acid positions that results in a desired effect on effector function (e.g. binding affinity). In one embodiment, anti-Factor D antibodies of the invention comprise a heavy chain constant domain comprising substitutions at amino acid positions that do not result in an effect on effector function (e.g. binding affinity). In one embodiment, anti-Factor D antibodies of the invention comprise a heavy chain constant domain of the IgG type (e.g. IgG1, IgG2, IgG3 or IgG4) and further comprise a substitution at position 114 (Kabat numbering; equivalent to 118 in EU numbering), 168 (Kabat numbering; equivalent to 172 in EU numbering), 172 (Kabat numbering; equivalent to 176 in EU numbering) and/or 228 (EU numbering). In one embodiment, anti-Factor D antibodies of the invention comprise a heavy chain constant domain of the IgG (e.g. IgG1, IgG2, IgG3 or IgG4) type and further comprise a substitution at position 114 wherein position 114 is a cysteine (C) or alanine (A), position 168 is cysteine (C) or alanine (A), position 172 is a cysteine (C) or alanine (A) and/or position 228 is a proline (P), arginine (R) or serine (S). In one example, the invention provides a fragment of said anti-Factor D antibodies (e.g. antigen-binding fragments).

Further, for example, in some embodiments, anti-Factor D antibodies of the invention comprise at least a portion of a light chain constant domain. In one embodiment, anti-Factor D antibodies of the invention comprise a light chain constant domain of either one or a combination of a kappa or a lambda light chain, as the light chain from any vertebrate species can be assigned to one of two clearly distinct types, called kappa and lambda, based on the amino acid sequences of their constant domains. In one embodiment, anti-Factor D antibodies of the invention comprise a light chain constant domain comprising substitutions at amino acid positions that results in a desired effect on effector function (e.g. binding affinity). In one embodiment, anti-Factor D antibodies of the invention comprise a light chain constant domain comprising substitutions at amino acid positions that do not result in an effect on effector function (e.g., binding affinity). In one embodiment, anti-Factor D antibodies of the invention comprise a light chain constant domain of the kappa type and further comprise a substitution at position 110, 144, 146 and/or 168 (Kabat numbering). In one embodiment, anti-Factor D antibodies of the invention comprise a light chain constant domain of the kappa type and further comprise a substitution at position 110 wherein 110 is a cysteine (C) or valine (V), at position 144 wherein 144 is a cysteine (C) or alanine (A), at position 146 wherein 146 is a isoleucine (I) or valine (V) and/or at position 168 wherein 168 is a cysteine (C) or serine (S). In one example, the invention provides a fragment of said anti-Factor D antibodies (e.g. antigen-binding fragments).

2. Modified Anti-Factor D Antibodies

The invention herein includes the production and use of modified anti-Factor D antibodies, for example modified humanized anti-Factor D antibodies, and variants thereof, and fragments thereof (e.g. antigen-binding fragments). Exemplary methods for generating modified antibodies are described in more detail in the following sections.

A parent anti-Factor D antibody, including a humanized anti-Factor D antibody, can be modified to generate modified anti-Factor D antibodies, and variants thereof. In one embodiment, the modified anti-Factor D antibodies, and variants thereof, may have improved physical, chemical, biological or homogeneity properties over the parent antibody. In one example, the invention provides a fragment of said anti-Factor D antibodies (e.g. antigen-binding fragments).

In one embodiment, an antibody of this invention comprises one or more amino acid alterations (e.g. substitutions) into one or more of the hypervariable regions of the parent antibody. Alternatively, or in addition, one or more alterations (e.g. substitutions) of framework region residues may be introduced in the parent antibody. Examples of framework region residues to modify include those which non-covalently bind antigen directly (Amit et al., (1986) *Science,* 233: 747-753); interact with/effect the conformation of a CDR (Chothia et al. (1987) *J. Mol. Biol.,* 196: 901-917), and/or participate in the $V_L$-$V_H$ interface (EP 239 400B1). In certain embodiments, modification of one or more of such framework region residues results in an enhancement of the binding affinity of the antibody for the antigen. For example, from about one to about 5 framework residues may be altered in this embodiment of the invention. Examples of framework or HVR region residues to modify include sites, wherein modifications at such sites result in the generation of deamidated variants (for example, asparagine (N or Asn) residue(s) modified to aspartate (D or Asp), oxidation variants (for example, methionine (M or Met) residue(s) and/or tryptophan (W or Trp) residue(s) modified to sulfone or sulfoxide) or pyroglutamate variants (for example, glutamine (Q or Gln) residue(s) modified to pyroglutamate). Examples of framework region residues or HVR region residues to modify include possible deamidation sites (i.e. asparagine (N or Asn)), oxidation sites (i.e. methionine (M or Met) or tryptophan (W or Trp)) or pyroglutamate conversion sites (i.e. glutamine (Q or Gln)), wherein modification at such sites prevent deamidation and/or oxidation and/or pyroglutamate conversion, respectively. To prevent the formation of deamidated variants, asparagine (N or Asn) may be mutated to alanine (A or Ala), glutamine (Q or Gln) or serine (S or Ser). To prevent the formation of oxidated variants, methionine (Met) or tryptophan (W or Trp) may be mutated to leucine (L) or isoleucine (I). To prevent the formation of pyroglutamate variants, glutamine (Q or Gln) may be mutated to glutamate (E or Glu). (Amphlett, G. et al., *Pharm. Biotechnol.,* 9:1-140 (1996)). Alternatively, or in addition, one or more alterations (e.g. substitutions) of framework region residues may be in the Fc region in the parent antibody. In one example, the invention provides a fragment of said anti-Factor D antibodies (e.g. antigen-binding fragments).

In one embodiment, an antibody of this invention comprises a variant Fc region such that the half-life of the antibody in vivo is increased or decreased relative to the parent antibody or the antibody comprising a native sequence Fc region. In one embodiment, the antibody comprises an variant Fc region that increases or decreases neonatal Fc receptor (FcRn) binding affinity to the antibody (see WO2000042072, incorporated by reference in its entirety). For example, such antibody can comprise an amino acid modification at any one or more of amino acid positions 238, 252, 253, 254, 255, 256, 265, 272, 286, 288, 303, 305, 307, 309, 311, 312, 317, 340, 356, 360, 362, 376, 378, 380, 382, 386, 388, 400, 413, 415, 424, 433, 434, 435, 436, 439 or 447 of the Fc region, wherein the numbering of the residues in the Fc region is that of the EU index as in Kabat. Such polypeptide variants with reduced binding to an FcRn may comprise an amino acid modification at any one or more of amino acid positions 252, 253, 254, 255, 288, 309, 386, 388, 400, 415, 433, 435, 436, 439 or 447 of the Fc region, wherein the numbering of the residues in the Fc region is that of the EU index as in Kabat. The above-mentioned polypeptide variants may, alternatively, display increased binding to FcRn and comprise an amino acid modification at any one or more of amino acid positions 238, 256, 265, 272, 286, 303, 305, 307, 311, 312, 317, 340, 356, 360, 362, 376, 378, 380, 382, 413, 424 or 434 of the Fc region, wherein the numbering of the residues in the Fc region is that of the EU index as in Kabat. For example, the antibody comprises a variant Fc region that binds with increased half-life in vivo relative to the parent antibody or the antibody comprising a native sequence Fc region. For example, the antibody comprises a variant Fc region that binds with increased affinity to FcRn relative to the parent antibody or the antibody comprising a native sequence Fc region.

FcRn Binding Affinity May be Measured as Follows

The binding of antibodies of this invention against human FcRn can be studied by surface plasmon resonance using, for example, a BiaCore 3000 instrument. Human FcRn is coupled to a sensor chip using an amine coupling kit. For example, a CM5 sensor chip can be activated with EDC/NHS for 7 min at 5 μl/min. 100 μg/ml of human FcRn can be injected for 30 sec to 2 min at a flow rate of 10 μl/min over the activated chip to give a final binding response unit (RU) of 100 to 200. After conjugation, the FcRn coupled chip can be blocked by an injection of 35 µl of 1M ethanolamine hydrochloride at 5 µl/min.

The binding of the antibodies of this invention to human FcRn at pH 6.0 or pH 7.4 can be determined. The running buffer for the binding experiment is either PBS pH 6.0 or pH 7.4 containing 0.01% P20 and 0.02% sodium azide. Antibodies of this invention can be buffer-exchanged into either pH 6.0 or pH 7.4 running buffer. In one embodiment, the experiments are performed at 25° C. For the pH 6.0 run, antibodies, with concentrations ranging from 4 µM to 0.7 nM, are flowed over an FcRn coated chip at 30 µl/min for 4 min and then are allowed to dissociate from the chip for 5 min. For the pH 7.4 run, antibodies, with concentrations ranging from 12 µM to 100 nM, are injected over the FcRn coated chip at 20 µl/min for 1.5 min and then released for 2 min. Antibodies are also flowed over an unconjugated spot on the sensor chip to allow subtraction of background non-specific binding from the binding to FcRn-coupled chip. Chip can be regenerated with 30 sec pulse of 0.1M TRIS pH 8.3 in between injections. Steady state RU for each injection can be recorded at the end of each injection phase, and dissociation constants ($K_D$) are later calculated by plotting the steady state RU against injection concentration.

One useful procedure for generating such modified antibodies, and fragments thereof (e.g. antigen-binding fragments) and variants thereof, is called "alanine scanning mutagenesis" (Cunningham and Wells (1989) Science 244: 1081-1085). Here, one or more of the hypervariable region residue(s) are replaced by alanine or polyalanine residue(s) to affect the interaction of the amino acids with the antigen. Those hypervariable region residue(s) demonstrating functional sensitivity to the substitutions then are refined by introducing further or other mutations at or for the sites of substitution. Thus, while the site for introducing an amino acid sequence variation is predetermined, the nature of the mutation per se need not be predetermined. The ala-mutants produced this way are screened for their biological activity (i.e. binding affinity or hemolysis assay) as described herein.

Normally one would start with a conservative substitution such as those shown below under the heading of "preferred substitutions". If such substitutions result in a change in biological activity (e.g. binding affinity), then more substantial changes, denominated "exemplary substitutions" in the following table, or as further described below in reference to amino acid classes, are introduced and the products screened. Preferred substitutions are listed in the table below.

TABLE 1

Preferred Substitutions

| Original Residue | Exemplary Substitutions | Preferred Substitutions |
| --- | --- | --- |
| Ala (A) | val; leu; ile | val |
| Arg (R) | lys; gln; asn | lys |
| Asn (N) | gln; his; lys; arg | gln |
| Asp (D) | Glu | glu |
| Cys (C) | Ser | ser |
| Gln (Q) | Asn | asn |
| Glu (E) | Asp | asp |
| Gly (G) | pro; ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | leu |
| Pro (P) | Ala | ala |
| Ser (S) | Thr | thr |
| Thr (T) | Ser | ser |
| Trp (W) | tyr; phe | tyr |
| Tyr (Y) | trp; phe; thr; ser | phe |
| Val (V) | ile; leu; met; phe; ala; norleucine | leu |

Even more substantial modifications in the antibodies or fragments thereof (e.g. antigen-binding fragments) biological properties are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr, asn, gln;
(3) acidic: asp, glu;
(4) basic: his, lys, arg;
(5) residues that influence chain orientation: gly, pro; and
(6) aromatic: trp, tyr, phe.

Non-conservative substitutions will entail exchanging a member of one of these classes for another class.

In another embodiment, the sites selected for modification are modified, and those modifications with improved binding affinity are selected by phage display.

Nucleic acid molecules encoding amino acid sequence mutants or modified amino acid sequences are prepared by a variety of methods known in the art. These methods include, but are not limited to, oligonucleotide-mediated (or site-directed) mutagenesis, PCR mutagenesis, and cassette mutagenesis of an earlier prepared variant or a non-variant version of the parent antibody. One method for making mutants or variants or modified amino acid sequences is site directed mutagenesis (see, e.g., Kunkel (1985) Proc. Natl. Acad. Sci. USA 82:488).

In certain embodiments, the modified antibody will only have a single hypervariable region residue substituted. In other embodiments, two or more of the hypervariable region residues of the parent antibody will have been substituted, e.g. from about two to about ten hypervariable region substitutions. In one example, the invention provides a fragment of said anti-Factor D antibodies (e.g. antigen-binding fragments).

Ordinarily, the modified antibody will have an amino acid sequence having at least 75% amino acid sequence identity or similarity (defined above in Definition section) with the amino acid sequence of either the heavy or light chain variable domain of the parent antibody, more preferably at least 80%, more preferably at least 85%, more preferably at least 90%, and most preferably at least 95%. In one example, the invention provides a fragment of said anti-Factor D antibodies (e.g. antigen-binding fragments).

Following production of the modified antibody, or fragment thereof (e.g. antigen-binding fragment) the biological activity of that molecule relative to the parent antibody, or fragment thereof (e.g. antigen-binding fragment) is determined. As noted above, this may involve determining the binding affinity and/or other biological activities of the antibody variant, or fragment thereof (e.g. antigen-binding fragment). In one embodiment of the invention, a panel of modified antibodies, or fragments thereof (e.g. antigen-binding fragments) is prepared and screened for binding affinity for the antigen such as Factor D or a fragment thereof. One or more of the antibody mutants or modified antibodies, or fragments thereof (e.g. antigen-binding fragments) selected from this initial screen are optionally subjected to one or more further biological activity assays to confirm that the antibody variant(s), or fragments thereof (e.g. antigen-binding fragments) are indeed useful, e.g. for preclinical studies.

The modified anti-Factor D antibodies, or fragments thereof (e.g. antigen-binding fragments) described herein may be subjected to further modifications, oftentimes depending on the intended use of the modified antibody, or fragment thereof (e.g. antigen-binding fragment). Such modifications may involve further alteration of the amino acid sequence, fusion to heterologous polypeptide(s) and/or covalent modifications such as those elaborated below. With respect to amino acid sequence alterations, exemplary modifications are elaborated above. For example, any cysteine residue not involved in maintaining the proper conformation of the modified antibody also may be substituted, generally with serine, to improve the oxidative stability of the molecule and prevent aberrant cross linking. Conversely, cysteine bond(s) may be added to the antibody to improve its stability (particularly where the antibody is an antibody fragment such as an Fv fragment). Another type of amino acid mutant has an altered glycosylation pattern. This may be achieved by deleting one or more carbohydrate moieties found in the antibody, and/or adding one or more glycosylation sites that are not present in the antibody. Glycosylation of antibodies, or antibody fragments (e.g. antigen-binding fragments) is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

In one embodiment, the invention provides a modified anti-Factor D antibody, of a parent anti-Factor D antibody of the application, wherein the modified anti-Factor D antibody comprises the amino acid sequence of such parent anti-Factor D antibody of the application, wherein at least one position (according to Kabat numbering) of the amino acid sequence of such parent anti-Factor D antibody of the application is substituted with one or more of the following:
(a) amino acid at position 33 of the light chain is L or I;
(b) amino acid at position 34 of the light chain is A or Q;
(c) amino acid at position 52 of the light chain is S or A;
(d) amino acid at position 104 of the light chain is V.

In one example, the invention provides a fragment of said anti-Factor D antibody (e.g. antigen-binding fragment).

In one embodiment, the invention provides a modified anti-Factor D antibody of a parent anti-Factor D antibody of the application, wherein the modified anti-Factor D antibody variant comprises the amino acid sequence of such parent anti-Factor D antibody of the application, wherein at least one position (according to Kabat numbering) of the amino acid sequence of such parent anti-Factor D antibody of the application is substituted with one or more of the following:
(a) amino acid at position 1 of the heavy chain is E;
(b) amino acid at position 99 of the heavy chain is A or Q; or
(c) amino acid at position 100 of the heavy chain is A or Q.

In one example, the invention provides a fragment of said anti-Factor D antibody (e.g. antigen-binding fragment).

In one embodiment, the invention provides a modified anti-Factor D antibody of a parent anti-Factor D antibody of the application, wherein the modified anti-Factor D antibody comprises the amino acid sequence of such parent anti-Factor D antibody of the application, wherein at least one position (according to Kabat numbering) of the amino acid sequence of such parent anti-Factor D antibody of the application is substituted with one or more of the following:
(a) amino acid at position 33 of the light chain is L or I;
(b) amino acid at position 34 of the light chain is A or Q;
(c) amino acid at position 52 of the light chain is S or A;
(d) amino acid at position 104 of the light chain is V;
(e) amino acid at position 1 of the heavy chain is E;
(f) amino acid at position 99 of the heavy chain is A or Q; or
(g) amino acid at position 100 of the heavy chain is A or Q.

In one example, the invention provides a fragment of said anti-Factor D antibody (e.g. antigen-binding fragment).

In one embodiment, the invention provides a modified anti-Factor D antibody of a parent anti-Factor D antibody of the application, wherein the modified anti-Factor D antibody comprises the amino acid sequence of such parent anti-Factor D antibody of the application, wherein at least two positions (according to Kabat numbering) of the amino acid sequence of such parent anti-Factor D antibody of the application is substituted with one or more of the following:
(a) amino acid at position 33 of the light chain is L or I;
(b) amino acid at position 34 of the light chain is A or Q;
(c) amino acid at position 52 of the light chain is S or A;
(d) amino acid at position 104 of the light chain is V.

In one embodiment, the invention provides a modified anti-Factor D antibody of a parent anti-Factor D antibody of the application, wherein the modified anti-Factor D antibody comprises the amino acid sequence of such parent anti-Factor D antibody of the application, wherein at least two positions (according to Kabat numbering) of the amino acid sequence of such parent anti-Factor D antibody of the application is substituted with one or more of the following:
(a) amino acid at position 1 of the heavy chain is E;
(b) amino acid at position 99 of the heavy chain is A or Q; or
(c) amino acid at position 100 of the heavy chain is A or Q.

In one example, the invention provides a fragment of said anti-Factor D antibody (e.g. antigen-binding fragment).

In one embodiment, the invention provides a modified anti-Factor D antibody of a parent anti-Factor D antibody of the application, wherein the modified anti-Factor D antibody comprises the amino acid sequence of such parent anti-Factor D antibody of the application, wherein at least two positions (according to Kabat numbering) of the amino acid sequence of such parent anti-Factor D antibody of the application is substituted with one or more of the following:
(a) amino acid at position 33 of the light chain is L or I;
(b) amino acid at position 34 of the light chain is A or Q;
(c) amino acid at position 52 of the light chain is S or A;
(d) amino acid at position 104 of the light chain is V;
(e) amino acid at position 1 of the heavy chain is E;
(f) amino acid at position 99 of the heavy chain is A or Q; or
(g) amino acid at position 100 of the heavy chain is A or Q.

In one example, the invention provides a fragment of said anti-Factor D antibody (e.g. antigen-binding fragment).

In one embodiment, the invention provides a modified anti-Factor D antibody of a parent anti-Factor D antibody of the application, wherein the modified anti-Factor D antibody comprises the amino acid sequence of such parent anti-Factor D antibody of the application, wherein at least three positions (according to Kabat numbering) of the amino acid sequence of such parent anti-Factor D antibody of the application is substituted with one or more of the following:
(a) amino acid at position 33 of the light chain is L or I;
(b) amino acid at position 34 of the light chain is A or Q;
(c) amino acid at position 52 of the light chain is S or A;
(d) amino acid at position 104 of the light chain is V.

In one example, the invention provides a fragment of said anti-Factor D antibody (e.g. antigen-binding fragment).

In one embodiment, the invention provides a modified anti-Factor D antibody of a parent anti-Factor D antibody of the application, wherein the modified anti-Factor D antibody comprises the amino acid sequence of such parent anti-Factor D antibody of the application, wherein at least three positions (according to Kabat numbering) of the amino acid sequence of such parent anti-Factor D antibody of the application is substituted with one or more of the following:
(a) amino acid at position 1 of the heavy chain is E;
(b) amino acid at position 99 of the heavy chain is A or Q; or
(c) amino acid at position 100 of the heavy chain is A or Q.

In one example, the invention provides a fragment of said anti-Factor D antibody (e.g. antigen-binding fragment).

In one embodiment, the invention provides a modified anti-Factor D antibody of a parent anti-Factor D antibody of the application, wherein the modified anti-Factor D antibody comprises the amino acid sequence of such parent anti-Factor D antibody of the application, wherein at least three positions (according to Kabat numbering) of the amino acid sequence of such parent anti-Factor D antibody of the application is substituted with one or more of the following:
(a) amino acid at position 33 of the light chain is L or I;
(b) amino acid at position 34 of the light chain is A or Q;
(c) amino acid at position 52 of the light chain is S or A;
(d) amino acid at position 104 of the light chain is V;
(e) amino acid at position 1 of the heavy chain is E;
(f) amino acid at position 99 of the heavy chain is A or Q; or
(g) amino acid at position 100 of the heavy chain is A or Q.

In one example, the invention provides a fragment of said anti-Factor D antibody (e.g. antigen-binding fragment).

In one embodiment, the invention provides an anti-Factor D antibody comprising light chain HVRs of a reference antibody, wherein said anti-Factor D antibody further comprises a substitution at one or more positions of said reference antibody, wherein said reference antibody comprises light chain HVR-1 comprising ITSTDIDDDMN (SEQ ID NO: 30), light chain HVR-2 comprising GGNTLRP (SEQ ID NO: 35), and light chain HVR-3 comprising LQSDSLPYT (SEQ ID NO: 38), and wherein said substitution is one or more of the following:
(a) amino acid at position 33 of the light chain is L or I;
(b) amino acid at position 34 of the light chain is A or Q;
(c) amino acid at position 52 of the light chain is S or A;
(d) amino acid at position 104 of the light chain is V;
(e) amino acid at position 1 of the heavy chain is E;
(f) amino acid at position 99 of the heavy chain is A or Q; or
(g) amino acid at position 100 of the heavy chain is A or Q.

In one example, the invention provides a fragment of said anti-Factor D antibody (e.g. antigen-binding fragment).

In one embodiment, the invention provides an anti-Factor D antibody comprising heavy chain HVRs of a reference antibody, wherein said anti-Factor D antibody further comprises a substitution at one or more positions of said reference antibody, wherein said reference antibody comprises heavy chain HVR-1 comprising GYTFTNYGMN (SEQ ID NO: 39), heavy chain HVR-2 comprising WINTYTGETTYADDFKG (SEQ ID NO: 40), and heavy chain HVR-3 comprising EGGVNN (SEQ ID NO: 41), and wherein said substitution is one or more of the following:
(a) amino acid at position 33 of the light chain is L or I;
(b) amino acid at position 34 of the light chain is A or Q;
(c) amino acid at position 52 of the light chain is S or A;
(d) amino acid at position 104 of the light chain is V';
(e) amino acid at position 1 of the heavy chain is E;
(f) amino acid at position 99 of the heavy chain is A or Q; or
(g) amino acid at position 100 of the heavy chain is A or Q.

In one example, the invention provides a fragment of said anti-Factor D antibody (e.g. antigen-binding fragment).

In one embodiment, the invention provides an anti-Factor D antibody comprising light chain HVRs and heavy chain HVRs of a reference antibody, wherein said anti-Factor D antibody further comprises a substitution at one or more positions of said reference antibody, wherein said reference antibody comprises light chain HVR-1 comprising ITSTDIDDDMN (SEQ ID NO: 30), light chain HVR-2 comprising GGNTLRP (SEQ ID NO: 35), and light chain HVR-3 comprising LQSDSLPYT (SEQ ID NO: 38), and heavy chain HVR-1 comprising GYTFTNYGMN (SEQ ID NO: 39), heavy chain HVR-2 comprising WINTYTGETTYADDFKG (SEQ ID NO: 40), and heavy chain HVR-3 comprising EGGVNN (SEQ ID NO: 41), and wherein said substitution is one or more of the following:
(a) amino acid at position 33 of the light chain is L or I;
(b) amino acid at position 34 of the light chain is A or Q;
(c) amino acid at position 52 of the light chain is S or A;
(d) amino acid at position 104 of the light chain is V;
(e) amino acid at position 1 of the heavy chain is E;
(f) amino acid at position 99 of the heavy chain is A or Q; or
(g) amino acid at position 100 of the heavy chain is A or Q.

In one example, the invention provides a fragment of said anti-Factor D antibody (e.g. antigen-binding fragment).

In one aspect, the invention provides a modified anti-Factor D antibody comprising:
(a) at least one, two, three, four, five or six HVRs selected from:
(i) an HVR-H1 comprising an amino acid sequence having at least 90%, 91%, 92%, 93%, 94%, 95%, 96%, 97%, 98% or 99% sequence identity to an amino acid sequence selected from SEQ ID NO: 39;
(ii) an HVR-H2 comprising an amino acid sequence having at least 90%, 91%, 92%, 93%, 94%, 95%, 96%, 97%, 98% or 99% sequence identity to an amino acid sequence selected from SEQ ID NO: 40;

(iii) an HVR-H3 comprising an amino acid sequence having at least 90%, 91%, 92%, 93%, 94%, 95%, 96%, 97%, 98% or 99% sequence identity to an amino acid sequence selected from SEQ ID NO: 41, SEQ ID NO: 42, SEQ ID NO: 43, SEQ ID NO: 44 and SEQ ID NO: 45;

(iv) an HVR-L1 comprising an amino acid sequence having at least 90%, 91%, 92%, 93%, 94%, 95%, 96%, 97%, 98% or 99% sequence identity to an amino acid sequence selected from SEQ ID NO: 30, SEQ ID NO: 31, SEQ ID NO: 32, SEQ ID NO: 33 and SEQ ID NO: 34;

(v) an HVR-L2 comprising an amino acid sequence having at least 90%, 91%, 92%, 93%, 94%, 95%, 96%, 97%, 98% or 99% sequence identity to an amino acid sequence selected from SEQ ID NO: 35, SEQ ID NO: 36 and SEQ ID NO: 37; and (vi) an HVR-L3 comprising an amino acid sequence having at least 90%, 91%, 92%, 93%, 94%, 95%, 96%, 97%, 98% or 99% sequence identity to an amino acid sequence selected from SEQ ID NO: 38; or (b) at least one variant HVR, wherein the variant HVR comprises modification of at least one residue of the sequence depicted in SEQ ID NO: 39, 40, 41, 42, 43, 44, 45, 30, 31, 32, 33, 34, 35, 36, 37 or 38.

In one example, the invention provides a fragment of said anti-Factor D antibody (e.g. antigen-binding fragment).

In some embodiments, an HVR having an amino acid sequence having at least 90%, 91%, 92%, 93%, 94%, 95%, 96%, 97%, 98% or 99% sequence identity contains substitutions, insertions, or deletions relative to the reference sequence, but an antibody comprising that amino acid sequence retains the ability to bind to Factor D. In some embodiments, a total of 1 to 10 amino acids have been substituted, inserted, or deleted in the reference sequence selected from the group consisting of SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37 and SEQ ID NO: 38.

In one aspect, the invention provides a modified anti-Factor D antibody comprising:

(a) at least one, two, three, four, five or six HVRs selected from:

(i) an HVR-H1 comprising the amino acid sequence selected from SEQ ID NO: 39;

(ii) an HVR-H2 comprising the amino acid sequence of SEQ ID NO: 40;

(iii) an HVR-H3 comprising the amino acid sequence selected from SEQ ID NO: 41, SEQ ID NO: 42, SEQ ID NO: 43, SEQ ID NO: 44 and SEQ ID NO: 45;

(iv) an HVR-L1 comprising the amino acid sequence selected from SEQ ID NO: 30, SEQ ID NO: 31, SEQ ID NO: 32, SEQ ID NO: 33 and SEQ ID NO: 34;

(v) an HVR-L2 comprising the amino acid sequence selected from SEQ ID NO: 35, SEQ ID NO: 36 and SEQ ID NO: 37; and (vi) an HVR-L3 comprising the amino acid sequence selected from SEQ ID NO: 38; or (b) at least one variant HVR, wherein the variant HVR comprises modification of at least one residue of the sequence depicted in SEQ ID NO: 39, 40, 41, 42, 43, 44, 45, 30, 31, 32, 33, 34, 35, 36, 37 or 38.

In one example, the invention provides a fragment of said anti-Factor D antibody (e.g. antigen-binding fragment).

In one embodiment, the invention provides a modified anti-Factor D antibody comprising an HVR-H1 comprising the amino acid sequence of SEQ ID NO: 39. In another embodiment, the invention provides a modified anti-Factor D antibody comprising an HVR-H2 comprising the amino acid sequence of SEQ ID NO: 40. In another embodiment, the invention provides a modified anti-Factor D antibody comprising an HVR-H3 comprising the amino acid sequence of SEQ ID NO: 41. In another embodiment, the invention provides a modified anti-Factor D antibody comprising an HVR-L1 comprising the amino acid sequence of SEQ ID NO: 30. In another embodiment, the invention provides a modified anti-Factor D antibody comprising an HVR-L2 comprising the amino acid sequence of SEQ ID NO: 35. In another embodiment, the invention provides a modified anti-Factor D antibody comprising the amino acid sequence of SEQ ID NO: 38. In one example, the invention provides a fragment of said anti-Factor D antibodies (e.g. antigen-binding fragments).

In another embodiment, the invention provides a modified anti-Factor D antibody comprising an HVR-H1 comprising the amino acid sequence of SEQ ID NO: 39, an HVR-H2 comprising the amino acid sequence of SEQ ID NO: 40, and an HVR-H3 comprising the amino acid sequence of SEQ ID NO: 41. In one example, the invention provides a fragment of said anti-Factor D antibody (e.g. antigen-binding fragment).

In another embodiment, the invention provides a modified anti-Factor D antibody comprising an HVR-L1 comprising the amino acid sequence of SEQ ID NO: 30, an HVR-L2 comprising the amino acid sequence of SEQ ID NO: 35, and an HVR-L3 comprising the amino acid sequence of SEQ ID NO: 38. In one example, the invention provides a fragment of said anti-Factor D antibody (e.g. antigen-binding fragment).

In another embodiment, the invention provides a modified anti-Factor D antibody comprising an HVR-H1 comprising the amino acid sequence of SEQ ID NO: 39, an HVR-H2 comprising the amino acid sequence of SEQ ID NO: 40, an HVR-H3 comprising the amino acid sequence of SEQ ID NO: 41, an HVR-L1 comprising the amino acid sequence of SEQ ID NO: 30, an HVR-L2 comprising the amino acid sequence of SEQ ID NO: 35, and an HVR-L3 comprising the amino acid sequence of SEQ ID NO: 38. In one example, the invention provides a fragment of said anti-Factor D antibody (e.g. antigen-binding fragment).

In one aspect, the invention provides a modified anti-Factor D antibody comprising a heavy chain variable domain comprising an amino acid sequence having at least 90%, 91%, 92%, 93%, 94%, 95%, 96%, 97%, 98% or 99% sequence identity to an amino acid sequence selected from the group consisting of SEQ ID NO: 18, 19, 20, 21, 22, 23, 24, 25, 26, 27, 28 and 29. In some embodiments, an amino acid sequence having at least 90%, 91%, 92%, 93%, 94%, 95%, 96%, 97%, 98% or 99% sequence identity contains substitutions, insertions, or deletions relative to the reference sequence, but an antibody comprising that amino acid sequence retains the ability to bind to Factor D. In some embodiments, a total of 1 to 10 amino acids have been substituted, inserted, or deleted in a sequence selected from the group consisting of SEQ ID NO: 18, 19, 20, 21, 22, 23, 24, 25, 26, 27, 28 and 29. In some embodiments, the substitutions, insertions or deletions occur in regions outside the HVRs (i.e., in the FRs). In some embodiments, a modified anti-Factor D antibody comprises a heavy chain variable domain comprising an amino acid sequence selected from the group consisting of SEQ ID NO: 18, 19, 20, 21, 22, 23, 24, 25, 26, 27, 28 and 29. In one example, the invention provides a fragment of said anti-Factor D antibodies (e.g. antigen-binding fragments).

In one aspect, the invention provides a modified anti-Factor D antibody comprising a light chain variable domain comprising an amino acid sequence having at least 90%, 91%, 92%, 93%, 94%, 95%, 96%, 97%, 98% or 99% sequence identity to an amino acid sequence selected from the group consisting of SEQ ID NO: 6, 7, 8, 9, 10, 11, 12, 13, 14, 15, 16 and 17. In some embodiments, an amino acid sequence having at least 90%, 91%, 92%, 93%, 94%, 95%, 96%, 97%, 98% or 99% sequence identity contains substitutions, insertions, or deletions relative to the reference sequence, but an antibody comprising that amino acid sequence retains the ability to bind to Factor D. In some embodiments, a total of 1 to 10 amino acids have been substituted, inserted, or deleted in a sequence selected from the group consisting of SEQ ID NO: 6, 7, 8, 9, 10, 11, 12, 13, 14, 15, 16 and 17. In some embodiments, the substitutions, insertions or deletions occur in regions outside the HVRs (i.e., in the FRs). In some embodiments, a modified anti-Factor D antibody comprises a light chain variable domain comprising an amino acid sequence selected from the group consisting of SEQ ID NO: 6, 7, 8, 9, 10, 11, 12, 13, 14, 15, 16 and 17. In one example, the invention provides a fragment of said anti-Factor D antibodies (e.g. antigen-binding fragments).

For example, the invention provides a modified anti-Factor D antibody comprising a heavy chain variable domain comprising SEQ ID NO: 18. For example, the invention provides a modified anti-Factor D antibody comprising a light chain variable domain comprising SEQ ID NO: 6. For example, the invention provides a modified anti-Factor D antibody comprising a heavy chain variable domain comprising SEQ ID NO: 18 and a light chain variable domain comprising SEQ ID NO: 6. For example, the invention provides a modified anti-Factor D antibody comprising a heavy chain variable domain comprising SEQ ID NO: 19. For example, the invention provides a modified anti-Factor D antibody comprising a light chain variable domain comprising SEQ ID NO: 7. For example, the invention provides a modified anti-Factor D antibody comprising a heavy chain variable domain comprising SEQ ID NO: 19 and a light chain variable domain comprising SEQ ID NO: 7. For example, the invention provides a modified anti-Factor D antibody comprising a heavy chain variable domain comprising SEQ ID NO: 20. For example, the invention provides a modified anti-Factor D antibody comprising a light chain variable domain comprising SEQ ID NO: 8. For example, the invention provides a modified anti-Factor D antibody comprising a heavy chain variable domain comprising SEQ ID NO: 20 and a light chain variable domain comprising SEQ ID NO: 8. For example, the invention provides a modified anti-Factor D antibody comprising a heavy chain variable domain comprising SEQ ID NO: 21. For example, the invention provides a modified anti-Factor D antibody comprising a light chain variable domain comprising SEQ ID NO: 9. For example, the invention provides a modified anti-Factor D antibody comprising a heavy chain variable domain comprising SEQ ID NO: 21 and a light chain variable domain comprising SEQ ID NO: 9. For example, the invention provides a modified anti-Factor D antibody comprising a heavy chain variable domain comprising SEQ ID NO: 22. For example, the invention provides a modified anti-Factor D antibody comprising a light chain variable domain comprising SEQ ID NO: 10. For example, the invention provides a modified anti-Factor D antibody comprising a heavy chain variable domain comprising SEQ ID NO: 22 and a light chain variable domain comprising SEQ ID NO: 10. For example, the invention provides a modified anti-Factor D antibody comprising a heavy chain variable domain comprising SEQ ID NO: 23. For example, the invention provides a modified anti-Factor D antibody comprising a light chain variable domain comprising SEQ ID NO: 11. For example, the invention provides a modified anti-Factor D antibody comprising a heavy chain variable domain comprising SEQ ID NO: 23 and a light chain variable domain comprising SEQ ID NO: 11. For example, the invention provides a modified anti-Factor D antibody comprising a heavy chain variable domain comprising SEQ ID NO: 24. For example, the invention provides a modified anti-Factor D antibody comprising a light chain variable domain comprising SEQ ID NO: 12. For example, the invention provides a modified anti-Factor D antibody comprising a heavy chain variable domain comprising SEQ ID NO: 24 and a light chain variable domain comprising SEQ ID NO: 12. For example, the invention provides a modified anti-Factor D antibody comprising a heavy chain variable domain comprising SEQ ID NO: 25. For example, the invention provides a modified anti-Factor D antibody comprising a light chain variable domain comprising SEQ ID NO: 13. For example, the invention provides a modified anti-Factor D antibody comprising a heavy chain variable domain comprising SEQ ID NO: 25 and a light chain variable domain comprising SEQ ID NO: 13. For example, the invention provides a modified anti-Factor D antibody comprising a heavy chain variable domain comprising SEQ ID NO: 26. For example, the invention provides a modified anti-Factor D antibody comprising a light chain variable domain comprising SEQ ID NO: 14. For example, the invention provides a modified anti-Factor D antibody comprising a heavy chain variable domain comprising SEQ ID NO: 26 and a light chain variable domain comprising SEQ ID NO: 14. For example, the invention provides a modified anti-Factor D antibody comprising a heavy chain variable domain comprising SEQ ID NO: 27. For example, the invention provides a modified anti-Factor D antibody comprising a light chain variable domain comprising SEQ ID NO: 15. For example, the invention provides a modified anti-Factor D antibody comprising a heavy chain variable domain comprising SEQ ID NO: 27 and a light chain variable domain comprising SEQ ID NO: 15. For example, the invention provides a modified anti-Factor D antibody comprising a heavy chain variable domain comprising SEQ ID NO: 28. For example, the invention provides a modified anti-Factor D antibody comprising a light chain variable domain comprising SEQ ID NO: 16. For example, the invention provides a modified anti-Factor D antibody comprising a heavy chain variable domain comprising SEQ ID NO: 28 and a light chain variable domain comprising SEQ ID NO: 16. For example, the invention provides a modified anti-Factor D antibody comprising a heavy chain variable domain comprising SEQ ID NO: 29. For example, the invention provides a modified anti-Factor D antibody comprising a light chain variable domain comprising SEQ ID NO: 17. For example, the invention provides a modified anti-Factor D antibody comprising a heavy chain variable domain comprising SEQ ID NO: 29 and a light chain variable domain comprising SEQ ID NO: 17. In one example, the invention provides a fragment of said anti-Factor D antibodies (e.g. antigen-binding fragments).

In one embodiment, the invention provides a polypeptide comprising the following amino acid sequence: $X_1$VQLVQSGPELKKPGASVKVSCKASGYTFTNYGMN WVRQAPGQGLEWMGWINTYTGETTYADDFKGRFV FSLDTSVSTAYLQISSLKAEDTAVYYCEREGGV$X_2$$X_3$ WGQGTLVTVSS (SEQ ID NO: 74), wherein $X_1$ is Q or E; $X_2$ is N, A or Q; and $X_3$ is N, A or Q. In one embodiment, the invention provides a modified anti-Factor D antibody comprising the following amino acid sequence: X$_1$VQLVQSGPELKKPGASVKVSCKASGYTFTNYGMN WVRQAPGQGLEWMGWINTYTGETTYADDFKGRFV F SLDTSVSTAYLQISSLKAEDTAVYYCEREGGVX$_2$X$_3$ WGQGTLVTVSS (SEQ ID NO: 74), wherein X$_1$ is Q or E; X$_2$ is N, A or Q; and X$_3$ is N, A or Q. In one example, the invention provides a fragment of said polypeptide.

In one embodiment, the invention provides a polypeptide comprising following amino acid sequence: DIQVTQ SPSSLSASVGDRVTITCITSTDIDDDX$_4$X$_5$WYQQKPGK VPKLLISGGX$_6$TLRPGVPSRFSGSGSGTDFTLTISSLQP EDVATYYCLQSDSLPYTFGQGTKX$_7$EIK (SEQ ID NO: 73), wherein X$_4$ is M, L or I; X$_5$ is N, A or Q; X$_6$ is N, S or A; and X$_7$ is L or V. In one embodiment, the invention provides a modified anti-Factor D antibody comprising the polypeptide comprising the following amino acid sequence: DIQVTQSPSSLSASVGDRVTITCITSTDIDDDX$_4$X$_5$WY QQKPGKVPKLLISGGX$_6$TLRPGVPSRFSGSGSGTDFT LTISSLQPEDVATYYCLQSDSLPYTFGQGTKX$_7$EIK (SEQ ID NO: 73), wherein X$_4$ is M, L or I; X$_5$ is N, A or Q; X$_6$ is N, S or A; and X$_7$ is L or V. In one example, the invention provides a fragment of said polypeptide.

In one embodiment, the invention provides a polypeptide comprising an amino acid sequence selected from the group comprising SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28 and SEQ ID NO: 29. In another embodiment, the invention provides a polypeptide comprising an amino acid sequence selected from the group comprising SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16 and SEQ ID NO: 17. In one example, the invention provides a fragment of said polypeptide.

In one aspect, the invention provides a modified anti-Factor D antibody, wherein the light chain domain comprises the sequence of SEQ ID NO: 47. In another aspect, the invention provides a modified anti-Factor D antibody, wherein the heavy chain domain comprises the sequence of SEQ ID NO: 54. In one aspect, the invention provides a modified anti-Factor D antibody, wherein the light chain domain comprises the sequence of SEQ ID NO: 61. In another aspect, the invention provides a modified anti-Factor D antibody, wherein the heavy chain domain comprises the sequence of SEQ ID NO:63. In one example, the invention provides a fragment of said anti-Factor D antibodies (e.g. antigen-binding fragments).

In one aspect, the invention provides a polypeptide comprising the sequence of SEQ ID NO: 47. In another aspect, the invention provides a polypeptide comprising the sequence of SEQ ID NO: 54. In one aspect, the invention provides a polypeptide comprising the sequence of SEQ ID NO: 61. In another aspect, the invention provides a polypeptide comprising the sequence of SEQ ID NO: 63. In one example, the invention provides a fragment of said polypeptide.

In one aspect, the invention provides a modified anti-Factor D antibody of humanized anti-Factor D #111, wherein the variable light chain domain comprises the amino acid sequence selected from the group consisting of SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16 and SEQ ID NO: 17. In one example, the invention provides a fragment of said anti-Factor D antibody (e.g. antigen-binding fragment).

In one aspect, the invention provides a modified anti-Factor D antibody of humanized anti-Factor D #111, wherein the variable heavy chain domain comprises the sequence selected from the group consisting of SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28 and SEQ ID NO: 29. In one example, the invention provides a fragment of said anti-Factor D antibodies (e.g. antigen-binding fragments).

In one aspect, the invention provides a modified anti-Factor D antibody of humanized anti-Factor D #111, wherein the light chain domain comprises the sequence of SEQ ID NO: 47. In another aspect, the invention provides a modified anti-Factor D antibody of humanized anti-Factor D #111, wherein the heavy chain domain comprises the sequence of SEQ ID NO: 54. In one aspect, the invention provides a modified anti-Factor D antibody of humanized anti-Factor D #111, wherein the light chain domain comprises the sequence of SEQ ID NO: 61. In another aspect, the invention provides a modified anti-Factor D antibody of humanized anti-Factor D #111, wherein the heavy chain domain comprises the sequence of SEQ ID NO: 63. In one example, the invention provides a fragment of said anti-Factor D antibody (e.g. antigen-binding fragment).

In one aspect, the invention provides a modified anti-Factor D antibody of humanized anti-Factor D #111, wherein the variable light chain domain comprises the sequence of SEQ ID NO: 6 and the variable heavy chain domain comprises the sequence of SEQ ID NO: 18. In one embodiment, the invention provides a modified anti-Factor D antibody of humanized anti-Factor D #111, wherein the variable light chain domain comprises the sequence of SEQ ID NO: 7 and the variable heavy chain domain comprises the sequence of SEQ ID NO: 19. In another embodiment, the invention provides a modified anti-Factor D antibody of humanized anti-Factor D #111, wherein the variable light chain domain comprises the sequence of SEQ ID NO: 8 and the variable heavy chain domain comprises the sequence of SEQ ID NO: 20. In another embodiment, the invention provides a modified anti-Factor D antibody of humanized anti-Factor D #111, wherein the variable light chain domain comprises the sequence of SEQ ID NO: 9 and the variable heavy chain domain comprises the sequence of SEQ ID NO: 21. In another embodiment, the invention provides a modified anti-Factor D antibody of humanized anti-Factor D #111, wherein the variable light chain domain comprises the sequence of SEQ ID NO: 10 and variable heavy chain domain comprises the sequence of SEQ ID NO: 22. In another embodiment, the invention provides a modified anti-Factor D antibody of humanized anti-Factor D #111, wherein the variable light chain domain comprises the sequence of SEQ ID NO: 11 and the variable heavy chain domain comprises the sequence of SEQ ID NO: 23. In another embodiment, the invention provides a modified anti-Factor D antibody of humanized anti-Factor D #111, wherein the variable light chain domain comprises the sequence of SEQ ID NO: 12 and the variable heavy chain domain comprises the sequence of SEQ ID NO: 24. In another embodiment, the invention provides a modified anti-Factor D antibody of humanized anti-Factor D #111, wherein the variable light chain domain comprises the sequence of SEQ ID NO: 13 and the variable heavy chain domain comprises the sequence of SEQ ID NO: 25. In another embodiment, the invention provides a modified anti-Factor D antibody of humanized anti-Factor D #111, wherein the variable light chain domain comprises the sequence of SEQ ID NO: 14 and the variable heavy chain domain comprises the sequence of SEQ ID NO: 26. In another embodiment, the invention provides a modified anti-Factor D antibody of humanized anti-Factor D #111, wherein the variable light chain domain comprises the sequence of SEQ ID NO: 15 and the variable heavy chain domain comprises the sequence of SEQ ID NO: 27. In another embodiment, the invention provides a modified anti-Factor D antibody of humanized anti-Factor D #111, wherein the variable light chain domain comprises the sequence of SEQ ID NO: 16 and the variable heavy chain domain comprises the sequence of SEQ ID NO: 28. In another embodiment, the invention provides a modified anti-Factor D antibody of humanized anti-Factor D #111, wherein the variable light chain domain comprises the sequence of SEQ ID NO: 17 and the variable heavy chain domain comprises the sequence of SEQ ID NO: 29. In one example, the invention provides a fragment of said anti-Factor D antibodies (e.g. antigen-binding fragments).

In one aspect, the invention provides a modified anti-Factor D antibody of humanized anti-Factor D #111, wherein the light chain domain comprises the sequence of SEQ ID NO: 47 and the heavy chain domain comprises the sequence of SEQ ID NO: 54. In one aspect, the invention provides a modified anti-Factor D antibody of humanized anti-Factor D #111, wherein the light chain domain comprises the sequence of SEQ ID NO: 61 and the heavy chain domain comprises the sequence of SEQ ID NO: 63.

3. Affinity and Biological Activity of Anti-Factor D Antibodies

The invention herein includes antibodies, and variants thereof or fragments thereof (e.g. antigen-binding fragments), having characteristics identified herein as being desireable in an anti-Factor D antibody. Antibodies, and variants thereof or fragments thereof (e.g. antigen-binding fragments), having characteristics identified herein as being desireable in an anti-Factor D antibody, may be screened for inhibitory biological activity, for example in vitro or in vivo, or by measuring binding affinity.

a. Affinity

To determine whether an anti-Factor D antibody, and variants thereof or fragments thereof (e.g. antigen-binding fragments), bind to the same epitope on human Factor D bound by an antibody of interest (for example, those antibodies which antagonize Factor D activity), a cross-blocking assay may be performed (Antibodies, A Laboratory Manual, Cold Spring Harbor Laboratory, Ed Harlow and David Lane (1988)). Alternatively, epitope mapping may be performed to determine whether an anti-Factor D antibody binds an epitope of interest (Champe et al., *J. Biol. Chem.*, 270: 1388-1394 (1995). Antibody affinities, for example for human Factor D, may be determined using standard methods, including those described in Example 3.

In one aspect, the invention provides anti-Factor D antibodies, or antibody variants thereof, or fragments thereof (e.g. antigen-binding fragments), that compete with a murine anti-Factor D antibody and/or humanized anti-Factor D antibody clone #111, and/or an antibody comprising variable domain or HVR sequences of humanized anti-Factor D antibody clone #111. Anti-Factor D antibodies, or variants thereof, or fragments thereof (e.g. antigen-binding fragments) that bind to the same epitope as a murine anti-Factor D antibody and/or humanized anti-Factor D antibody clone #111, and/or an antibody comprising variable domain or HVR sequences of humanized anti-Factor D antibody clone #111, are also provided.

In one embodiment, the invention provides an anti-Factor D antibody, or antibody variant thereof, wherein the monovalent affinity of the antibody to Factor D (e.g., affinity of the antibody as a Fab fragment to Factor D) is lower, for example at least 1-fold or 2-fold lower than the monovalent affinity of a chimeric antibody (e.g. affinity of the chimeric antibody as a Fab fragment to Factor D), comprising, consisting or consisting essentially of a light chain variable domain of and heavy chain variable domain from a murine anti-Factor D antibody. In one example, the invention provides a fragment of said anti-Factor D antibodies (e.g. antigen-binding fragments).

In one embodiment, the invention provides an anti-Factor D antibody, or antibody variant thereof, wherein the bivalent affinity of the antibody to Factor D (e.g., affinity of the antibody as an IgG to Factor D) is lower, for example at least 1-fold or 2-fold lower than the bivalent affinity of a chimeric antibody (e.g. affinity of the chimeric antibody as an IgG to Factor D), comprising, consisting or consisting essentially of a light chain variable domain and heavy chain variable domain from a murine anti-Factor D antibody. In one example, the invention provides a fragment of said anti-Factor D antibodies (e.g. antigen-binding fragments).

In another embodiment, the invention provides an anti-Factor D antibody, or antibody variant thereof, wherein the monovalent affinity of the antibody to Factor D (e.g., affinity of the antibody as a Fab fragment to Factor D) is greater, for example at least 1-fold or 2-fold greater than the monovalent affinity of a chimeric antibody (e.g. affinity of the chimeric antibody as a Fab fragment to Factor D), comprising, consisting or consisting essentially of a light chain variable domain and heavy chain variable domain from a murine anti-Factor D antibody. In one example, the invention provides a fragment of said anti-Factor D antibodies (e.g. antigen-binding fragments).

In another embodiment, the invention provides an anti-Factor D antibody, or antibody variants thereof, wherein the bivalent affinity of the antibody to Factor D (e.g., affinity of the antibody as an IgG to Factor D) is greater, for example at least 1-fold or 2-fold greater than the bivalent affinity of a chimeric antibody (e.g. affinity of the chimeric antibody as an IgG to Factor D), comprising, consisting or consisting essentially of a light chain variable domain and heavy chain variable domain from a murine anti-Factor D antibody. In one example, the invention provides a fragment of said anti-Factor D antibodies (e.g. antigen-binding fragments).

In another embodiment, the invention provides an anti-Factor D antibody, or antibody variant thereof, wherein the affinity of the antibody in its monovalent form to Factor D (e.g., affinity of the antibody as a Fab fragment to Factor D) is 20 nM ($20 \times 10^{-9}$ M) or better. In another embodiment, the invention provides an anti-Factor D antibody, or antibody variant thereof, wherein the affinity of the antibody in its monovalent form to Factor D (e.g., affinity of the antibody as a Fab fragment to Factor D) is 10 nM ($10 \times 10^{-9}$ M) or better. In another embodiment, the invention provides an anti-Factor D antibody, or antibody variant thereof, wherein the affinity of the antibody in its monovalent form to Factor D (e.g., affinity of the antibody as a Fab fragment to Factor D) is 1.0 nM ($1.0 \times 10^{-9}$ M) or better. In another embodiment, the invention provides an anti-Factor D antibody, or antibody variant thereof, wherein the affinity of the antibody in its monovalent form to Factor D (e.g., affinity of the antibody as a Fab fragment to Factor D) is 0.5 nM ($0.5 \times 10^{-9}$ M) or better. In another embodiment, the invention provides an anti-Factor D antibody, or antibody variant thereof, wherein the affinity of the antibody in its monovalent form to Factor D (e.g., affinity of the antibody as a Fab fragment to Factor D) is 1.0 µM ($1.0 \times 10^{-12}$ M) or better. In another embodiment, the invention provides an anti-Factor D antibody, or antibody variant thereof, wherein the affinity of the antibody in its monovalent form to Factor D (e.g., affinity of the antibody as a Fab fragment to Factor D) is 0.5 µM ($0.5 \times 10^{-12}$ M) or better. In one example, the invention provides a fragment of said anti-Factor D antibodies (e.g. antigen-binding fragments).

In another embodiment, the invention provides an anti-Factor D antibody, or antibody variant thereof, wherein the affinity of the antibody in its bivalent form to Factor D (e.g., affinity of the antibody as an IgG to Factor D) is 10.0 nM ($10.0 \times 10^{-9}$ M) or better. In another embodiment, the invention provides an anti-Factor D antibody, or antibody variant thereof, wherein the affinity of the antibody in its bivalent form to Factor D (e.g., affinity of the antibody as an IgG to Factor D) is 5.0 nM ($5.0 \times 10^{-9}$ M) or better. In another embodiment, the invention provides an anti-Factor D antibody, or antibody variant thereof, wherein the affinity of the antibody in its bivalent form to Factor D (e.g., affinity of the antibody as an IgG to Factor D) is 1.0 nM ($1.0 \times 10^{-9}$ M) or better. In another embodiment, the invention provides an anti-Factor D antibody, or antibody variant thereof, wherein the affinity of the antibody in its bivalent form to Factor D (e.g., affinity of the antibody as an IgG to Factor D) is 0.5 nM ($0.5 \times 10^{-9}$ M) or better. In another embodiment, the invention provides an anti-Factor D antibody, or antibody variant thereof, wherein the affinity of the antibody in its bivalent form to Factor D (e.g., affinity of the antibody as an IgG to Factor D) is 5.0 µM ($5.0 \times 10^{-12}$ M) or better. In another embodiment, the invention provides an anti-Factor D antibody, or antibody variant thereof, wherein the affinity of the antibody in its bivalent form to Factor D (e.g., affinity of the antibody as an IgG to Factor D) is 2.0 µM ($2.0 \times 10^{-12}$ M) or better. In another embodiment, the invention provides an anti-Factor D antibody, or antibody variant thereof, wherein the affinity of the antibody in its bivalent form to Factor D (e.g., affinity of the antibody as an IgG to Factor D) is 1.0 µM ($1.0 \times 10^{-12}$ M) or better. In another embodiment, the invention provides an anti-Factor D antibody, or antibody variant thereof, wherein the affinity of the antibody in its bivalent form to Factor D (e.g., affinity of the antibody as an IgG to Factor D) is 0.5 µM ($0.5 \times 10^{-12}$ M) or better. In one example, the invention provides a fragment of said anti-Factor D antibodies (e.g. antigen-binding fragments).

In another embodiment, the invention provides an anti-Factor D antibody, or antibody variant thereof, wherein the affinity of the antibody in its monovalent form to Factor D (e.g., affinity of the antibody as a Fab fragment to Factor D) is between 0.5 mM ($0.5 \times 10^{-6}$ M) and 0.5 µM ($0.5 \times 10^{-12}$ M). In another embodiment, the invention provides an anti-Factor D antibody, or antibody variant thereof, wherein the affinity of the antibody in its monovalent form to Factor D (e.g., affinity of the antibody as a Fab fragment to Factor D) is between 15 nM ($15 \times 10^{-9}$ M) and 0.1 nM ($0.1 \times 10^{-9}$ M). In another embodiment, the invention provides an anti-Factor D antibody, or antibody variant thereof, wherein the affinity of the antibody in its monovalent form to Factor D (e.g., affinity of the antibody as a Fab fragment to Factor D) is between 5.5 nM ($5.5 \times 10^{-9}$ M) and 1 nM ($1 \times 10^{-9}$ M). In another embodiment, the invention provides an anti-Factor D antibody, or antibody variant thereof, wherein the affinity of the antibody in its monovalent form to Factor D (e.g., affinity of the antibody as a Fab fragment to Factor D) is between 0.5 µM ($0.5 \times 10^{-12}$ M) and 2 µM ($2 \times 10^{-12}$ M). In one example, the invention provides a fragment of said anti-Factor D antibodies (e.g. antigen-binding fragments).

In another embodiment, the invention provides an anti-Factor D antibody, or antibody variant thereof, wherein the affinity of the antibody in its bivalent form to Factor D (e.g., affinity of the antibody as an IgG to Factor D) is between 0.5 mM ($0.5 \times 10^{-6}$ M) and 0.5 pM ($0.5 \times 10^{-12}$ M). In another embodiment, the invention provides an anti-Factor D antibody, or antibody variants thereof, wherein the affinity of the antibody in its bivalent form to Factor D (e.g., affinity of the antibody as an IgG to Factor D) is between 10 nM ($10 \times 10^{-9}$ M) and 0.05 nM ($0.05 \times 10^{-9}$ M). In another embodiment, the invention provides an anti-Factor D antibody, or antibody variant thereof, wherein the affinity of the antibody in its bivalent form to Factor D (e.g., affinity of the antibody as an IgG to Factor D) is between 5.5 nM ($5.5 \times 10^{-9}$ M) and 1 nM ($1 \times 10^{-9}$ M). In another embodiment, the invention provides an anti-Factor D antibody, or antibody variant thereof, wherein the affinity of the antibody in its bivalent form to Factor D (e.g., affinity of the antibody as an IgG to Factor D) is between 0.5 µM ($0.5 \times 10^{-12}$ M) and 2 µM ($2 \times 10^{-12}$ M). In one example, the invention provides a fragment of said anti-Factor D antibodies (e.g. antigen-binding fragments).

In another embodiment, the invention provides an anti-Factor D antibody, or antibody variant thereof, wherein the affinity of the antibody in its monovalent form to Factor D (e.g., affinity of the antibody as a Fab fragment to Factor D) is about 1.4 µM ($1.4 \times 10^{-12}$ M). In another embodiment, the invention provides an anti-Factor D antibody, or antibody variant thereof, wherein the affinity of the antibody in its bivalent form to Factor D (e.g., affinity of the antibody as a IgG to Factor D) is about 1.1 µM ($1.1 \times 10^{-12}$ M). In another embodiment, the invention provides an anti-Factor D antibody, or antibody variant thereof, wherein the affinity of the antibody in its monovalent form to Factor D (e.g., affinity of the antibody as a Fab fragment to Factor D) is about 0.19 nM ($0.19 \times 10^{-9}$ M). In another embodiment, the invention provides an anti-Factor D antibody, or antibody variant thereof, wherein the affinity of the antibody in its bivalent form to Factor D (e.g., affinity of the antibody as a IgG to Factor D) is about 0.08 nM ($0.08 \times 10^{-9}$ M). In another embodiment, the invention provides an anti-Factor D antibody, or antibody variant thereof, wherein the affinity of the antibody in its monovalent form to Factor D (e.g., affinity of the antibody as a Fab fragment to Factor D) is about 12.3 nM ($12.3 \times 10^{-9}$ M). In another embodiment, the invention provides an anti-Factor D antibody, or antibody variant thereof, wherein the affinity of the antibody in its bivalent form to Factor D (e.g., affinity of the antibody as a IgG to Factor D) is about 9.0 nM ($9.0 \times 10^{-9}$ M). In one example, the invention provides a fragment of said anti-Factor D antibodies (e.g. antigen-binding fragments).

In another embodiment, the invention provides an anti-Factor D antibody, or antibody variant thereof, wherein the affinity of the antibody in its monovalent form to Factor D (e.g., affinity of the antibody as a Fab fragment to Factor D) is about 1.4 µM ($1.4 \times 10^{-12}$ M)±0.5. In another embodiment, the invention provides an anti-Factor D antibody, or antibody variant thereof, wherein the affinity of the antibody in its bivalent form to Factor D (e.g., affinity of the antibody as an IgG to Factor D) is about 1.1 µM ($1.1 \times 10^{-12}$ M)±0.6. In another embodiment, the invention provides an anti-Factor D antibody, or antibody variant thereof, wherein the affinity of the antibody in its monovalent form to Factor D (e.g., affinity of the antibody as a Fab fragment to Factor D) is about 0.19 nM ($0.19 \times 10^{-9}$ M)±0.01. In another embodiment, the invention provides an anti-Factor D antibody, or antibody variant thereof, wherein the affinity of the antibody in its bivalent form to Factor D (e.g., affinity of the antibody as a IgG to Factor D) is about 0.08 nM ($0.08 \times 10^{-9}$ M)±0.01. In another embodiment, the invention provides an anti-Factor D antibody, or antibody variant thereof, wherein the affinity of the antibody in its monovalent form to Factor D (e.g., affinity of the antibody as a Fab fragment to Factor D) is about 12.3 nM ($12.3 \times 10^{-9}$ M)±2. In another embodiment, the invention provides an anti-Factor D antibody, or antibody variant thereof, wherein the affinity of the antibody in its bivalent form to Factor D (e.g., affinity of the antibody as a IgG to Factor D) is about 9.0 nM (9.0×10$^{-9}$ M)±1. In one example, the invention provides a fragment of said anti-Factor D antibodies (e.g. antigen-binding fragments).

In another embodiment, an anti-Factor D antibody, or antibody variant thereof, may have an affinity in its monovalent form to Factor D (e.g., affinity of the antibody as a Fab fragment to Factor D) of about 1.4 pM (1.4×10$^{-12}$ M)±2. In another embodiment, an anti-Factor D antibody, or antibody variant thereof, may have an affinity in its bivalent form to Factor D (e.g., affinity of the antibody as a IgG to Factor D) of about 1.1 μM (1.1×10$^{-12}$ M)±2. In another embodiment, an anti-Factor D antibody, or antibody variant thereof, may have an affinity in its monovalent form to Factor D (e.g., affinity of the antibody as a Fab fragment to Factor D) is about 0.19 nM (0.19×10$^{-9}$ M)±2. In another embodiment, an anti-Factor D antibody, or antibody variant thereof, may have an affinity in its bivalent form to Factor D (e.g., affinity of the antibody as a IgG to Factor D) is about 0.08 nM (0.08×10$^{-9}$ M)±2. In another embodiment, an anti-Factor D antibody, or antibody variant thereof, may have an affinity in its monovalent form to Factor D (e.g., affinity of the antibody as a Fab fragment to Factor D) is about 12.3 nM (12.3×10$^{-9}$ M)±2. In another embodiment, an anti-Factor D antibody, or antibody variant thereof, may have an affinity in its bivalent form to Factor D (e.g., affinity of the antibody as a IgG to Factor D) is about 9.0 nM (9.0×10$^{-9}$ M)±2. In one example, the invention provides a fragment of said anti-Factor D antibodies (e.g. antigen-binding fragments).

As is well-established in the art, binding affinity of a ligand to its receptor can be determined using any of a variety of assays, and expressed in terms of a variety of quantitative values. Accordingly, in one embodiment, the binding affinity is expressed as $K_D$ values and reflects intrinsic binding affinity (e.g., with minimized avidity effects). Generally and preferably, binding affinity is measured in vitro, whether in a cell-free or cell-associated setting. As described in greater detail herein, fold difference in binding affinity can be quantified in terms of the ratio of the monovalent binding affinity value of a humanized antibody (e.g., in Fab form) and the monovalent binding affinity value of a reference/comparator antibody (e.g., in Fab form) (e.g., a murine antibody having donor hypervariable region sequences), wherein the binding affinity values are determined under similar assay conditions. Thus, in one embodiment, the fold difference in binding affinity is determined as the ratio of the $K_D$ values of the humanized antibody in Fab form and said reference/comparator Fab antibody. For example, in one embodiment, if an antibody of the invention (A) has an affinity that is "3-fold lower" than the affinity of a reference antibody (M), then if the $K_D$ value for A is 3×, the $K_D$ value of M would be 1×, and the ratio of $K_D$ of A to $K_D$ of M would be 3:1. Conversely, in one embodiment, if an antibody of the invention (C) has an affinity that is "3-fold greater" than the affinity of a reference antibody (R), then if the $K_D$ value for C is 1×, the $K_D$ value of R would be 3×, and the ratio of $K_D$ of C to $K_D$ of R would be 1:3. Any of a number of assays known in the art, including those described herein, can be used to obtain binding affinity measurements, including, for example, Biacore, radioimmunoassay (RIA) and ELISA.

Further, $K_D$ values for an antibody of the invention may vary depending on conditions of the particular assay used. For example, in one embodiment, binding affinity measurements may be obtained in an assay wherein the Fab or antibody is immobilized and binding of the ligand, i.e. Factor D, is measured or alternatively, the ligand, i.e. Factor D, for the Fab or antibody is immobilized and binding of the Fab or antibody is measured. In one embodiment, the binding affinity measurements may be obtained in an assay wherein the regeneration conditions may comprise (1) 10 mM glycine or 4M MgCl$_2$ at pH 1.5, and (2) pH between pH of 1.0 and pH of 7.5, including pH of 1.5, pH of 5.0, pH of 6.0 and pH of 7.2. In one embodiment, the binding affinity measurements may be obtained in an assay wherein the binding conditions may comprise (1) PBS or HEPES-buffered saline and (2) Tween-20, i.e. 0.1% Tween-20. In one embodiment, the binding affinity measurements may be obtained in an assay wherein the source of the ligand, i.e. Factor D, may be from commercially available sources. In one embodiment, binding affinity measurements may be obtained in an assay wherein (1) the Fab or antibody is immobilized and binding of the ligand, i.e. Factor D is measured, (2) the regeneration conditions comprise 4M MgCl$_2$ at pH 7.2 and (3) the binding conditions comprise HEPES-buffered saline, pH 7.2 containing 0.1% Tween-20. In one embodiment, binding affinity measurements may be obtained in an assay wherein (1) the ligand, i.e. Factor D, is immobilized and binding of the Fab or antibody is measured, (2) the regeneration conditions comprise 10 mM glycine at pH 1.5 and (3) the binding conditions comprise PBS buffer.

b. Biological Activity

To determine whether an anti-Factor D antibody, or variant or fragment thereof (e.g. antigen-binding fragment) is capable of binding to Factor D and exerting a biological effect, for example, inhibition of alternative pathway hemolysis, hemolytic inhibition assays using rabbit RBCs may be used, including those described in Example 2. Such hemolytic inhibition may be determined using standard assays (Kostavasili et al., *J of Immunology*, 158(4): 1763-72 (1997); Wiesmann et al., *Nature*, 444(7116): 159-60 (2006)). Activation of complement in such assays may be initiated with serum or plasma. Appropriate concentrations of Factor D in serum or plasma (Pascual et al., *Kidney International*, 34: 529-536 (1998); Complement Facts Book, Bernard J. Morley and Mark J. Walport, editors, Academic Press (2000); Barnum et al., *J. Immunol. Methods*, 67: 303-309 (1984)) can be routinely determined according to methods known in the art, including those that have been described in references such as Pascual et al., *Kidney International*, 34: 529-536 (1998) and Barnum et al., *J. Immunol. Methods*, 67: 303-309 (1984) and Example 4. The present invention relates generally to antibodies capable of inhibiting biological activities associated with Factor D. For example, at a concentration of 18 μg/ml (equivalent to about 1.5 times the molar concentration of human factor D in the blood; molar ratio of anti-Factor D antibody to Factor D of about 1.5:1), significant inhibition of the alternative complement activity by the antibody can be observed (see, e.g., U.S. Pat. No. 6,956,107)

In one embodiment, the invention includes anti-Factor D antibodies, wherein a Fab fragment of such antibodies inhibits alternative pathway hemolysis with IC$_{50}$ values less than 30 nM. In one embodiment, the invention includes anti-Factor D antibodies, wherein a Fab fragment of such antibodies inhibits alternative pathway hemolysis with IC$_{50}$ values less than 15 nM. In one embodiment, the invention provides anti-Factor D antibodies, wherein a Fab fragment of such antibodies inhibits, inhibits alternative pathway hemolysis with IC$_{50}$ values less than 10 nM. In one embodiment, the invention provides anti-Factor D antibodies, wherein a Fab fragment of such antibodies inhibits alternative pathway hemolysis with IC$_{50}$ values less than 5 nM. In one example, the invention provides a fragment of said anti-Factor D antibodies (e.g. antigen-binding fragments).

In one embodiment, the invention provides anti-Factor D antibodies, wherein a Fab fragment of such antibodies inhibits alternative pathway hemolysis with $IC_{50}$ values between 30 nM and 2 nM. In one embodiment, the invention provides anti-Factor D antibodies, wherein a Fab fragment of such antibodies inhibits alternative pathway hemolysis with $IC_{50}$ values between 25 nM and 7 nM. In one embodiment, the invention provides anti-Factor D antibodies, wherein a Fab fragment of such antibodies inhibits alternative pathway hemolysis with $IC_{50}$ values between 20 nM and 12 nM. In one embodiment, the invention provides anti-Factor D antibodies, wherein a Fab fragment of such antibodies inhibits alternative pathway hemolysis with $IC_{50}$ values between 30 nM and 15 nM. In one embodiment, the invention provides anti-Factor D antibodies, wherein a Fab fragment of such antibodies inhibits alternative pathway hemolysis with $IC_{50}$ values between 12 nM and 8 nM. In one embodiment, the invention provides anti-Factor D antibodies, wherein a Fab fragment of such antibodies inhibits alternative pathway hemolysis with $IC_{50}$ values between 7 nM and 2 nM. In one embodiment, the invention provides anti-Factor D antibodies, wherein a Fab fragment of such antibodies inhibits alternative pathway hemolysis with $IC_{50}$ values between 6 nM and 3 nM. In one embodiment, the invention provides anti-Factor D antibodies, wherein a Fab fragment of such antibodies inhibits alternative pathway hemolysis with $IC_{50}$ values between 8 nM and 5 nM. In one embodiment, the invention provides anti-Factor D antibodies, wherein a Fab fragment of such antibodies inhibits alternative pathway hemolysis with $IC_{50}$ values between 5 nM and 2 nM. In one embodiment, the invention provides anti-Factor D antibodies, wherein a Fab fragment of such antibodies inhibits alternative pathway hemolysis with $IC_{50}$ values between 10 nM and 5 nM. In one embodiment, the invention provides anti-Factor D antibodies, wherein a Fab fragment of such antibodies inhibits alternative pathway hemolysis with $IC_{50}$ values between 8 nM and 2 nM. In one embodiment, the invention provides anti-Factor D antibodies, wherein a Fab fragment of such antibodies inhibits alternative pathway hemolysis with $IC_{50}$ values between 7 nM and 3 nM. In one embodiment, the invention provides anti-Factor D antibodies, wherein a Fab fragment of such antibodies inhibits alternative pathway hemolysis with $IC_{50}$ values between 6 nM and 4 nM. In another embodiment, the invention provides anti-Factor D antibodies, wherein a Fab fragment of such antibodies inhibits alternative pathway hemolysis with an $IC_{50}$ value of about 4.7 nM±0.6 nM. In another embodiment, the invention provides anti-Factor D antibodies, wherein a Fab fragment of such antibodies inhibits alternative pathway hemolysis with an $IC_{50}$ value of about 6.4 nM±0.6 nM. In another embodiment, the invention provides anti-Factor D antibodies, wherein a Fab fragment of such antibodies inhibits alternative pathway hemolysis with an $IC_{50}$ value of about 3.5 nM±0.5 nM. In another embodiment, the invention provides anti-Factor D antibodies, wherein a Fab fragment of such antibodies inhibits alternative pathway hemolysis with an $IC_{50}$ value of about 4.4 nM±1.5 nM. In another embodiment, the invention provides anti-Factor D antibodies, wherein a Fab fragment of such antibodies inhibits alternative pathway hemolysis with an $IC_{50}$ value of about 10.2 nM±0.8 nM. In another embodiment, the invention provides anti-Factor D antibodies, wherein a Fab fragment of such antibodies inhibits alternative pathway hemolysis with an $IC_{50}$ value of about 23.9 nM±5.0 nM. In one example, the invention provides a fragment of said anti-Factor D antibodies (e.g. antigen-binding fragments).

In one embodiment, the invention provides anti-Factor D antibodies, wherein a Fab fragment of such antibodies inhibits alternative pathway hemolysis with $IC_{90}$ values less than 80 nM. In one embodiment, the invention provides anti-Factor D antibodies, wherein a Fab fragment of such antibodies inhibits alternative pathway hemolysis with $IC_{90}$ values less than 50 nM. In one embodiment, the invention provides anti-Factor D antibodies, wherein a Fab fragment of such antibodies inhibits alternative pathway hemolysis with $IC_{90}$ values less than 40 nM. In one embodiment, the invention provides anti-Factor D antibodies, wherein a Fab fragment of such antibodies inhibits alternative pathway hemolysis with $IC_{90}$ values less than 20 nM. In one embodiment, the invention provides anti-Factor D antibodies, wherein a Fab fragment of such antibodies inhibits alternative pathway hemolysis with $IC_{50}$ values less than 15 nM. In one example, the invention provides a fragment of said anti-Factor D antibodies (e.g. antigen-binding fragments).

In one embodiment, the invention provides anti-Factor D antibodies, wherein a Fab fragment of such antibodies inhibits alternative pathway hemolysis with $IC_{90}$ values between 80 nM and 10 nM. In one embodiment, the invention provides anti-Factor D antibodies, wherein a Fab fragment of such antibodies inhibits alternative pathway hemolysis with $IC_{90}$ values between 75 nM and 15 nM. In one embodiment, the invention provides anti-Factor D antibodies, wherein a Fab fragment of such antibodies inhibits alternative pathway hemolysis with $IC_{90}$ values between 70 nM and 20 nM. In one embodiment, the invention provides anti-Factor D antibodies, wherein a Fab fragment of such antibodies inhibits alternative pathway hemolysis with $IC_{90}$ values between 65 nM and 25 nM. In one embodiment, the invention provides anti-Factor D antibodies, wherein a Fab fragment of such antibodies inhibits alternative pathway hemolysis with $IC_{90}$ values between 60 nM and 30 nM. In one embodiment, the invention provides anti-Factor D antibodies, wherein a Fab fragment of such antibodies inhibits alternative pathway hemolysis with $IC_{90}$ values between 55 nM and 35 nM. In one embodiment, the invention provides anti-Factor D antibodies, wherein a Fab fragment of such antibodies inhibits alternative pathway hemolysis with $IC_{90}$ values between 50 nM and 40 nM. In one embodiment, the invention provides anti-Factor D antibodies, wherein a Fab fragment of such antibodies inhibits alternative pathway hemolysis with $IC_{90}$ values between 80 nM and 70 nM. In one embodiment, the invention provides anti-Factor D antibodies, wherein a Fab fragment of such antibodies inhibits alternative pathway hemolysis with $IC_{90}$ values between 55 nM and 25 nM. In one embodiment, the invention provides anti-Factor D antibodies, wherein a Fab fragment of such antibodies inhibits alternative pathway hemolysis with $IC_{90}$ values between 16 nM and 12 nM. In another embodiment, the invention provides anti-Factor D antibodies, wherein a Fab fragment of such antibodies inhibits alternative pathway hemolysis with an $IC_{90}$ value of about 14.0 nM±1.0 nM. In another embodiment, the invention provides anti-Factor D antibodies, wherein a Fab fragment of such antibodies inhibits alternative pathway hemolysis with an $IC_{90}$ value of about 38.0 nM±11.0 nM. In another embodiment, the invention provides anti-Factor D antibodies, wherein a Fab fragment of such antibodies inhibits alternative pathway hemolysis with an $IC_{90}$ value of about 72.6 nM±4.8 nM. In one example, the invention provides a fragment of said anti-Factor D antibodies (e.g. antigen-binding fragments).

In one embodiment, the invention concerns an anti-Factor D antibody, or fragment thereof (e.g. antigen-binding fragment) wherein a Fab fragment of such antibodies inhibits alternative pathway hemolysis in an antibody to Factor D molar ratio of about 0.05:1 (0.05) to about 10:1 (10), or about 0.09:1 (0.09) to about 8:1 (8), or about 0.1:1 (0.1) to about 6:1

(6), or about 0.15:1 (0.15) to about 5:1 (5), or about 0.19:1 (0.19) to about 4:1 (4), or about 0.2:1 (0.2) to about 3:1 (3), or about 0.3:1 (0.3) to about 2:1 (2), or about 0.4:1 (0.4) to about 1:1 (1), or about 0.5:1 (0.5) to about 1:2 (0.5), or about 0.6:1 (0.6) to about 1:3 (0.33), or about 0.7:1 (0.7) to about 1:4 (0.25), or about 0.8:1 (0.8) to about 1:5 (0.2) or about 0.9:1 (0.9) to about 1:6 (0.17). In one example, the invention provides a fragment of said anti-Factor D antibodies (e.g. antigen-binding fragments).

In one embodiment, the present invention includes fragments of humanized anti-Factor D antibodies (e.g. antigen-binding fragments). The antibody fragments of the present invention may, for example, be Fab, Fab', F(ab')$_2$, scFv, (scFv)$_2$, dAb, complementarity determining region (CDR) fragments, linear antibodies, single-chain antibody molecules, minibodies, diabodies, or multispecific antibodies formed from antibody fragments. In a further embodiment, the invention provides a humanized anti-Factor D antibody fragment (e.g. antigen-binding fragment) that is capable of penetrating substantially all of the retina. In an even further embodiment, the invention provides a humanized anti-Factor D antibody fragment (e.g. antigen-binding fragment) that is capable of penetrating throughout the entire thickness of the retina. In one example, the invention provides a fragment of said anti-Factor D antibodies (e.g. antigen-binding fragments).

In one embodiment, the present invention includes humanized anti-Factor D antibodies, wherein a Fab fragment of such antibodies have a half life of at least 3, 5, 7, 10 or 12 days after administration into a mammalian eye (e.g. human) via a single intravitreal injection. In another embodiment, the present invention includes humanized anti-Factor D antibodies, wherein a Fab fragment of such antibodies inhibits alternative pathway (AP) complement activation for at least 40, 45, 50, 55, 60, 65, 70, 75, 80, 85, 90, 95, 100, 105, 110 or 115 days after administration into a mammalian eye (e.g. human) via a single intravitreal injection. In another embodiment, the present invention includes humanized anti-Factor D antibodies, wherein the concentration of a Fab fragment of such antibodies that inhibits alternative pathway (AP) complement activation is maintained in retinal tissue for at least 40, 45, 50, 55, 60, 65, 70, 75, 80 or 85 days after administration into a mammalian eye (e.g. human) via a single intravitreal injection. In another embodiment, the present invention includes humanized anti-Factor D antibodies, wherein the concentration of a Fab fragment of such antibodies that inhibits alternative pathway (AP) complement activation is maintained in the vitreous humor for at least 80, 85, 90, 95, 100, 105, 110 or 115 days after administration into a mammalian eye (e.g. human) via a single intravitreal injection. In one example, the invention provides a fragment of said anti-Factor D antibodies (e.g. antigen-binding fragments).

Generation of Antibodies
Selection and Transformation of Host Cells

Host cells are transfected or transformed with expression or cloning vectors described herein for anti-Factor D antibody production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in *Mammalian Cell Biotechnology: a Practical Approach*, M. Butler, ed. (IRL Press, 1991) and Sambrook et al., supra.

Methods of eukaryotic cell transfection and prokaryotic cell transformation, which means introduction of DNA into the host so that the DNA is replicable, either as an extrachromosomal or by chromosomal integrant, are known to the ordinarily skilled artisan, for example, $CaCl_2$, $CaPO_4$, liposome-mediated, polyethylene-gycol/DMSO and electroporation. Depending on the host cell used, transformation is performed using standard techniques appropriate to such cells. The calcium treatment employing calcium chloride, as described in Sambrook et al., supra, or electroporation is generally used for prokaryotes. Infection with *Agrobacterium tumefaciens* is used for transformation of certain plant cells, as described by Shaw et al., *Gene*, 23:315 (1983) and WO 89/05859 published 29 Jun. 1989. For mammalian cells without such cell walls, the calcium phosphate precipitation method of Graham and van der Eb, *Virology*, 52:456-457 (1978) can be employed. General aspects of mammalian cell host system transfections have been described in U.S. Pat. No. 4,399,216. Transformations into yeast are typically carried out according to the method of Van Solingen et al., *J. Bact.*, 130:946 (1977) and Hsiao et al., *Proc. Natl. Acad. Sci. (USA)*, 76:3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown et al., *Methods in Enzymology*, 185:527-537 (1990) and Mansour et al., *Nature*, 336:348-352 (1988).

Suitable host cells for cloning or expressing the DNA in the vectors herein are for cloning or expressing the DNA in the vectors herein are prokaryotic, yeast, or higher eukaryotic cells. Suitable prokaryotes for this purpose include both Gram-negative and Gram-positive organisms, for example, Enterobacteria such as *Escherichia*, e.g. *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as *Bacilli*, such as *B. subtilis* and *B. licheniformis* (e.g., *B. licheniformis* 41P disclosed in DD 266,710 published 12 Apr. 1989), *Pseudomonas*, such as *P. aeruginosa*, *Rhizobia*, *Vitreoscilla*, *Paracoccus*, and *Streptomyces*. One preferred *E. coli* cloning host is *E. coli* 294 (ATCC 31,446), although other strains such as *E. coli* B, *E. coli* X1776 (ATCC 31,537), *E. coli* W3110 (ATCC 27,325) and K5 772 (ATCC 53,635) are suitable. These examples are illustrative rather than limiting. Strain W3110 is one particularly preferred host or parent host because it is a common host strain for recombinant DNA product fermentations. Preferably, the host cell secretes minimal amounts of proteolytic enzymes. For example, strain W3110 (Bachmann, *Cellular and Molecular Biology*, vol. 2 (Washington, D.C.: American Society for Microbiology, 1987), pp. 1190-1219; ATCC Deposit No. 27,325) may be modified to effect a genetic mutation in the genes encoding proteins endogenous to the host, with examples of such hosts including *E. coli* W3110 strain 1 A2, which has the complete genotype tonA; *E. coli* W3110 strain 9E4, which has the complete genotype tonA ptr3; *E. coli* W3110 strain 27C7 (ATCC 55,244), which has the complete genotype tonA ptr3phoA E15 (argF-lac)169 degP ompT kan'; *E. coli* W3110 strain 37D6, which has the complete genotype tonA ptr3 phoA E15 (argF-lac)169 degP ompT rbs7 ilvG kan$^r$; *E. coli* W3110 strain 40B4, which is strain 37D6 with a non-kanamycin resistant degP deletion mutation; *E. coli* W3110 strain 33D3 having genotype W3110 ΔfhuA (ΔtonA) ptr3 lac Iq lacL8 ΔompTΔ(nmpc-fepE) degP41 kan$^R$ (U.S. Pat. No. 5,639,635) and an *E. coli* strain having mutant periplasmic protease disclosed in U.S. Pat. No. 4,946,783 issued 7 Aug. 1990. Other strains and derivatives thereof, such as *E.* coli 294 (ATCC 31,446), *E. coli* B, *E. coli*$_x$ 1776 (ATCC 31,537) and *E. coli* RV308(ATCC 31,608) are also suitable. These examples are illustrative rather than limiting. Methods for constructing derivatives of any of the above-mentioned bacteria having defined genotypes are known in the art and described in, for example, Bass et al., *Proteins*, 8:309-314 (1990). It is generally necessary to select the appropriate bacteria taking into consideration replicability of the replicon in the cells of a bacterium. For example, *E. Coli, Serratia*, or *Salmonella* species can be suitably used as the host when well known plasmids such as pBR322, pBR325, pACYC177, or pKN410 are used to supply the replicon. Typically the host cell should secrete minimal amounts of proteolytic enzymes, and additional protease inhibitors may desirably be incorporated in the cell culture. Alternatively, in vitro methods of cloning, e.g., PCR or other nucleic acid polymerase reactions, are suitable.

Full length antibody, antibody fragments (e.g. antigen-binding fragments), and antibody fusion proteins can be produced in bacteria, in particular when glycosylation and Fc effector function are not needed, such as when the therapeutic antibody is conjugated to a cytotoxic agent (e.g., a toxin) and the immunoconjugate by itself shows effectiveness in tumor cell destruction. Full length antibodies have greater half life in circulation. Production in *E. coli* is faster and more cost efficient. For expression of antibody fragments and polypeptides in bacteria, see, e.g., U.S. Pat. No. 5,648,237 (Carter et. al.), U.S. Pat. No. 5,789,199 (Joly et al.), and U.S. Pat. No. 5,840,523 (Simmons et al.) which describes translation initiation region (TIR) and signal sequences for optimizing expression and secretion, these patents incorporated herein by reference. After expression, the antibody is isolated from the *E. coli* cell paste in a soluble fraction and can be purified through, e.g., a protein A or G column depending on the isotype. Final purification can be carried out similar to the process for purifying antibody expressed e.g, in CHO cells.

In addition to prokaryotes, eukaryotic microbes such as filamentous fungi or yeast are suitable cloning or expression hosts for antibody-encoding vectors. *Saccharomyces cerevisiae* is the most commonly used among lower eukaryotic host microorganisms. However, a number of other genera, species, and strains are commonly available and useful herein, such as *Schizosaccharomyces pombe; Kluyveromyces; Candida; Trichoderma; Neurospora crassa*; and filamentous fungi such as e.g., *Neurospora, Penicillium, Tolypocladium*, and *Aspergillus* hosts, such as *A. nidulans* and *A. niger*. Methylotropic yeasts are suitable herein and include, but are not limited to, yeast capable of growth on methanol selected from the genera consisting of *Hansenula, Candida, Kloeckera, Pichia, Saccharomyces, Torulopsis*, and *Rhodotorula*. A list of specific species that are exemplary of this class of yeasts may be found in C. Anthony, *The Biochemistry of Methylotrophs*, 269 (1982).

Suitable host cells for the expression of glycosylated antibodies are derived from multicellular organisms. In principal, any higher eukaryotic cell culture is workable, whether from vertebrate or invertebrate culture. Examples of invertebrate cells include plant and insect cells, Luckow et al., Bio/Technology 6, 47-55 (1988); Miller et al., Genetic Engineering, Setlow et al. eds. Vol. 8, pp. 277-279 (Plenam publishing 1986); Mseda et al., Nature 315, 592-594 (1985). Numerous baculoviral strains and variants and corresponding permissive insect host cells from hosts such as *Spodoptera frugiperda* (caterpillar), *Aedes* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells. Moreover, plant cells cultures of cotton, corn, potato, soybean, petunia, tomato, and tobacco and also be utilized as hosts.

Vertebrate cells, and propagation of vertebrate cells, in culture (tissue culture) has become a routine procedure. See Tissue Culture, Academic Press, Kruse and Patterson, eds. (1973). Examples of useful mammalian host cell lines are monkey kidney; human embryonic kidney line; baby hamster kidney cells; Chinese hamster ovary cells/-DHFR (CHO, Urlaub et al., Proc. Natl. Acad. Sci. USA 77: 4216 (1980)); mouse sertoli cells; human cervical carcinoma cells (HELA); canine kidney cells; human lung cells; human liver cells; mouse mammary tumor; and NS0 cells.

For recombinant production of an antibody of the invention, or antibody-fragment thereof (e.g. antigen-binding fragment), the nucleic acid (e.g., cDNA or genomic DNA) encoding it is isolated and inserted into a replicable vector for further cloning (amplification of the DNA) or for expression. DNA encoding the antibody, or fragment thereof (e.g. antigen-binding fragment) is readily isolated and sequenced using conventional procedures (e.g., by using oligonucleotide probes that are capable of binding specifically to genes encoding the heavy and light chains of the antibody). Many vectors are available. The choice of vector depends in part on the host cell to be used. Generally, preferred host cells are of either prokaryotic or eukaryotic (generally mammalian) origin.

The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The Factor D may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the anti-Factor D antibody-encoding DNA that is inserted into the vector. The signal sequence may be a prokaryotic signal sequence selected, for example, from the group of the alkaline phosphatase, penicillinase, lpp, or heat-stable enterotoxin II leaders. For yeast secretion the signal sequence may be, e.g., the yeast invertase leader, alpha factor leader (including *Saccharomyces* and *Kluyveromyces* α-factor leaders, the latter described in U.S. Pat. No. 5,010,182), or acid phosphatase leader, the *C. albicans* glucoamylase leader (EP 362,179 published 4 Apr. 1990), or the signal described in WO 90/13646 published 15 Nov. 1990. In mammalian cell expression, mammalian signal sequences may be used to direct secretion of the protein, such as signal sequences from secreted polypeptides of the same or related species, as well as viral secretory leaders.

Host cells are transformed with the above-described vectors for antibody production and cultured in conventional nutrient media modified as appropriate for inducing promoters, selecting transformants, or amplifying the genes encoding the desired sequences.

The host cells used to produce the antibody, or antibody variant or fragment (e.g. antigen-binding fragment) thereof, of this invention may be cultured in a variety of media.

a. Prokaryotic Host Cells

Prokaryotic cells used to produce the polypeptides of the invention are grown in media known in the art and suitable for culture of the selected host cells. Examples of suitable media include luria broth (LB) plus necessary nutrient supplements. In some embodiments, the media also contains a selection agent, chosen based on the construction of the expression vector, to selectively permit growth of prokaryotic cells containing the expression vector. For example, ampicillin is added to media for growth of cells expressing ampicillin resistant gene.

Any necessary supplements besides carbon, nitrogen, and inorganic phosphate sources may also be included at appropriate concentrations introduced alone or as a mixture with another supplement or medium such as a complex nitrogen source. Optionally the culture medium may contain one or more reducing agents selected from the group consisting of glutathione, cysteine, cystamine, thioglycollate, dithioerythritol and dithiothreitol.

The prokaryotic host cells are cultured at suitable temperatures. For $E.\ coli$ growth, for example, the preferred temperature ranges from about 20° C. to about 39° C., more preferably from about 25° C. to about 37° C., even more preferably at about 30° C. The pH of the medium may be any pH ranging from about 5 to about 9, depending mainly on the host organism. For $E.\ coli$, the pH is preferably from about 6.8 to about 7.4, and more preferably about 7.0.

If an inducible promoter is used in the expression vector of the invention, protein expression is induced under conditions suitable for the activation of the promoter. In one aspect of the invention, PhoA promoters are used for controlling transcription of the polypeptides. Accordingly, the transformed host cells are cultured in a phosphate-limiting medium for induction. Preferably, the phosphate-limiting medium is the C.R.A.P medium (see, e.g., Simmons et al., *J. Immunol. Methods* (2002), 263:133-147). A variety of other inducers may be used, according to the vector construct employed, as is known in the art.

In one embodiment, the expressed polypeptides of the present invention are secreted into and recovered from the periplasm of the host cells. Protein recovery typically involves disrupting the microorganism, generally by such means as osmotic shock, sonication or lysis. Once cells are disrupted, cell debris or whole cells may be removed by centrifugation or filtration. The proteins may be further purified, for example, by affinity resin chromatography. Alternatively, proteins can be transported into the culture media and isolated therein. Cells may be removed from the culture and the culture supernatant being filtered and concentrated for further purification of the proteins produced. The expressed polypeptides can be further isolated and identified using commonly known methods such as polyacrylamide gel electrophoresis (PAGE) and Western blot assay.

In one aspect of the invention, antibody production is conducted in large quantity by a fermentation process. Various large-scale fed-batch fermentation procedures are available for production of recombinant proteins. Large-scale fermentations have at least 1000 liters of capacity, preferably about 1,000 to 100,000 liters of capacity. These fermentors use agitator impellers to distribute oxygen and nutrients, especially glucose (the preferred carbon/energy source). Small scale fermentation refers generally to fermentation in a fermentor that is no more than approximately 100 liters in volumetric capacity, and can range from about 1 liter to about 100 liters.

In a fermentation process, induction of protein expression is typically initiated after the cells have been grown under suitable conditions to a desired density, e.g., an $OD_{550}$ of about 180-220, at which stage the cells are in the early stationary phase. A variety of inducers may be used, according to the vector construct employed, as is known in the art and described above. Cells may be grown for shorter periods prior to induction. Cells are usually induced for about 12-50 hours, although longer or shorter induction time may be used.

To improve the production yield and quality of the polypeptides of the invention, various fermentation conditions can be modified. For example, to improve the proper assembly and folding of the secreted antibody polypeptides, additional vectors overexpressing chaperone proteins, such as Dsb proteins (DsbA, DsbB, DsbC, DsbD and or DsbG) or FkpA (a peptidylprolyl cis,trans-isomerase with chaperone activity) can be used to co-transform the host prokaryotic cells. The chaperone proteins have been demonstrated to facilitate the proper folding and solubility of heterologous proteins produced in bacterial host cells. Chen et al. (1999) *J Bio Chem* 274:19601-19605; Georgiou et al., U.S. Pat. No. 6,083,715; Georgiou et al., U.S. Pat. No. 6,027,888; Bothmann and Pluckthun (2000) *J. Biol. Chem.* 275:17100-17105; Ramm and Pluckthun (2000) *J. Biol. Chem.* 275:17106-17113; Arie et al. (2001) *Mol. Microbiol.* 39:199-210.

To minimize proteolysis of expressed heterologous proteins (especially those that are proteolytically sensitive), certain host strains deficient for proteolytic enzymes can be used for the present invention. For example, host cell strains may be modified to effect genetic mutation(s) in the genes encoding known bacterial proteases such as Protease III, OmpT, DegP, Tsp, Protease I, Protease Mi, Protease V, Protease VI and combinations thereof. Some *E. coli* protease-deficient strains are available and described in, for example, Joly et al. (1998), supra; Georgiou et al., U.S. Pat. No. 5,264,365; Georgiou et al., U.S. Pat. No. 5,508,192; Hara et al., *Microbial Drug Resistance*, 2:63-72 (1996).

In one embodiment, *E. coli* strains deficient for proteolytic enzymes and transformed with plasmids overexpressing one or more chaperone proteins are used as host cells in the expression system of the invention.

b. Eukaryotic Host Cells

Commercially available media such as Ham's F10 (Sigma), Minimal Essential Medium (MEM, Sigma), RPMI-1640 (Sigma), and Dulbecco's Modified Eagle's Medium (DMEM, Sigma) are suitable for culturing host cells. In addition, any of the media described in Ham et al., Meth. Enzymol. 58: 44 (1979), Barnes et al., Anal. Biochem. 102: 255 (1980), U.S. Pat. Nos. 4,767,704; 4,657,866; 4,560,655; 5,122,469; 5,712,163; or 6,048,728 may be used as culture media for the host cells. Any of these media may be supplemented as necessary with hormones and/or other growth factors (such as insulin, transferrin, or epidermal growth factor), salts (such as X-chlorides, where X is sodium, calcium, magnesium; and phosphates), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Antibody Purification

Forms of anti-Factor D antibodies, or fragments thereof (e.g. antigen-binding fragments) may be recovered from culture medium or from host cell lysates. If membrane-bound, it can be released from the membrane using a suitable detergent solution (e.g. Triton-X 100) or by enzymatic cleavage. Cells employed in expression of anti-Factor D antibody can be disrupted by various physical or chemical means, such as freeze-thaw cycling, sonication, mechanical disruption, or cell lysing agents.

It may be desired to purify anti-Factor D antibody from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the anti-Factor D antibody. Various methods of protein purification may be employed and such methods are known in the art and described for example in Deutscher, *Methods in Enzymology*, 182 (1990); Scopes, *Protein Purification: Principles and Practice,* Springer-Verlag, New York (1982). The purification step(s) selected will depend, for example, on the nature of the production process used and the particular anti-Factor D antibody produced.

When using recombinant techniques, the antibody, or antibody variant or fragment (e.g. antigen-binding fragment) thereof, can be produced intracellularly, in the periplasmic space, or directly secreted into the medium. If the antibody, or antibody variant or fragment (e.g. antigen-binding fragment) thereof, is produced intracellularly, as a first step, the particulate debris, either host cells or lysed fragments, may be removed, for example, by centrifugation or ultrafiltration. Carter et al., Bio/Technology 10: 163-167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 minutes. Cell debris can be removed by centrifugation. Where the antibody, or antibody variant or fragment (e.g. antigen-binding fragment) thereof, is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel elecrophoresis, dialysis, and affinity chromatography, with affinity chromatography being one purification technique. The suitability of protein A as an affinity ligand depends on the species and isotype of any immunoglobulin Fc domain that is present in the antibody, or antibody variant or fragment (e.g. antigen-binding fragment) thereof. Protein A can be used to purify antibodies that are based on human IgG1, IgG2 or IgG4 heavy chains (Lindmark et al., J. Immunol Meth. 62: 1-13 (1983)). Protein G is recommended for all mouse isotypes and for human IgG3 (Guss et al., EMBO J. 5: 1567-1575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody, or antibody variant or fragment (e.g. antigen-binding fragment) thereof, comprises a CH3 domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody, or antibody variant or fragment (e.g. antigen-binding fragment) thereof, to be recovered.

Following any preliminary purification step(s), the mixture comprising the antibody, or antibody variant or fragment (e.g. antigen-binding fragment) thereof, of interest and contaminants may be subjected to low pH hydrophobic interaction chromatography using an elution buffer at a pH between about 2.5-4.5, preferably performed at low salt concentrations (e.g., from about 0-0.25M salt).

Pharmaceutical Formulations

Therapeutic formulations of the polypeptide or antibody, or antibody fragment thereof (e.g. antigen-binding fragment), or antibody variant thereof, may be prepared for storage as lyophilized formulations or aqueous solutions by mixing the polypeptide having the desired degree of purity with optional "pharmaceutically-acceptable" carriers, excipients or stabilizers typically employed in the art (all of which are termed "excipients"). For example, buffering agents, stabilizing agents, preservatives, isotonifiers, non-ionic detergents, antioxidants and other miscellaneous additives. (See Remington's Pharmaceutical Sciences, 16th edition, A. Osol, Ed. (1980)). Such additives must be nontoxic to the recipients at the dosages and concentrations employed.

Buffering agents help to maintain the pH in the range which approximates physiological conditions. They are preferably present at concentration ranging from about 2 mM to about 50 mM. Suitable buffering agents for use with the present invention include both organic and inorganic acids and salts thereof such as citrate buffers (e.g., monosodium citrate-disodium citrate mixture, citric acid-trisodium citrate mixture, citric acid-monosodium citrate mixture, etc.), succinate buffers (e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers (e.g., fumaric acid-monosodium fumarate mixture, etc.), fumarate buffers (e.g., fumaric acid-monosodium fumarate mixture, fumaric acid-disodium fumarate mixture, monosodium fumarate-disodium fumarate mixture, etc.), gluconate buffers (e.g., gluconic acid-sodium glyconate mixture, gluconic acid-sodium hydroxide mixture, gluconic acid-potassium glyuconate mixture, etc.), oxalate buffer (e.g., oxalic acid-sodium oxalate mixture, oxalic acid-sodium hydroxide mixture, oxalic acid-potassium oxalate mixture, etc.), lactate buffers (e.g., lactic acid-sodium lactate mixture, lactic acid-sodium hydroxide mixture, lactic acid-potassium lactate mixture, etc.) and acetate buffers (e.g., acetic acid-sodium acetate mixture, acetic acid-sodium hydroxide mixture, etc.). Additionally, there may be mentioned phosphate buffers, histidine buffers and trimethylamine salts such as Tris.

Preservatives may be added to retard microbial growth, and may be added in amounts ranging from 0.2%-1% (w/v). Suitable preservatives for use with the present invention include phenol, benzyl alcohol, meta-cresol, methyl paraben, propyl paraben, octadecyldimethylbenzyl ammonium chloride, benzalconium halides (e.g., chloride, bromide, iodide), hexamethonium chloride, alkyl parabens such as methyl or propyl paraben, catechol, resorcinol, cyclohexanol, and 3-pentanol.

Isotonicifiers sometimes known as "stabilizers" may be added to ensure isotonicity of liquid compositions of the present invention and include polhydric sugar alcohols, preferably trihydric or higher sugar alcohols, such as glycerin, erythritol, arabitol, xylitol, sorbitol and mannitol.

Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols (enumerated above); amino acids such as arginine, lysine, glycine, glutamine, asparagine, histidine, alanine, ornithine, L-leucine, 2-phenylalanine, glutamic acid, threonine, etc., organic sugars or sugar alcohols, such as lactose, trehalose, stachyose, mannitol, sorbitol, xylitol, ribitol, myoinisitol, galactitol, glycerol and the like, including cyclitols such as inositol; polyethylene glycol; amino acid polymers; sulfur containing reducing agents, such as urea, glutathione, thioctic acid, sodium thioglycolate, thioglycerol, .alpha.-monothioglycerol and sodium thio sulfate; low molecular weight polypeptides (i.e. <10 residues); proteins such as human serum albumin, bovine serum albumin, gelatin or immunoglobulins; hydrophylic polymers, such as polyvinylpyrrolidone monosaccharides, such as xylose, mannose, fructose, glucose; disaccharides such as lactose, maltose, sucrose and trisaccacharides such as raffinose; polysaccharides such as dextran. Stabilizers may be present in the range from 0.1 to 10,000 weights per part of weight active protein.

Non-ionic surfactants or detergents (also known as "wetting agents") may be added to help solubilize the therapeutic agent as well as to protect the therapeutic protein against agitation-induced aggregation, which also permits the formulation to be exposed to shear surface stressed without causing denaturation of the protein. Suitable non-ionic surfactants include polysorbates (20, 80, etc.), polyoxamers (184, 188 etc.), Pluronic® polyols, polyoxyethylene sorbitan monoethers (Tween®-20, Tween®-80, etc.). Non-ionic surfactants may be present in a range of about 0.05 mg/ml to about 1.0 mg/ml, preferably about 0.07 mg/ml to about 0.2 mg/ml.

Additional miscellaneous excipients include bulking agents, (e.g. starch), chelating agents (e.g. EDTA), antioxidants (e.g., ascorbic acid, methionine, vitamin E), and cosolvents. The formulation herein may also contain more than one active compound as necessary for the particular indication being treated, preferably those with complementary activities that do not adversely affect each other. For example, it may be desireable to further provide an immunosuppressive agent. Such molecules are suitably present in combination in amounts that are effective for the purpose intended. The active ingredients may also be entrapped in microcapsule prepared, for example, by coascervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences, 16th edition, A. Osal, Ed. (1980).

The formulations to be used for in vivo administration must be sterile. This is readily accomplished, for example, by filtration through sterile filtration membranes. Sustained-release preparations may be prepared. Suitable examples of sustained-release preparations include semi-permeable matrices of solid hydrophobic polymers containing the antibody, or antibody variant or fragment (e.g. antigen-binding fragment) thereof, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C. resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

The compounds of the invention for prevention or treatment of an ocular disease or condition are typically administered by ocular, intraocular, and/or intravitreal injection, and/or juxtascleral injection, and/or subtenon injection, and/or superchoroidal injection and/or topical administration in the form of eyedrops and/or ointment. Such compounds of the invention may be delivered by a variety of methods, e.g. intravitreally as a device and/or a depot that allows for slow release of the compound into the vitreous, including those described in references such as Intraocular Drug Delivery, Jaffe, Jaffe, Ashton, and Pearson, editors, Taylor & Francis (March 2006). In one example, a device may be in the form of a minpump and/or a matrix and/or a passive diffusion system and/or encapsulated cells that release the compound for a prolonged period of time (Intraocular Drug Delivery, Jaffe, Jaffe, Ashton, and Pearson, editors, Taylor & Francis (March 2006). Other methods of administration may also be used, which includes but is not limited to, topical, parenteral, subcutaneous, intraperitoneal, intrapulmonary, intranasal, and intralesional administration. Parenteral infusions include intramuscular, intravenous, intraarterial, intraperitoneal, or subcutaneous administration.

Formulations for ocular, intraocular or intravitreal administration can be prepared by methods and using ingredients known in the art. A main requirement for efficient treatment is proper penetration through the eye. Unlike diseases of the front of the eye, where drugs can be delivered topically, retinal diseases require a more site-specific approach. Eye drops and ointments rarely penetrate the back of the eye, and the blood-ocular barrier hinders penetration of systemically administered drugs into ocular tissue. Accordingly, usually the method of choice for drug delivery to treat retinal disease, such as AMD and CNV, is direct intravitreal injection. Intravitrial injections are usually repeated at intervals which depend on the patient's condition, and the properties and half-life of the drug delivered. For intraocular (e.g. intravitreal) penetration, usually molecules of smaller size are preferred.

The efficacy of the treatment of complement-associated eye conditions, such as AMD or CNV, can be measured by various endpoints commonly used in evaluating intraocular diseases. For example, vision loss can be assessed. Vision loss can be evaluated by, but not limited to, e.g., measuring by the mean change in best correction visual acuity (BCVA) from baseline to a desired time point (e.g., where the BCVA is based on Early Treatment Diabetic Retinopathy Study (ETDRS) visual acuity chart and assessment at a test distance of 4 meters), measuring the proportion of subjects who lose fewer than 15 letters in visual acuity at a desired time point compared to baseline, measuring the proportion of subjects who gain greater than or equal to 15 letters in visual acuity at a desired time point compared to baseline, measuring the proportion of subjects with a visual-acuity Snellen equivalent of 20/2000 or worse at a desired time point, measuring the NEI Visual Functioning Questionnaire, measuring the size of CNV and amount of leakage of CNV at a desired time point, e.g., by fluorescein angiography, etc. Ocular assessments can be done, e.g., which include, but are not limited to, e.g., performing eye exam, measuring intraocular pressure, assessing visual acuity, measuring slitlamp pressure, assessing intraocular inflammation, etc.

The amount of therapeutic polypeptide, antibody, or antibody variant thereof, or fragment thereof (e.g antigen-binding fragment) which will be effective in the treatment of a particular disorder or condition will depend on the nature of the disorder or condition, and can be determined by standard clinical techniques. Where possible, it is desirable to determine the dose-response curve and the pharmaceutical compositions of the invention first in vitro, and then in useful animal model systems prior to testing in humans.

In one embodiment, an aqueous solution of therapeutic polypeptide, antibody, or antibody variant thereof, or fragment thereof (e.g. antigen-binding fragment), is administered by subcutaneous injection. In another embodiment, an aqueous solution of therapeutic polypeptide, antibody, or antibody variant thereof, or fragment thereof (e.g. antigen-binding fragment) is administered by intravitreal injection. Each dose may range from about 0.5 µg to about 50 µg per kilogram of body weight, or more preferably, from about 3 µg to about 30 µg per kilogram body weight.

The dosing schedule for subcutaneous administration may vary form once a month to daily depending on a number of clinical factors, including the type of disease, severity of disease, and the subject's sensitivity to the therapeutic agent.

The following examples are offered for illustrative purposes only, and are not intended to limit the scope of the present invention in any way.

All patent and literature references cited in the present specification are hereby expressly incorporated by reference in their entirety.

Articles of Manufacture and Kits

Another embodiment of the invention is an article of manufacture containing materials useful for the treatment, prevention and/or diagnosis of conditions targeted by the antibodies of the invention, or variants thereof or fragments thereof (e.g. antigen-binding fragments). For example, the invention concerns an article of manufacture containing materials useful for the treatment, prevention and/or diagnosis of complement-associated disorders. The article of manufacture comprises a container and a label or package insert on or associated with the container. Suitable containers include, for example, bottles, vials, syringes, etc. The containers may be formed from a variety of materials such as glass or plastic. The container holds a composition which is effective for treating, preventing and/or diagnosis of the complement-associated condition and may have a sterile access port (for example the container may be an intravenous solution bag or a vial having a stopper pierceable by a hypodermic injection needle). At least one active agent in the composition is an anti-Factor D antibody, or fragment thereof (e.g. antigen-binding fragment) of the invention. The label or package insert indicates that the composition is useful for treatment, prevention and/or diagnosis of a particular condition.

Package insert refers to instructions customarily included in commercial packages of therapeutic products that contain information about the indications, usage, dosage, administration, contraindications and/or warnings concerning the use of such therapeutic products. In one embodiment, the label or package insert indicates that the composition is used for treating complement-associated disorders, such as, for example, any of the conditions listed before, including eye disorders e.g. iage-related macular degeneration (AMD). The label or package insert will further comprise instructions for administering the antibody composition to the patient.

Additionally, the article of manufacture may further comprise a second container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In another embodiment, kits are also provided that are useful for various purposes, e.g., for treatment, prevention and/or diagnosis of complement-associated disorders, for complement-associated hemolysis assays, for purification or immunoprecipitation of Factor D polypeptide from cells. For isolation and purification of Factor D polypeptide, the kit can contain an anti-Factor D antibody coupled to beads (e.g., sepharose beads). Kits can be provided which contain the antibodies for detection and quantitation of Factor D polypeptide in vitro, e.g., in an ELISA or a Western blot. As with the article of manufacture, the kit comprises a container and a label or package insert on or associated with the container. The container holds a composition comprising at least one anti-Factor antibody, or fragment thereof (e.g. antigen-binding fragment) of the invention. Additional containers may be included that contain, e.g., diluents and buffers, control antibodies. The label or package insert may provide a description of the composition as well as instructions for the intended in vitro or detection use. The label or package insert may provide instructions for the administration (e.g. the antibody, or antibody fragment thereof (e.g. antigen-binding fragment) to a subject.

Uses for the Humanized Antibody

The humanized antibodies, or fragments thereof (e.g. antigen-binding fragments) or variant thereof, of the present invention are useful in diagnostic assays, e.g., for detecting expression of a target of interest in specific cells, tissues, or serum. For diagnostic applications, the antibody, or antibody variant thereof or fragment thereof (e.g. antigen-binding fragment), typically will be labeled with a detectable moiety. Numerous labels are available. Techniques for quantifying a change in fluorescence are described above. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, .beta.-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al., Methods for the Preparation of Enzyme-Antibody Conjugates for Use in Enzyme Immunoassay, in Methods in Enzym. (Ed. J. Langone & H. Van Vunakis), Academic press, New York, 73: 147-166 (1981).

Sometimes, the label is indirectly conjugated with the antibody, or antibody variant thereof or fragment thereof (e.g. antigen-binding fragment). The skilled artisan will be aware of various techniques for achieving this. For example, the antibody, or antibody variant thereof or fragment thereof (e.g. antigen-binding fragment), can be conjugated with biotin and any of the three broad categories of labels mentioned above can be conjugated with avidin, or vice versa. Biotin binds selectively to avidin and thus, the label can be conjugated with the antibody, or antibody variant thereof or fragment thereof (e.g. antigen-binding fragment), in this indirect manner. Alternatively, to achieve indirect conjugation of the label with the antibody, or antibody variant thereof or fragment thereof (e.g. antigen-binding fragment), the antibody, or antibody variant thereof or fragment thereof (e.g. antigen-binding fragment), is conjugated with a small hapten (e.g. digloxin) and one of the different types of labels mentioned above is conjugated with an anti-hapten antibody, or antibody variant thereof (e.g. anti-digloxin antibody) or fragment thereof (e.g. antigen-binding fragment). Thus, indirect conjugation of the label with the antibody, or antibody variant thereof or fragment thereof (e.g. antigen-binding fragment), can be achieved.

In another embodiment of the invention, the antibody, or antibody variant thereof or fragment thereof (e.g. antigen-binding fragment), need not be labeled, and the presence thereof can be detected using a labeled antibody which binds to the antibody, or antibody variant thereof or fragment thereof (e.g. antigen-binding fragment).

The antibodies, or antibody variants thereof, or fragment thereof (e.g. antigen-binding fragment) of the present invention may be employed in any known assay method, such as competitive binding assays, direct and indirect sandwich assays, and immunoprecipitation assays. Zola, Monoclonal Antibodies: A Manual of Techniques, pp. 147-158 (CRC Press, Inc. 1987).

Competitive binding assays rely on the ability of a labeled standard to compete with the test sample for binding with a limited amount of antibody, or antibody variant thereof or fragment thereof (e.g. antigen-binding fragment). The amount of target in the test sample is inversely proportional to the amount of standard that becomes bound to the antibodies. To facilitate determining the amount of standard that becomes bound, the antibodies generally are insolubilized before or after the competition. As a result, the standard and test sample that are bound to the antibodies may conveniently be separated from the standard and test sample which remain unbound.

Sandwich assays involve the use of two antibodies, or fragments thereof (e.g. antigen-binding fragments) each capable of binding to a different immunogenic portion, or epitope, or the protein to be detected. In a sandwich assay, the test sample to be analyzed is bound by a first antibody which is immobilized on a solid support, and thereafter a second antibody binds to the test sample, thus forming an insoluble three-part complex. See e.g., U.S. Pat. No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

For immunohistochemistry, the tumor sample may be fresh or frozen or may be embedded in paraffin and fixed with a preservative such as formalin, for example.

The antibodies, or antibody variants thereof, or fragments thereof (e.g. antigen-binding fragments) may also be used for in vivo diagnostic assays. Generally, the antibody, or antibody variant thereof or fragment thereof (e.g. antigen-binding fragment), is labeled with a radionucleotide (such as $^{111}$In, $^{99}$Tc, $^{14}$C, $^{131}$I, $^{3}$H, $^{32}$P or $^{35}$S) so that the tumor can be localized using immunoscintiography. For example, a high affinity anti-IgE antibody of the present invention may be used to detect the amount of IgE present in, e.g., the lungs of an asthmatic patient.

The antibody, or antibody variant thereof or fragment thereof (e.g. antigen-binding fragment), of the present invention can be provided in a kit, i.e., packaged combination of reagents in predetermined amounts with instructions for performing the diagnostic assay. Where the antibody, or antibody variant thereof or fragment thereof (e.g. antigen-binding fragment), is labeled with an enzyme, the kit may include substrates and cofactors required by the enzyme (e.g., a substrate precursor which provides the detectable chromophore or fluorophore). In addition, other additives may be included such as stabilizers, buffers (e.g., a block buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

In Vivo uses for the Antibody

It is contemplated that the antibodies, or antibodies thereof, or fragments thereof (e.g. antigen-binding fragments) of the present invention may be used to treat a mammal. In one embodiment, the antibody, or antibody thereof, is administered to a nonhuman mammal for the purposes of obtaining preclinical data, for example. Exemplary nonhuman mammals to be treated include nonhuman primates, dogs, cats, rodents and other mammals in which preclinical studies are performed. Such mammals may be established animal models for a disease to be treated with the antibody, or antibody thereof, or may be used to study toxicity of the antibody of interest. In each of these embodiments, dose escalation studies may be performed on the mammal.

The antibody, or variant thereof, or fragment thereof (e.g. antigen-binding fragment) or polypeptide is administered by any suitable means, including parenteral, subcutaneous, intraperitoneal, intrapulmonary, and intranasal, and, if desired for local immunosuppressive treatment, intralesional administration. Parenteral infusions include intramuscular, intravenous, intraarterial, intraperitoneal, or subcutaneous administration. In addition, the antibody, or antibody variant thereof or fragment thereof (e.g. antigen-binding fragment), is suitably administered by pulse infusion, particularly with declining doses of the antibody, or antibody variant thereof or fragment thereof (e.g. antigen-binding fragment). Preferably the dosing is given by injections, most preferably intravenous or subcutaneous injections, depending in part on whether the administration is brief or chronic.

For the prevention or treatment of disease, the appropriate dosage of the antibody, or antibody variant thereof or fragment thereof (e.g. antigen-binding fragment), or polypeptide will depend on the type of disease to be treated, the severity and course of the disease, whether the antibody, or antibody variant thereof or fragment thereof (e.g. antigen-binding fragment), is administered for preventive or therapeutic purposes, previous therapy, the patient's clinical history and response to the antibody, or antibody variant thereof or fragment thereof (e.g. antigen-binding fragment) and the discretion of the attending physician.

Depending on the type and severity of the disease, about 0.1 mg/kg to 150 mg/kg (e.g., 0.1-20 mg/kg) of antibody, or antibody variant thereof or fragment thereof (e.g. antigen-binding fragment), is an initial candidate dosage for administration to the patient, whether, for example, by one or more separate administrations, or by continuous infusion. A typical daily dosage might range from about 1 mg/kg to 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays. An exemplary dosing regimen is disclosed in WO 94/04188.

The antibody compositions may be formulated, dosed and administered in a manner consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the antibody, or antibody variant thereof or fragment thereof (e.g. antigen-binding fragment), to be administered will be governed by such considerations, and is the minimum amount necessary to prevent, ameliorate, or treat a disease or disorder. The antibody, or antibody variant thereof or fragment thereof (e.g. antigen-binding fragment), need not be, but is optionally formulated with one or more agents currently used to prevent or treat the disorder in question. The effective amount of such other agents depends on the amount of antibody, or antibody variant thereof or fragment thereof (e.g. antigen-binding fragment), present in the formulation, the type of disorder or treatment, and other factors discussed above. These are generally used in the same dosages and with administration routes as used hereinbefore or about from 1 to 99% of the heretofore employed dosages.

The antibodies, or antibody variants thereof, or fragments thereof (e.g. antigen-binding fragments) of the present invention which recognize Factor D as their target may be used to treat complement-mediated disorders. These disorders are associated with excessive or uncontrolled complement activation. They include: Complement activation during cardiopulmonary bypass operations; complement activation due to ischemia-reperfusion following acute myocardial infarction, aneurysm, stroke, hemorrhagic shock, crush injury, multiple organ failure, hypobolemic shock and intestinal ischemia. These disorders can also include disease or condition is an inflammatory condition such as severe burns, endotoxemia, septic shock, adult respiratory distress syndrome, hemodialysis; anaphylactic shock, severe asthma, angioedema, Crohn's disease, sickle cell anemia, poststreptococcal glomerulonephritis and pancreatitis. The disorder may be the result of an adverse drug reaction, drug allergy, IL-2 induced vascular leakage syndrome or radiographic contrast media allergy. It also includes autoimmune disease such as systemic lupus erythematosus, myasthenia gravis, rheumatoid arthritis, Alzheimer's disease and multiple sclerosis. Complement activation is also associated with transplant rejection. Recently there has been a strong correlation shown between complement activation and ocular diseases such as age-related macular degeneration, diabetic retinopathy and other ischemia-related retinopathies, choroidal neovascularization (CNV), uveitis, diabetic macular edema, pathological myopia, von Hippel-Lindau disease, histoplasmosis of the eye, Central Retinal Vein Occlusion (CRVO), corneal neovascularization, and retinal neovascularization.

EXAMPLES

The following examples are offered by way of illustration and not by way of limitation. Commercially available reagents referred to in the examples were used according to manufacturer's instructions unless otherwise indicated. The source of those cells identified in the following examples, and throughout the specification, by ATCC accession numbers is the American Type Culture Collection, 10801 University Boulevard, Manassas, Va. 20110-2209.

Example 1

Modification of Anti-Factor D Abs

To identify modified anti-Factor D antibodies, and variants thereof, and fragments thereof (e.g. antigen-binding fragments) that would have commercially desireable characteristics such as homogeneity during manufacturing and production or for purposes of analytical characterization, a site-directed mutagenesis approach was used to generate modified humanized anti-factor D antibodies, and variants thereof, and fragments thereof (e.g. antigen-binding fragments). First, the variable heavy and light chain domains from humanized anti-Factor D Fab clone #111 (SEQ ID NO: 2 and SEQ ID NO: 1, respectively) were subcloned into an expression plasmid. Secondly, oligonucleotides encoding single mutations were annealed to the resulting expression plasmid to introduce the site-directed mutations.

Initially, the variable heavy and light chain domains of humanized anti-Factor D Fab clone #111 were subcloned into the plasmid pAEP1 (pAEP1 is a plasmid for the expression of Fab antibodies in *E. coli*.), with the subcloning resulting in the introduction of a valine (V) at position 104 (according to Kabat numbering, see FIG. 10) of the variable light chain domain.

The subcloning of the variable light chain domain domain of humanized anti-Factor D Fab clone #111 into pAEP1 involved the ligation of two DNA fragments. The first fragment was the pAEP1 vector in which the small EcoRV/KpnI fragment had been removed. The second fragment was an approximately 300 base pair EcoRV-KpnI PCR fragment generated from the light chain plasmid for the humanized anti-Factor D Fab clone #111, using the following primers:

```
                                                    (SEQ ID NO: 67)
5'-TTTCCCTTTGATATCCAGGTGACCCAGTCTCCATCCT-3'

(SEQ ID NO: 68)
5'-TTTCCCTTTGGTACCCTGGCCAAACGTGTACGGCAAAGAATC-3'.
```

The subcloning of the variable light chain domain of humanized anti-Factor D clone #111 into pAEP1 introduced a valine (V) at position 104 because position 104 is 2 amino acids downstream of the restriction endonuclease sites, EcoRV and KpnI, which were used to insert the variable light chain domain of humanized anti-Factor D clone #111 into pAEP1 and therefore in the backbone of the pAEP1 plasmid. This resulting intermediate plasmid is herein referred to as "pAEP1-283-VL".

The subcloning of the variable heavy chain domain of humanized anti-Factor D clone #111 into pAEP1-238-VL involved the ligation of two DNA fragments. The first fragment was the pAEP1-238-VL vector in which the small BsiWI/PspOMI fragment had been removed. The second fragment was an approximately 364 base pair BsiWI-PspOMI PCR fragment generated from the heavy chain plasmid for the humanized anti-Factor D Fab clone #111, using the following primers:

```
                                         (SEQ ID NO: 69)
5'-TTTGGGTTTCGTACGCTCAGGTCCAGCTGGTGCAATCTGGG-3'

(SEQ ID NO: 70)
5'-TTTGGGTTTGGGCCCTTGGTGGAGGCTGAGGAGACGGTGACCAGGG
T-3'.
```

This ligation of the two DNA fragments resulted in the plasmid for humanized anti-Factor D Fab antibody variant 238 (also herein referred to as "238"; plasmid is herein referred to as "p238").

After the subcloning of the variable light and heavy chain domains from humanized anti-Factor D #111, site-directed PCR mutagenesis was used to mutate the glutamine (Q) at position 1 (according to Kabat numbering, see FIG. 1) of the variable heavy chain of humanized anti-Factor D Fab antibody variant 238 to a glutamate (E), resulting in humanized anti-Factor D Fab antibody variant 238-1 (also herein referred to as "238-1"). The construction of the plasmid for humanized anti-Factor D Fab antibody variant 238-1 (plasmid is herein referred to as "p238-1") involved the ligation of two DNA fragments. The first fragment was the p238 vector in which the small BsiWI/PspOMI fragment had been removed. The second fragment was an approximately 364 base pair BsiWI-PspOMI PCR fragment generated from the p238 plasmid, using the following primers:

```
                                         (SEQ ID NO: 71)
5'-TTTGGGTTTCGTACGCTGAAGTCCAGCTGGTGCAATCTGGG-3'

(SEQ ID NO: 72)
5'-TTTGGGTTTGGGCCCTTGGTGGAGGCTGAGGAGACGGTGACCAGGG
T-3'.
```

This ligation of the two DNA fragments resulted in the plasmid for humanized anti-Factor D Fab antibody variant 238-1 (also herein referred to as "238-1"; plasmid is herein referred to as "p238-1"), which included the site-directed mutation of the position 1 to a glutamate (E). This mutation was found to inhibit the partial conversion of the glutamine (Q) in humanized anti-Factor D Fab antibody variant 238-1 to pyroglutamate (Amphlett, G. et al., *Pharm. Biotechnol.*, 9:1-140 (1996)).

Further site-directed PCR mutagenesis may be used to mutate methionine (M or Met) or tryptophan (W or Trp) residues to prevent oxidation or to mutate asparagine (N or Asn) residues to prevent deamidation. To prevent the formation of oxidized variants of the humanized anti-Factor D antibodies, methionines (M or Met), for example at position 33 of the light chain may be mutated to leucine (L or Leu) which is most similar in size and hydrophobicity to methionine, but lacks a sulfur for oxidation, or alternatively mutated to isoleucine (I or Ile) (Amphlett, G. et al., *Pharm. Biotechnol.*, 9:1-140 (1996)). To prevent the formation of deamidated variants of the humanized anti-Factor D antibodies, asparagines (N or Asn), for example at position 34 and 52 of the light chain or position 99 or 100 of the heavy chain may be mutated to glutamine (Q or Gln) which is most similar chemically to asparagine (N or Asn), or mutated to alanine (A or Ala) or serine (S or Ser) which are common substitutions at those positions in other antibodies (Amphlett, G. et al., Pharm. Biotechnol., 9:1-140 (1996)).

FIGS. 1-2 shows the variable light chain domain and variable heavy chain domain sequences for humanized anti-Factor D Fab antibody variant 238 (SEQ ID Nos: 6 and 18, respectively) and humanized anti-Factor D Fab antibody variant 238-1 (SEQ ID NOs: 7 and 19, respectively). FIG. 4 and FIG. 6 show the light chain and heavy chain sequences (SEQ ID NOs: 47 and 54, respectively) for humanized anti-Factor D Fab antibody variant 238. FIG. 8 and FIG. 10 show the light chain and heavy chain sequences (SEQ ID NOs: 61 and 63, respectively) for humanized anti-Factor D Fab antibody variant 238-1.

BiaCore data showed affinity of humanized anti-Factor D Fab antibody variant 238 to human Factor D as well as affinity of humanized anti-Factor D full-length mAb version of clone #111 (humanized anti-Factor D full-length mAb 234) (herein referred to as "234" or "anti-Factor D full-length mAb 234" or "humanized anti-Factor D full-length MAb 234") (Table 2). Humanized anti-Factor D Fab antibody variants 238 and 238-1 were also tested in the hemolytic inhibition assay (FIG. 11) to assess the inhibition of the alternative pathway (see Example 3).

Example 2

AP Hemolysis Assay

Biological function of modified anti-Factor D Abs were determined using hemolytic inhibition assay using C1q-depleted human serum and BiaCore analysis (See Example 3 below). Hemolytic assay was performed as follows.

For determining alternative pathway activity, rabbit erythrocytes (Er, Colorado Serum) were washed 3× in GVB and resuspended to $2\times10^9$/ml. Inhibitors (50 µl) and 20 µl of Er suspension were mixed 1:1 with GVB/0.1 M EGTA/0.1 M $MgCl_2$. Complement activation was initiated by the addition of C1q-depleted human serum (to avoid any complement activation through the classical pathway) (CompTech; 30 µl diluted 1:3 in GVB). After a 30 minute incubation at room temperature, 200 µl GVB/10 mM EDTA were added to stop the reaction and samples were centrifuged for 5 min at 500 g. Hemolysis was determined in 200 µl supernatant by measuring absorbance at 412 nm. Data were expressed as % of hemolysis induced in the absence of the inhibitor.

FIG. 11 shows inhibition of humanized anti-Factor D Fab clone #111 ($IC_{50}$=4.7±0.6 nM), modified anti-Factor D Fab 238 ($IC_{50}$=6.4+0.6 nM) and modified anti-Factor D Fab 238-1 ($IC_{50}$=3.5+0.5 nM) on alternative pathway hemolysis using rabbit red blood cell hemolysis assay using C1q-depleted human serum as complement source. Controls were Factor H ("Human fH") (from CompTech) and anti-glycoprotein 120 ("xgp120") antibodies.

Example 3

Kinetic Analysis of anti-Human Factor D Fab by BiaCore

Kinetic and affinity constants for binding of human Factor D (Advanced Research, Inc.) to immobilized modified anti-factor D Fab 238 (herein referred to as "238"; see Example 1) were determined by surface plasmon resonance measurements on both BiaCore 3000 and BiaCore A100 instruments. For the values in Table 2 that are listed as "BiaCore 3000/BiaCore A100" results, separate experiments were done on each instrument, the data from the separate experiments were analyzed to get kinetic constants, and the kinetic constants were averaged to get the values shown in Table 2. Alternatively, kinetic and affinity constants for binding of human Factor D may be measured by immobilizing human Factor D and measuring the binding of the mAb or Fab, may be measured using different regeneration conditions (e.g. comprising 4M $MgCl_2$) and/or may be measured using different binding buffers (e.g. comprising PBS). Humanized anti-factor D full-length mAb version of clone #111 (herein referred to as "234" or "anti-Factor D full-length mAb 234" or "humanized anti-Factor D full-length mAb 234") was also analyzed.

1. Immobilization mAb or Fab were immobilized via amine-coupling using a standard protocol supplied by the manufacturer. The density of the coupling was regulated by adjusting the concentration or pH of the injected mAb or Fab solutions such that the total signal for saturating binding of human factor D was between 50 and 150 resonance units (RU). After coupling of the desired amount of mAb or Fab, unreacted functional groups on the sensor chip were blocked by injection of ethanolamine.

2. Kinetic Analysis

Binding experiments were conducting by injecting 60 μL aliquots of a series of human factor D solutions varied in concentration from 500 nM to 0.98 nM in 2-fold increments. All samples were diluted in running buffer composed of 150 mM NaCl, 0.01% Tween-20 and one of the following buffer components: (a) pH 7.2 (10 mM HEPES (4-(2-hydroxyethyl)-1-piperazineethanesulfonic acid); (b) pH 6.0 (10 mM MES (2-[N-Morpholino]ethanesulfonic acid); or pH 5.0 (10 mM sodium acetate). The flow rate was 30 μL/min and dissociation was monitored for 10 minutes for each concentration of human factor D tested. The signal (sensorgram) observed for injection of the same solutions over a reference cell (ethanolamine blocked) was subtracted from the sensorgram. Between sensorgrams the surface was regenerated by injection of 30 μL of 4 M $MgCl_2$ to cause dissociation of any human factor D remaining bound to the immobilized antibody. A control sensorgram recorded for injection of buffer only over the sensor chip surface was subtracted from the human factor D sensorgrams. These data were analyzed by non-linear regression according to a 1:1 Langmuir binding model using BIAevaluation software v4.1. Kinetic and affinity constants are provided in the Table 2 below. BiaCore technology is limited and is not able to accurately measure on-rates that are too fast (i.e. $K_D$ values smaller than about 10 pM) (Safsten et al., *Anal. Biochem.*, 353: 181 (2006)).

TABLE 2

BiaCore Results

| Fab or Antibody | ka (M−1s−1) | kd (s−1) | $K_D$ (M) |
|---|---|---|---|
| Modified Anti-factor D Fab 238 (pH 7.2; A100) | $1.5 \times 10^8$ | $1.7 \times 10^{-4}$ | $1.0 \times 10^{-12}$ (1.0 pM ± 0.05) |
| Modified Anti-factor D Fab 238 (pH 7.2; 3000/A100) | $8.4 \pm 9 \times 10^8$ | $1.4 \pm 1.7 \times 10^{-3}$ | $1.4 \times 10^{-12}$ (1.4 pM ± 0.5) |
| Modified Anti-factor D Fab 238 (pH 6; 3000) | $1.9 \times 10^6$ | $3.6 \times 10^{-4}$ | $0.19 \times 10^{-9}$ (0.19 nM ± 0.01) |
| Modified Anti-factor D Fab 238 (pH 5; A100) | $1.2 \times 10^6$ | 0.02 | $12.3 \times 10^{-9}$ (12.3 nM ± 2) |
| Anti-factor D full-length mAb 234 (pH 7.2; A100) | $1.9 \times 10^8$ | $1.3 \times 10^{-4}$ | $0.7 \times 10^{-12}$ (0.7 pM ± 0.04) |
| Anti-factor D full-length mAb 234 (pH 7.2; 3000/A100) | $9.5 \pm 10 \times 10^8$ | $1.3 \pm 1.7 \times 10^{-3}$ | $1.1 \times 10^{-12}$ (1.1 pM ± 0.6) |
| Anti-factor D full-length mAb 234 (pH 6; 3000) | $2.8 \times 10^6$ | $2.2 \times 10^{-4}$ | $.08 \times 10^{-9}$ (0.08 nM ± 0.01) |
| Anti-factor D full-length mAb 234 (pH 5; A100) | $2.2 \times 10^6$ | $2.0 \times 10^{-2}$ | $9 \times 10^{-9}$ (9.0 nM ± 1.0) |

Example 4

AP Hemolysis Assay with Varying Factor D Concentrations

Biological function of modified anti-Factor D Abs, including anti-Factor D Fab 238, were determined using hemolytic inhibition assay using C1q-depleted human serum and Bia-Core analysis (See Example 2 above), in the presence of three serum concentrations of Factor D.

C1q-depleted human serum (CompTech) as well as vitreous fluid and Bruch's membrane tissue from eyes of AMD patients (obtained through a collaboration with the Cole Eye Institute, Cleveland, Ohio) were analyzed in a quantitative ELISA for Factor D (see below). The concentration of Factor D in the C1q-depleted serum was 97 nM, whereas the level in vitreous fluid and Bruch's membrane tissue from AMD patients was 16.2±10.3 nM (mean±SD, n=10).

The quantitative factor D ELISA was performed by diluting anti-human complement factor D goat polyclonal antibody (R&D Systems, Minneapolis, Minn.) to 1 μg/mL in phosphate buffered saline (PBS) and coating the anti-factor D polyclonal antibody (R&D Systems, Minneapolis, Minn.) onto 384 well ELISA plates (high-bind plates; Greiner Bio One through VWR International, Bridgeport, N.J.) during an overnight incubation at 4° C. After washing 3 times with wash buffer (PBS/0.05% Tween-20), the plates were blocked for 1-2 hr with PBS/0.5% bovine serum albumin (BSA). This and all other incubations were performed at room temperature on an orbital shaker. A standard curve of factor D (Complement Technology, Inc., Tyler, Tex.) was prepared in PBS/0.5% BSA/0.05% Tween-20 over a range of 15.6-1,000 μg/ml.

Frozen control samples pre-diluted to quantitate at the high, mid, and low regions of the standard curve were thawed. C1q-depleted human serum and human vitreous fluid and Bruch's membrane lysate samples were diluted using Assay Diluent (PBS/0.5% BSA/0.5% Tween-20). After the blocking step, the plates were washed and the diluted samples (serum, vitreous fluid, and lysates of Bruch's membrane), standards and controls were added and incubated for 2 hours. After the 2 hr incubation, the plates were washed, and bound factor D was detected during a 1 to 2 hr incubation with a biotinylated anti-factor D monoclonal antibody (clone 9G7.1.16, produced at Genentech, diluted to 62.5 ng/ml) followed by a 30 min incubation with streptavidin-horseradish peroxidase (SA-HRP)_(Amersham Pharmacia Biotech, Piscataway, N.J.), diluted 1/10,000 in Assay Diluent. Following a final wash step, tetramethyl benzidine (Kirkegaard & Perry Laboratories, Inc., Gaithersburg, Md.) was added, and color was allowed to develop for 5 to 7 min. The reaction was stopped by the addition of 1 M phosphoric acid. The optical density was read using a microplate reader (450 nm, 650 nm reference), and the sample concentrations were calculated from four-parameter fits of the standard curves. The minimum quantifiable concentrations of factor D in human vitreous fluid and Bruch's membrane lysate samples were 780 pg/mL (1/50 minimum dilution) and 156 µg/mL (1/10 minimum dilution), respectively.

In order to determine the $IC_{50}$ and $IC_{90}$ values for inhibition of the alternative complement pathway using modified anti-Factor D Fab 238 in the presence of factor D concentrations similar to the concentrations of Factor D observed in vitreous fluid and Bruch's membrane tissues from eyes of AMD patients, the hemolytic assay was performed as described in Example 2, using 10% C1q-depleted serum (9.7 nM factor D) or using 10% C1q-depleted serum supplemented with additional factor D (CompTech) to achieve factor D concentrations representing the mean (16.2 nM) or the mean±1 SD (26.5 nM) concentration observed in vitreous fluid and Bruch's membrane tissues from eyes of AMD patients. Data were expressed as % of hemolysis induced in the absence of the inhibitor (FIG. 12). The concentrations of anti-Factor D Fab 238 causing 50% and 90% inhibition of the hemolytic reaction ($IC_{50}$ and $IC_{90}$ values, respectively) were determined for three repeat experiments by non-linear regression of the inhibition curves using a four-parameter fit model (KaleidaGraph, Synergy Software, Reading, Pa.). The molar ratios of the $IC_{50}$ and $IC_{90}$ values versus the relative concentration of Factor D were also calculated. The average $IC_{50}$ and $IC_{90}$ values and molar ratios are shown in Table 3.

TABLE 3

IC50 and IC90 for Anti-Factor D Fab

| Factor D Concentration (nM) | Anti-Factor D Fab (238-1) | | | |
|---|---|---|---|---|
| | IC50 | | IC90 | |
| | nM | Molar ratio ($IC_{50}/fD$) | nM | Molar Ratio ($IC_{90}/fD$) |
| 9.7 (nM) | 4.4 ± 1.5 | 0.454 | 14.0 ± 1.0 | 1.443 |
| 16.2 (nM) | 10.2 ± 0.8 | 0.630 | 38.0 ± 11.0 | 2.346 |
| 26.5 (nM) | 23.9 ± 5.0 | 0.902 | 72.6 ± 4.8 | 2.740 |

Example 5

Duration of Inhibition of Alternative Pathway Complement Activation

The simulated duration of inhibition of the alternative pathway (AP) complement activation in a human eye using a single intravitreal (IVT) injection of anti-Factor D Fab 238 at a 2.5 mg dose (assuming a half-life ($t_{1/2}$) of anti-Factor D Fab 238 of 11.5 days, based on interspecies scaling from the rabbit), was measured (Example 13). The simulated data are based on scaling from a PK study of single intravitreal dose of Fab 238 in the New Zealand white rabbit.

To estimate the half-life of anti-Factor D Fab 238 in humans, the half-life of anti-Factor D 238 in rabbits was calculated. Twelve (12) New Zealand White rabbits were administered a single intravitreal dose of 1 mg Fab 238 in each eye. Vitreous humor and retinal tissue samples were collected from both eyes from the specified number of animals at the following timepoints; 3 animals at 4, 24 and 96 hours (n=6 samples at each of these timepoints) and one animal at 216 hours (n=2 samples at this timepoint) and 2 animals at 240 hours (n=4 samples at this timepoint). The concentrations of Fab 238 in the ocular matrices were measured in a factor D binding ELISA.

The vitreous humor concentration-time data from all animals were analyzed to estimate pharmacokinetic parameter estimates using a naïve pooled approach with the IV bolus input model (Models 201, WinNonlin Pro version 5.2.1; Pharsight Corporation, Mountain View, Calif.) to provide one estimate of terminal half-life ($T_{1/2}$) of 3.83 days. The retinal partition coefficient was calculated as the ratio of the concentration in the retinal tissue to vitreous humor averaged for all eyes at all timepoints, and was equal to 0.24. The PK parameters for vitreous humor were scaled to human using the same scaling factors observed for ranibizumab. The human eye is assumed to have a $V_1$ of 4 mL, the ratio of half-life in the human to the rabbit is assumed to be 3, producing an estimate of $t_{1/2}$ in human of 11.5 days. This produced the estimate for vitreous concentration and retinal tissue concentrations as a function of time as:

$$\text{Vitreous Concentration} = (\text{Dose}/V_1)^* \exp([-\ln(2)/t_{1/2}]^*\text{time})$$

$$\text{Retinal tissue Concentration} = (\text{Dose}/V_1)^* \exp([-\ln(2)/t_{1/2}]^*\text{time})^*(\text{retinal partition coefficient})$$

In FIG. 13, the graph was produced for a single ITV dose of 2.5 mg/eye, and represents time from t=0 to t=112 days. $IC_{90}$ represents the concentration of Fab 238 that produces a 90% inhibitory effect in the hemolysis assay performed as shown in Example 2 and 4 in which 10% pooled human serum was supplemented to a Factor D concentration of 16.2 nM. The assay result was $IC_{90}$=38 nM Fab 238. To compare to the retinal & vitreous concentrations, a molar to mass conversion was done using the following equation:

$$IC_{90} = 38 \times 10^{-9} \text{ moles/L}$$

$$MW \text{ of Fab 238} = 50{,}000 \text{ grams/mole}$$

$$IC_{90} (\text{ug/mL}) = (38 \times 10^{-9} \text{ moles/L}) \times (50 \times 10^3 \text{ grams/mole}) = 1.9 \times 10^{-9} \text{ grams/L, or 1.9 ug/mL}$$

As shown in FIG. 13, the "days above $IC_{90}$" was estimated as the amount of time the vitreous or retinal concentration would be predicted to be above 1.9 ug/mL after a single ITV dose of 2.5 mg/eye, and was observed as the point where the graph of the vitreous or retinal concentrations cross the line at 1.9 ug/mL. A single IVT injection of anti-Factor D Fab 238 was estimated to inhibit AP complement activation in the retinal tissue for at least about 74 days and in the vitreous humor for at least about 97 days. The dashed line in FIG. 13 shows the simulated anti-Factor D Fab 238 concentration in the vitreous humor following intravitreal administration. The solid line in FIG. 13 shows the simulated anti-Factor D Fab 238 concentration in the retinal tissue following intravitreal administration. The difference in the concentration in the vitreous humor and retinal tissue is based upon an estimate of the retinal tissue partition coefficient of 20%; in other words, 20% of the total drug administered to the vitreous humor will have access to the retinal tissue Those skilled in the art will recognize, or be able to ascertain using no more than routine experimentation, many equivalents to the specific embodiments of the invention described herein. Such equivalents are intended to be encompassed by the following claims.

Although the foregoing invention has been described in some detail by way of illustration and example for purposes of clarity of understanding, the descriptions and examples should not be construed as limiting the scope of the invention. The disclosures of all patent and scientific literatures cited herein are expressly incorporated in their entirety by reference.

The foregoing written specification is considered to be sufficient to enable one skilled in the art to practice the invention. The present invention is not to be limited in scope by the construct deposited, since the deposited embodiment is intended as a single illustration of certain aspects of the invention and any constructs that are functionally equivalent are within the scope of this invention. Indeed, various modifications of the invention in addition to those shown and described herein will become apparent to those skilled in the art from the foregoing description and fall within the scope of the appended claims.

We claim:

1. An anti-Factor D antibody or an antigen-binding fragment thereof comprising:
   (a) a light chain variable domain comprising:
      (1) light chain HVR-1 (HVR-L1) comprising the sequence ITSTDIDDDMN (SEQ ID NO: 30) or a sequence that differs from SEQ ID NO: 30 by one or more amino acid substitutions, wherein said one or more substitutions are substitution of the amino acid residue at position 10 of SEQ ID NO: 30 to L or I and/or substitution of the amino acid at position 11 of SEQ ID NO: 30 to A or Q,
      (2) light chain HVR-2 (HVR-L2) comprising the sequence GGNTLRP (SEQ ID NO: 35) or a sequence that differs from SEQ ID NO: 35 by one amino acid substitution, wherein said one substitution is substitution of the amino acid residue at position 3 of SEQ ID NO: 35 to S or A, and,
      (3) light chain HVR-3 (HVR-L3) comprising the sequence LQSDSLPYT (SEQ ID NO: 38); and
   (b) a heavy chain variable domain comprising:
      (1) heavy chain HVR-1 (HVR-H1) comprising the sequence GYTFTNYGMN (SEQ ID NO: 39),
      (2) heavy chain HVR-2 (HVR-H2) comprising the sequence WINTYTGETTYADDFKG (SEQ ID NO: 40), and
      (3) heavy chain HVR-3 (HVR-H3) comprising the sequence EGGVNN (SEQ ID NO: 41) or a sequence that differs from SEQ ID NO: 41 by one or more amino acid substitutions, wherein said one or more substitutions are substitution of the amino acid residue at position 5 of SEQ ID NO: 41 with A or Q and/or substitution of the amino acid residue at position 6 of SEQ ID NO: 41 with A or Q,
   wherein said antibody or antigen-binding fragment thereof comprises at least one of the substitutions set forth in (a)(1), (a)(2), or (b)(3) above and/or the heavy chain variable domain comprises an E at position 1.

2. The anti-Factor D antibody or antigen-binding fragment of claim 1, wherein the anti-Factor D antibody or antigen-binding fragment thereof comprises an E at position 1 of the heavy chain variable domain.

3. The anti-Factor D antibody or antigen-binding fragment of claim 2, wherein the light chain variable domain comprises the amino acid sequence of DIQVTQSPSSLS ASVGDRVTITCITSTDIDDDX$_4$X$_5$WYQQKPGKVPKLLI SGGX$_6$TLRPGVPSRFSGSGSGTDFTLTISSLQPEDVAT YYCLQSDSLPYTFGQGTKX$_7$EIK (SEQ ID NO: 73), wherein X$_4$ is M, L or I; X$_5$ is N, A or Q; X$_6$ is N, S or A; and X$_7$ is L or V.

4. The anti-Factor D antibody or antigen-binding fragment of claim 3, wherein X$_7$ is V.

5. The anti-Factor D antibody or antigen-binding fragment of claim 1, wherein
   (a) the heavy chain variable domain comprises:
      i. an HVR-H1 comprising the amino acid sequence of SEQ ID NO: 39;
      ii. an HVR-H2 comprising the amino acid sequence of SEQ ID NO: 40;
      iii. an HVR-H3 comprising the amino acid sequence of SEQ ID NO: 41, SEQ ID NO: 42, SEQ ID NO: 43, SEQ ID NO: 44 or SEQ ID NO: 45; and
   (b) the light chain variable domain comprises:
      iv. an HVR-L1 comprising the amino acid sequence selected from SEQ ID NO: 30, SEQ ID NO: 31, SEQ ID NO: 32, SEQ ID NO: 33 and SEQ ID NO: 34;
      v. an HVR-L2 comprising the amino acid sequence of SEQ ID NO: 35, SEQ ID NO: 36 or SEQ ID NO: 37; and
      vi. an HVR-L3 comprising the amino acid sequence of SEQ ID NO: 38.

6. The anti-Factor D antibody or antigen-binding fragment of claim 5, wherein the HVR-H3 comprises the amino acid sequence of SEQ ID NO: 41.

7. The anti-Factor D antibody or antigen-binding fragment of claim 5, wherein the HVR-L1 comprises the amino acid sequence of SEQ ID NO: 30.

8. The anti-Factor D antibody or antigen-binding fragment of claim 5, wherein the HVR-L2 comprises the amino acid sequence of SEQ ID NO: 35.

9. The anti-Factor D antibody or antigen-binding fragment of claim 5, wherein the HVR-L1 comprises the amino acid sequence of SEQ ID NO: 30, the HVR-L2 comprises the amino acid sequence of SEQ ID NO: 35, and the HVR-L3 comprises the amino acid sequence of SEQ ID NO: 38.

10. The anti-Factor D antibody or antigen-binding fragment of claim 5, wherein the HVR-H1 comprises the amino acid sequence of SEQ ID NO: 39, the HVR-H2 comprises the amino acid sequence of SEQ ID NO: 40, the HVR-H3 comprises the amino acid sequence of SEQ ID NO: 41, the HVR-L1 comprises the amino acid sequence of SEQ ID NO: 30, the HVR-L2 comprises the amino acid sequence of SEQ ID NO: 35, and the HVR-L3 comprises the amino acid sequence of SEQ ID NO: 38.

11. The anti-Factor D antibody or antigen-binding fragment of claim 10, wherein the light chain variable domain comprises the amino acid sequence of SEQ ID NO: 1, and wherein the amino acid residue at position 104 of SEQ ID NO: 1 is substituted with V.

12. The anti-Factor D antibody or antigen-binding fragment of claim 11, wherein the amino acid residue at position 1 of the heavy chain variable domain is an E.

13. The anti-Factor D antibody or antigen-binding fragment of claim 1, wherein the heavy chain variable domain comprises the sequence of SEQ ID NO: 18, SEQ ID NO: 19, SEQ ID NO: 26, SEQ ID NO: 27, SEQ ID NO: 28 or SEQ ID NO: 29.

14. The anti-Factor D antibody or antigen-binding fragment of claim 1, wherein the light chain variable domain comprises the sequence of SEQ ID NO: 7, SEQ ID NO: 8, SEQ ID NO: 9, SEQ ID NO: 10, SEQ ID NO: 11, SEQ ID NO: 12, SEQ ID NO: 13, or SEQ ID NO: 14.

15. An anti-Factor D antibody or antigen-binding fragment thereof, comprising a polypeptide comprising the following amino acid sequence: $X_1$VQLVQSGPELKKPGASVK VSCKASGYTFTNYGMNWVRQAPGQGLEWMGWINT YTGETTYADDFKGRFVFSLDTSVSTAYLQISSLKAED TAVYYCEREGGVX$_2$X$_3$WGQGTLVTVS S (SEQ ID NO: 74), wherein $X_1$ is E; $X_2$ is N, A or Q; and $X_3$ is N, A or Q.

16. The anti-Factor D antibody or antigen-binding fragment of claim 15, wherein the anti-Factor D antibody or antigen-binding fragment thereof further comprises a polypeptide comprising the following amino acid sequence: DIQVTQSPSSLSASVGDRVTITCITSTDIDDDX$_4$X$_5$WY QQKPGKVPKLLISGGX$_6$TLRPGVPSRFSGSGSGTDFTL TISSLQPEDVATYYCLQSDSLPYTFGQGTKX$_7$EIK (SEQ ID NO:73), wherein $X_4$ is M, L or I; $X_5$ is N, A or Q; $X_6$ is N, S or A; and $X_7$ is L or V.

17. An anti-Factor D antibody or an antigen-binding fragment thereof, comprising the heavy chain variable domain sequence of SEQ ID NO: 19.

18. The anti-Factor D antibody or antigen-binding fragment of claim 17, wherein the anti-Factor D antibody or antibody fragment thereof further comprises the light chain variable domain sequence of SEQ ID NO: 7.

19. An anti-Factor D antibody or antigen-binding fragment thereof, comprising the heavy chain sequence of SEQ ID NO: 63.

20. The anti-Factor D antibody or antigen-binding fragment of claim 19, wherein the anti-Factor D antibody further comprises the light chain sequence of SEQ ID NO: 61.

21. An anti-Factor D antibody or an antigen-binding fragment thereof, comprising:
(a) a light chain variable domain comprising the amino acid sequence of SEQ ID NO: 1, wherein the amino acid residue at position 104 of SEQ ID NO: 1 is substituted with V; and
(b) a heavy chain variable domain comprising an HVR-H1 comprising the amino acid sequence of SEQ ID NO: 39, an HVR-H2 comprising the amino acid sequence of SEQ ID NO: 40, and an HVR-H3 comprising the amino acid sequence of SEQ ID NO: 41, wherein the amino acid residue at position 1 of the heavy chain variable domain is an E.

22. An anti-Factor D antibody or an antigen-binding fragment thereof made by the process of:
(a) culturing a cell expressing an anti-Factor D antibody or an antigen-binding fragment thereof comprising the heavy chain variable domain sequence of SEQ ID NO: 19 and the light chain variable domain sequence of SEQ ID NO: 7; and
(b) isolating the antibody or antigen-binding fragment from said cultured cell.

23. The anti-Factor D antibody or antigen-binding fragment of any one of claims 1, 15, 16, 17, 18 and 21, wherein the anti-Factor D antibody is a monoclonal antibody.

24. The anti-Factor D antibody or antigen-binding fragment of any one of claims 1, 15, 16, 17, 18 and 21, wherein the antigen-binding fragment is a Fab, Fab'-SH, Fv, scFv, or (Fab')$_2$ fragment.

25. The anti-Factor D antibody or antigen-binding fragment of any one of claims 1, 15, 16, 17, 18 and 21, wherein the anti-Factor D antibody is a humanized antibody.

26. The anti-Factor D antibody or antigen-binding fragment of any one of claims 1, 15, 16, 17, 18, 19, 20 and 21, wherein the Factor D is mammalian Factor D.

27. The anti-Factor D antibody or antigen-binding fragment of claim 26, wherein the Factor D is human Factor D.

28. The anti-Factor D antibody or antigen-binding fragment of any one of claims 1, 15, 16, 17, 18, 19, 20 and 21, which is produced in bacteria.

29. The anti-Factor D antibody or antigen-binding fragment of any one of claims 1, 15, 16, 17, 18, 19, 20 and 21, which is produced in CHO cells.

30. A pharmaceutical formulation comprising the anti-Factor D antibody or antigen-binding fragment of any one of claims 1, 15, 16, 17, 18, 19, 20 and 21, and a pharmaceutically acceptable diluent, carrier or excipient.

31. An article of manufacture comprising:
(a) the pharmaceutical formulation of claim 30;
(b) a container; and
(c) a package insert or label indicating that the pharmaceutical formulation-can be used to treat a complement-associated disorder.

32. A kit comprising the anti-Factor D antibody or antigen-binding fragment of any one of claims 1, 15, 16, 17, 18, 19, 20 and 21, and instructions for administering said antibody to treat a complement-associated disorder.

33. The kit of claim 32, wherein the complement-associated disorder is an ocular disease.

34. The kit of claim 33, wherein the ocular disease is selected from the group consisting of age-related macular degeneration (AMD), diabetic retinopathy, choroidal neovascularization (CNV), uveitis, diabetic macular edema, pathological myopia, von Hippel-Lindau disease, histoplasmosis of the eye, Central Retinal Vein Occlusion (CRVO), corneal neovascularization, and retinal neovascularization.

35. The kit of claim 34, wherein the age-related macular degeneration is intermediate dry AMD or geographic atrophy.

* * * * *

UNITED STATES PATENT AND TRADEMARK OFFICE
CERTIFICATE OF CORRECTION

PATENT NO. : 8,273,352 B2
APPLICATION NO. : 12/430479
DATED : September 25, 2012
INVENTOR(S) : Huang et al.

It is certified that error appears in the above-identified patent and that said Letters Patent is hereby corrected as shown below:

In the Drawings (1) In Figure 11, please replace in the legend for the open triangle the term "IC50: 3.5 +/- 0.5 nM" with "IC50: 4.7 +/- 0.6 nM".

(2) In Figure 11, please replace in the legend for the closed triangle the term "IC50: 4.7 +/- 0.6 nM" with "IC50: 3.5 +/- 0.5 nM".

In the Specification (3) In col. 66, line 62, please replace the term "+0.6 nM" with "±0.6 nM".

(4) In col. 66, line 63, please replace the term "+0.5 nM" with "±0.5 nM".

(5) In col. 69, line 56, please replace in the caption of Table 3 the term "Anti-Factor D Fab (238-1)" with "Anti-Factor D Fab (238)".

Signed and Sealed this
Sixteenth Day of June, 2015

Michelle K. Lee
*Director of the United States Patent and Trademark Office*